United States Patent
Bhagirath et al.

(10) Patent No.: US 10,112,928 B2
(45) Date of Patent: *Oct. 30, 2018

(54) INHIBITORS OF SYK

(71) Applicant: Hoffmann-La Roche Inc., Nutley, NJ (US)

(72) Inventors: Niala Bhagirath, New York, NY (US); Joshua Kennedy-Smith, New York, NY (US); Nam T. Le, Verona, NJ (US); Matthew C. Lucas, Lexington, MA (US); Fernando Padilla, Ann Arbor, MI (US); Michael Soth, Glen Rock, NJ (US)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/435,823

(22) PCT Filed: Oct. 15, 2013

(86) PCT No.: PCT/EP2013/071454
§ 371 (c)(1),
(2) Date: Apr. 15, 2015

(87) PCT Pub. No.: WO2014/060371
PCT Pub. Date: Apr. 24, 2014

(65) Prior Publication Data
US 2015/0284367 A1    Oct. 8, 2015

Related U.S. Application Data

(60) Provisional application No. 61/715,897, filed on Oct. 19, 2012.

(51) Int. Cl.
| | |
|---|---|
| C07D 237/24 | (2006.01) |
| C07D 401/12 | (2006.01) |
| A61K 31/50 | (2006.01) |
| A61K 31/501 | (2006.01) |
| C07D 213/72 | (2006.01) |
| C07D 403/12 | (2006.01) |
| A61K 31/44 | (2006.01) |
| A61K 31/506 | (2006.01) |
| C07D 403/04 | (2006.01) |
| C07D 239/557 | (2006.01) |
| A61K 45/06 | (2006.01) |
| A61K 31/505 | (2006.01) |

(52) U.S. Cl.
CPC ............ C07D 403/12 (2013.01); A61K 31/44 (2013.01); A61K 31/50 (2013.01); A61K 31/501 (2013.01); A61K 31/506 (2013.01); A61K 45/06 (2013.01); C07D 213/72 (2013.01); C07D 237/24 (2013.01); C07D 239/557 (2013.01); C07D 401/12 (2013.01); C07D 403/04 (2013.01)

(58) Field of Classification Search
CPC .......................... C07D 237/24; C07D 401/12
See application file for complete search history.

(56) References Cited

U.S. PATENT DOCUMENTS

| | | | |
|---|---|---|---|
| 6,432,963 B1 | 8/2002 | Hisamichi et al. | |
| 6,797,706 B1 | 9/2004 | Segrestin et al. | |
| 8,258,144 B2 | 9/2012 | Song et al. | |
| 8,901,124 B2* | 12/2014 | Hermann | C07D 403/12 514/247 |
| 9,145,414 B2 | 9/2015 | Sakamoto et al. | |

FOREIGN PATENT DOCUMENTS

| | | |
|---|---|---|
| DE | 2705454 A1 | 8/1977 |
| JP | 2008013499 A | 1/2008 |
| WO | 9931073 A1 | 6/1999 |
| WO | 0076980 A1 | 12/2000 |
| WO | 2004002964 A1 | 1/2004 |
| WO | 2006027378 A1 | 3/2006 |
| WO | 2006037117 A1 | 4/2006 |
| WO | 2008009458 A1 | 1/2008 |
| WO | 2009/136995 A2 | 11/2009 |
| WO | 2009145856 A1 | 12/2009 |
| WO | 2010144647 A1 | 12/2010 |
| WO | 2012061418 A2 | 5/2012 |
| WO | 2012061428 A2 | 5/2012 |
| WO | 2013/052239 A1 | 4/2013 |
| WO | 2013/052393 A1 | 4/2013 |
| WO | 2013/078466 A1 | 5/2013 |
| WO | 2013/078468 A1 | 5/2013 |
| WO | 2013/104573 * | 7/2013 |
| WO | 2013192049 A2 | 12/2013 |

OTHER PUBLICATIONS

The International Search Report and Written Opinion, dated Jan. 20, 2014, in the related PCT Appl. No. PCT/EP2013/071454.
The Chinese Office Action, dated Mar. 16, 2016, in the related Chinese Patent Appl. No. 201380054714.4.
Liddle et al., "Discovery of GSK143, a highly potent, selective and orally efficacious spleen tyrosine kinase inhibitor," Bioorganic & Medicinal Chemistry Letters, vol. 21 No. 20 pp. 6188-6194 (2011).
Xie et al., "Pharmacophore modeling study based on known Spleen tyrosine kinase inhibitors together with virtual screening for identifying novel inhibitors," Bioorganic & Medicinal Chemistry Letters, vol. 19.No. 7 pp. 1944-1949 (2009).

(Continued)

*Primary Examiner* — Emily A Bernhardt

(57) ABSTRACT

The present invention relates to the use of novel compounds of formula I: wherein all variable substituents are defined as described herein, which are SYK inhibitors and are useful for the treatment of auto-immune and inflammatory diseases.

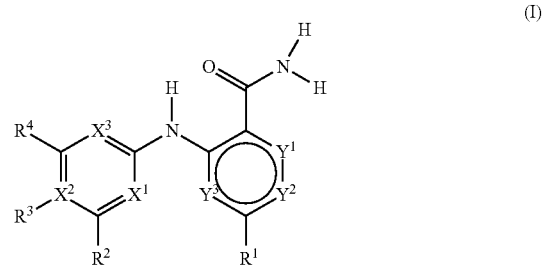

(I)

11 Claims, No Drawings

(56) References Cited

OTHER PUBLICATIONS

Hisamichi et al., "Synthetic studies on novel Syk inhibitors. Part 1: Synthesis and structure—activity relationships of pyrimidine-5-carboxamide derivatives," Bioorganic & Medicinal Chemistry Letters, vol. 13 No. 16 pp. 4936-4951 (2005).
The Japanese Office Action, dated Aug. 8, 2017, in the related Japanese Patent Appl. No. 2015-537213.
The European Communication, dated Oct. 6, 2017, in the related European Appl. No. 13 777 038.4.
The English translation of the Russian Office Action, dated Sep. 20, 2017, in the related Russian Application No. 2015116532/04(025705).

\* cited by examiner

INHIBITORS OF SYK

This application is a National Stage Application of PCT/EP2013/071454 filed Oct. 15, 2013, which claims priority from U.S. Provisional Patent Application No. 61/715,897, filed on Oct. 19, 2012. The priority of both said PCT and U.S. Provisional Patent Application are claimed. Each of the prior mentioned applications is hereby incorporated by reference herein in its entirety.

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

SYK (Spleen Tyrosine Kinase) is a non-receptor tyrosine kinase that is essential for B-cell activation through BCR signaling. SYK becomes activated upon binding to phosphorylated BCR and thus initiates the early signaling events following BCR activation. Mice deficient in SYK exhibit an early block in B-cell development. Therefore inhibition of SYK enzymatic activity in cells is proposed as a treatment for autoimmune disease through its effects on autoantibody production.

In addition to the role of SYK in BCR signaling and B-cell activation, it also plays a key role in FcεRI mediated mast cell degranulation and eosinophil activation. Thus, SYK is implicated in allergic disorders including asthma. SYK binds to the phosphorylated gamma chain of FcγRI via its SH2 domains and is essential for downstream signaling. SYK deficient mast cells demonstrate defective degranulation, arachidonic acid and cytokine secretion. This also has been shown for pharmacologic agents that inhibit SYK activity in mast cells. Treatment with SYK antisense oligonucleotides inhibits antigen-induced infiltration of eosinophils and neutrophils in an animal model of asthma. SYK deficient eosinophils also show impaired activation in response to FcεR stimulation. Therefore, small molecule inhibitors of SYK will be useful for treatment of allergy-induced inflammatory diseases including asthma.

In view of the numerous conditions that are contemplated to benefit by treatment involving modulation of the SYK pathway it is immediately apparent that new compounds that modulate the SYK pathway and methods of using these compounds should provide substantial therapeutic benefits to a wide variety of patients. Provided herein are novel compounds for use in the therapeutic treatment of autoimmune and inflammatory diseases by targeting the SYK pathway or by inhibition of SYK kinase.

The application provides a compound of Formula I

The application provides a method for treating an inflammatory or autoimmune condition comprising administering to a patient in need thereof a therapeutically effective amount of the compound of Formula I.

The application provides a compound of Formula I

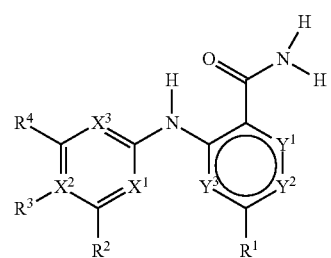

wherein:
$R^1$ is Cl, —$OR^{1'}$, —$NR^{1'}$, $(CH_2)_n R^{1'}$, or oxo;
$R^{1'}$ is phenyl, pyridyl, cycloalkyl, amino cycloalkyl lower alkyl or lower alkyl, optionally substituted with one or more $R^{1''}$;
    each $R^{1''}$ is independently cyano, amino, amino lower alkyl, halo, lower alkyl, cycloalkyl, or amino cycloalkyl lower alkyl;
$R^2$ is lower alkyl, cycloalkyl, cyano lower alkyl, hydroxy lower alkyl, halo lower alkyl, dialkyl amino, or lower alkoxy;
$R^3$ is absent, H, lower alkoxy, lower alkyl, or halo;
$R^4$ is H or lower alkyl;
$X^1$ is CH or N;
$X^2$ is CH, $CR^2$ or N;
$X^3$ is CH or N;
$Y^1$ is CH or N; and
$Y^2$ is CH or N;
$Y^3$ is CH or N;
or a pharmaceutically acceptable salt thereof.

The application provides a pharmaceutical composition comprising the compound of Formula I, admixed with at least one pharmaceutically acceptable carrier, excipient or diluent.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

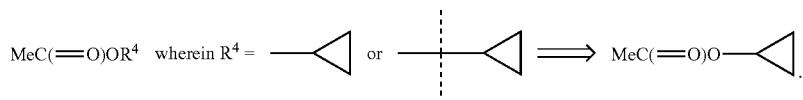

A bond drawn into ring system (as opposed to connected at a distinct vertex) indicates that the bond may be attached to any of the suitable ring atoms The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—⇌—C(—OH)=CH—), amide/imidic acid (—C(=O)—NH—⇌—C(—OH)=N—) and amidine (—C(=NR)—NH—⇌—C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro [3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —$CH_2$CH(i-Pr)$CH_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethylethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups. The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "carboxy-alkyl" as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —$CO_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N,O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of SYK

The application provides a compound of Formula I

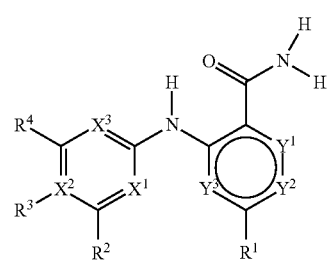

I wherein:
$R^1$ is Cl, —$OR^{1'}$, —$NR^{1'}$, $(CH_2)_nR^{1'}$, or oxo;
$R^{1'}$ is phenyl, pyridyl, cycloalkyl, amino cycloalkyl lower alkyl or lower alkyl, optionally substituted with one or more $R^{1''}$;

each $R^{1'''}$ is independently cyano, amino, amino lower alkyl, halo, lower alkyl, cycloalkyl, or amino cycloalkyl lower alkyl;

$R^2$ is lower alkyl, cycloalkyl, cyano lower alkyl, hydroxy lower alkyl, halo lower alkyl, dialkyl amino, or lower alkoxy;

$R^3$ is absent, H, lower alkoxy, lower alkyl, or halo;

$R^4$ is H or lower alkyl;

$X^1$ is CH or N;

$X^2$ is CH, $CR^2$ or N;

$X^3$ is CH or N;

$Y^1$ is CH or N; and $Y^2$ is CH or N;

$Y^3$ is CH or N;

n is 0 or 1;

or a pharmaceutically acceptable salt thereof.

The application provides a compound of formula I wherein:

$R^1$ is —$OR^{1'}$, —$NR^{1'}$, $(CH_2)_n R^{1'}$, or oxo;

$R^{1'}$ is phenyl, pyridyl, cycloalkyl, or lower alkyl, optionally substituted with one or more $R^{1'''}$;

each $R^{1'''}$ is independently cyano, amino, amino lower alkyl, halo, lower alkyl, cycloalkyl, or amino cycloalkyl lower alkyl;

$R^2$ is lower alkyl, cycloalkyl, cyano lower alkyl, hydroxy lower alkyl, halo lower alkyl, dialkyl amino, or lower alkoxy;

$R^3$ is absent, H, lower alkoxy, lower alkyl, or halo;

$R^4$ is H or lower alkyl;

$X^1$ is CH or N;

$X^2$ is CH, $CR^2$ or N;

$X^3$ is CH or N;

$Y^1$ is CH or N; and $Y^2$ is CH or N;

$Y^3$ is CH or N;

or a pharmaceutically acceptable salt thereof.

The application provides a compound of Formula I wherein $Y^1$ and $Y^2$ are N.

The application provides a compound of Formula I wherein $R^1$ is —$NR^{1'}$, optionally substituted with one or more $R^{1'}$.

The application provides a compound of Formula I wherein $R^1$ is —$NR^{1'}$, optionally substituted with one or more $R^{1'''}$, and $Y^1$ and $Y^2$ are N.

The application provides a compound of Formula I wherein $R^{1'}$ is lower alkyl, optionally substituted with one or more $R^{1'''}$.

The application provides a compound of Formula I wherein $R^{1'}$ is lower alkyl, optionally substituted with one or more $R^{1'''}$ and $Y^1$ and $Y^2$ are N.

The application provides a compound of Formula I wherein $R^{1'}$ is lower alkyl, optionally substituted with one or more $R^{1'''}$ and $R^1$ is —$NR^{1'}$, optionally substituted with one or more $R^{1'''}$.

The application provides a compound of Formula I wherein $R^{1'}$ is lower alkyl, optionally substituted with one or more $R^{1'''}$, $R^1$ is —$NR^{1'}$, optionally substituted with one or more $R^{1'''}$, and $Y^1$ and $Y^2$ are N.

The application provides a compound of Formula I wherein $R^{1'''}$ is amino lower alkyl.

The application provides a compound of Formula I wherein $R^{1'''}$ is amino lower alkyl and $Y^1$ and $Y^2$ are N.

The application provides a compound of Formula I wherein $R^{1'''}$ is amino lower alkyl and $R^1$ is —$NR^{1'}$, optionally substituted with one or more $R^{1'''}$.

The application provides a compound of Formula I wherein $R^{1'''}$ is amino lower alkyl, $Y^1$ and $Y^2$ are N, and $R^1$ is —$NR^{1'}$, optionally substituted with one or more $R^{1'''}$.

The application provides a compound of Formula I wherein $R^{1'}$ is lower alkyl, optionally substituted with one or more $R^{1'''}$, $R^{1'''}$ is amino lower alkyl, $Y^1$ and $Y^2$ are N, and $R^1$ is —$NR^{1'}$, optionally substituted with one or more $R^{1'''}$.

The application provides a compound of Formula I wherein $R^{1'''}$ is amino lower alkyl.

The application provides a compound of Formula I wherein $R^{1'''}$ is amino lower alkyl and $Y^1$ and $Y^2$ are N.

The application provides a compound of Formula I wherein $R^{1'''}$ is amino lower alkyl and $R^1$ is —$NR^{1'}$, optionally substituted with one or more $R^{1'''}$.

The application provides a compound of Formula I wherein $R^{1'}$ is lower alkyl, optionally substituted with one or more $R^{1'''}$ and $R^{1'''}$ is amino lower alkyl.

The application provides a compound of Formula I wherein $R^{1'}$ is lower alkyl, optionally substituted with one or more $R^{1'''}$, $R^{1'''}$ is amino lower alkyl, $Y^1$ and $Y^2$ are N, $R^1$ is —$NR^{1'}$, optionally substituted with one or more $R^{1'''}$.

The application provides a compound of Formula I wherein $R^{1'''}$ is amino lower alkyl and $Y^1$ and $Y^2$ are N.

The application provides a compound of Formula I wherein $R^{1'''}$ is amino lower alkyl, $R^1$ is —$NR^{1'}$, optionally substituted with one or more $R^{1'''}$, and $Y^1$ and $Y^2$ are N.

The application provides a compound of Formula I wherein $X^1$ is N.

The application provides a compound of Formula I wherein $X^1$ is N, $R^{1'}$ is lower alkyl, optionally substituted with one or more $R^{1'''}$, $R^{1'''}$ is amino lower alkyl, $Y^1$ and $Y^2$ are N, and $R^1$ is —$NR^{1'}$, optionally substituted with one or more $R^{1'''}$.

The application provides a compound of Formula I wherein $X^1$ is N, $R^{1'''}$ is amino lower alkyl, $Y^1$ and $Y^2$ are N, and $R^1$ is —$NR^{1'}$, optionally substituted with one or more $R^{1'''}$.

The application provides a compound of Formula I wherein $X^1$ is N, $Y^1$ and $Y^2$ are N, and $R^1$ is —$NR^{1'}$, optionally substituted with one or more $R^{1'''}$.

The application provides a compound of Formula I wherein $X^1$ is N, $Y^1$ and $Y^2$ are N.

The application provides a compound of Formula I wherein $X^1$ is N and $R^1$ is —$NR^{1'}$, optionally substituted with one or more $R^{1'''}$.

The application provides a compound of Formula I wherein $X^2$ is C and $X^3$ is CH.

The application provides a compound of Formula I wherein $X^2$ is C and $X^3$ is CH and $Y^1$ and $Y^2$ are N.

The application provides a compound of Formula I wherein $X^2$ is C and $X^3$ is CH and $R^1$ is —$NR^{1'}$, optionally substituted with one or more $R^{1'''}$.

The application provides a compound of Formula I wherein $X^2$ is C and $X^3$ is CH, and $X^1$ is N.

The application provides a compound of Formula I wherein $X^2$ is C and $X^3$ is CH, $X^1$ is N.

The application provides a compound of Formula I wherein $X^2$ is C and $X^3$ is CH, and $R^1$ is —$NR^{1'}$, optionally substituted with one or more $R^{1'''}$.

The application provides a compound of Formula I wherein $X^2$ is C and $X^3$ is CH, and $R^1$ is —$NR^{1'}$, optionally substituted with one or more $R^{1'''}$, and $R^{1'''}$ is amino lower alkyl.

The application provides a compound of Formula I wherein $R^4$ is H.

The application provides a compound of Formula I wherein $R^4$ is H and $X^2$ is C and $X^3$ is CH.

The application provides a compound of Formula I wherein $R^4$ is H, and $R^1$ is —$NR^{1'}$, optionally substituted with one or more $R^{1''}$.

The application provides a compound of Formula I wherein $R^4$ is H, and $R^{1''}$ is amino lower alkyl.

The application provides a compound of Formula I wherein $R^4$ is H, $X^2$ is C, $X^3$ is CH, $R^1$ is —$NR^{1'}$, optionally substituted with one or more $R^{1''}$, and $R^{1''}$ is amino lower alkyl.

The application provides a compound of Formula I wherein $R^4$ is H, $X^2$ is C, $X^3$ is CH, $R^1$ is —$NR^{1'}$, optionally substituted with one or more $R^{1''}$, and $R^{1''}$ is amino lower alkyl, and $Y^1$ and $Y^2$ are N.

The application provides a compound of Formula I wherein $R^2$ is lower alkyl.

The application provides a compound of Formula I wherein $R^2$ is lower alkyl, $R^4$ is H, $X^2$ is C, $X^3$ is CH, $R^1$ is —$NR^{1'}$, optionally substituted with one or more $R^{1''}$, and $R^{1''}$ is amino lower alkyl, and $Y^1$ and $Y^2$ are N.

The application provides a compound of Formula I wherein $R^2$ is lower alkyl, $X^2$ is C, $X^3$ is CH, $R^1$ is —$NR^{1'}$, optionally substituted with one or more $R^{1''}$, and $R^{1''}$ is amino lower alkyl, and $Y^1$ and $Y^2$ are N.

The application provides a compound of Formula I wherein $R^2$ is lower alkyl, $X^3$ is CH, $R^1$ is —$NR^{1'}$, optionally substituted with one or more $R^{1''}$, and $R^{1''}$ is amino lower alkyl, and $Y^1$ and $Y^2$ are N.

The application provides a compound of Formula I wherein $R^2$ is lower alkyl, $R^1$ is —$NR^{1'}$, optionally substituted with one or more $R^{1''}$, and $R^{1''}$ is amino lower alkyl, and $Y^1$ and $Y^2$ are N.

The application provides a compound of Formula I wherein $R^2$ is lower alkyl, and $R^1$ is —$NR^{1'}$, optionally substituted with one or more $R^{1''}$.

The application provides a compound of Formula I wherein $R^2$ is lower alkyl, and $R^{1''}$ is amino lower alkyl.

The application provides a compound of Formula I, wherein $R^3$ is lower alkoxy or lower alkyl.

The application provides a compound of Formula I, wherein $R^1$ is —$OR^{1'}$, optionally substituted with one or more $R^{1''}$.

The application provides a compound of Formula I, wherein $R^3$ is absent.

The application provides a compound of Formula I, wherein n is 0.

The application provides a compound selected from the group consisting of:

4-(6-methylpyridin-2-ylamino)-6-phenoxypyridazine-3-carboxamide;
6-(3-cyanophenoxy)-4-(6-methylpyridin-2-ylamino)pyridazine-3-carboxamide;
6-(3-(2-aminopropan-2-yl)phenoxy)-4-(6-methylpyridin-2-ylamino)pyridazine-3-carboxamide;
6-(3-fluorophenoxy)-4-(6-methylpyridin-2-ylamino)pyridazine-3-carboxamide;
4-(6-methylpyridin-2-ylamino)-6-(pyridin-3-yloxy)pyridazine-3-carboxamide;
6-(2-cyanophenoxy)-4-(6-methylpyridin-2-ylamino)pyridazine-3-carboxamide;
6-(2-ethylphenoxy)-4-(6-methylpyridin-2-ylamino)pyridazine-3-carboxamide;
4-(6-methylpyridin-2-ylamino)-6-(o-tolyloxy)pyridazine-3-carboxamide;
6-(4-chloro-2-cyanophenoxy)-4-(6-methylpyridin-2-ylamino)pyridazine-3-carboxamide;
6-(2-cyclopropylphenoxy)-4-(6-methylpyridin-2-ylamino)pyridazine-3-carboxamide;
4-(6-Cyclopropyl-pyridin-2-ylamino)-6-oxo-1,6-dihydro-pyridazine-3-carboxylic acid amide;
6-(1-amino-4-methylpentan-2-ylamino)-4-(6-tert-butylpyridin-2-ylamino)pyridazine-3-carboxamide;
6-(2-aminoethoxy)-4-(5,6-dimethylpyridin-2-ylamino)pyridazine-3-carboxamide;
6-chloro-4-(3,5-dimethylphenylamino)pyridazine-3-carboxamide;
6-(1-Aminomethyl-3-methyl-butylamino)-4-(6-isopropyl-5-methyl-pyridin-2-ylamino)-pyridazine-3-carboxylic acid amide;
6-(2-aminoethylamino)-4-(6-tert-butylpyridin-2-ylamino)pyridazine-3-carboxamide;
6-((R)-1-Aminomethyl-3-methyl-butylamino)-4-(6-#tert!-butyl-pyridin-2-ylamino)-pyridazine-3-carboxylic acid amide;
6-(2-aminoethylamino)-4-(6-isopropyl-5-methylpyridin-2-ylamino)pyridazine-3-carboxamide;
6-((1-aminocyclopropyl)methylamino)-4-(6-tert-butylpyridin-2-ylamino)pyridazine-3-carboxamide;
6-(2-aminoethylamino)-4-(6-isopropyl-5-methoxypyridin-2-ylamino)pyridazine-3-carboxamide;
6-(2-aminoethylamino)-4-(6-(2-cyanopropan-2-yl)pyridin-2-ylamino)pyridazine-3-carboxamide;
2-(3-Amino-propyl)-4-m-tolylamino-pyrimidine-5-carboxylic acid amide;
6-(2-aminoethylamino)-4-(6-(2-hydroxypropan-2-yl)pyridin-2-ylamino)pyridazine-3-carboxamide;
6-(2-aminoethylamino)-4-(4,6-dimethylpyrimidin-2-ylamino)pyridazine-3-carboxamide;
6-(2-aminoethylamino)-4-(6-(trifluoromethyl)pyridin-2-ylamino)pyridazine-3-carboxamide;
6-(2-aminoethylamino)-4-(5-methoxy-6-propylpyridin-2-ylamino)pyridazine-3-carboxamide;
6-(2-aminoethylamino)-4-(6-(dimethylamino)-5-methyl-pyridin-2-ylamino)pyridazine-3-carboxamide;
6-(2-aminoethylamino)-4-(2-tert-butylpyrimidin-4-ylamino)pyridazine-3-carboxamide;
6-(2-aminoethylamino)-4-(6-(2-methoxypropan-2-yl)pyridin-2-ylamino)pyridazine-3-carboxamide;
4-((1R,2S)-2-Amino-cyclohexylamino)-2-(6-methyl-pyridin-2-ylamino)-benzamide;
6-(2-aminoethylamino)-4-(5-isopropyl-6-methoxypyridin-2-ylamino)pyridazine-3-carboxamide;
6-(2-aminoethylamino)-4-(5-fluoro-6-isopropylpyridin-2-ylamino)pyridazine-3-carboxamide;
6-(2-aminoethylamino)-4-(6-isopropoxypyridin-2-ylamino)pyridazine-3-carboxamide; and
6-(2-Aminoethylamino)-4-(5,6-dimethylpyridin-2-ylamino)pyridazine-3-carboxamide.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

The application provides a pharmaceutical composition comprising the compound of Formula I, admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides the use of the compound of formula I for the manufacture of a medicament useful for the treatment of disorders associated with Syk.

The application provides the use of the compound of formula I for the manufacture of a medicament useful for the treatment of rheumatoid arthritis.

A compound, method, or composition as described herein.

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system or Struct=Name, a CambridgeSoft® application, for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of compounds according to generic Formula I.

TABLE I

| Compound | Nomenclature | Structure |
| --- | --- | --- |
| I-1 | 4-(6-methylpyridin-2-ylamino)-6-phenoxypyridazine-3-carboxamide | 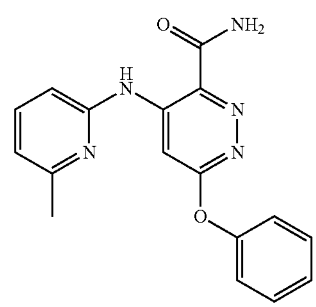 [SMILES: Cc1cccc(Nc2cc(Oc3ccccc3)nnc2C(N)=O)n1] |
| I-2 | 6-(3-cyanophenoxy)-4-(6-methylpyridin-2-ylamino)pyridazine-3-carboxamide | 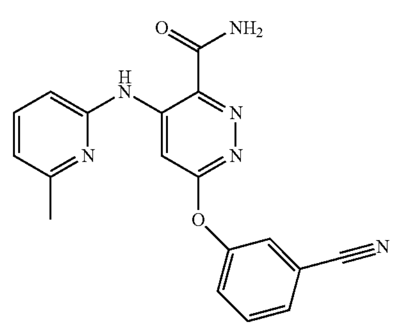 [SMILES: Cc1cccc(Nc2cc(Oc3cccc(C#N)c3)nnc2C(N)=O)n1] |

TABLE I-continued

| Compound | Nomenclature | Structure |
|---|---|---|
| I-3 | 6-(3-(2-aminopropan-2-yl)phenoxy)-4-(6-methylpyridin-2-ylamino)pyridazine-3-carboxamide | 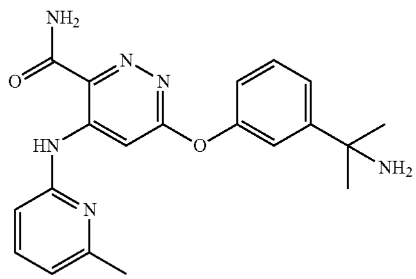 [SMILES: Cc1cccc(Nc2cc(Oc3cccc(C(C)(C)N)c3)nnc2C(N)=O)n1] |
| I-4 | 6-(3-fluorophenoxy)-4-(6-methylpyridin-2-ylamino)pyridazine-3-carboxamide | 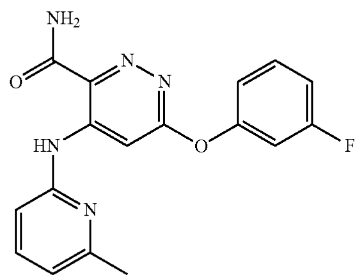 [SMILES: Cc1cccc(Nc2cc(Oc3cccc(F)c3)nnc2C(N)=O)n1] |
| I-5 | 4-(6-methylpyridin-2-ylamino)-6-(pyridin-3-yloxy)pyridazine-3-carboxamide | 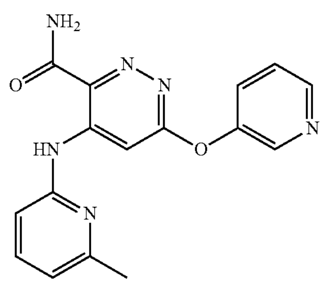 [SMILES: Cc1cccc(Nc2cc(Oc3cccnc3)nnc2C(N)=O)n1] |
| I-6 | 6-(2-cyanophenoxy)-4-(6-methylpyridin-2-ylamino)pyridazine-3-carboxamide | 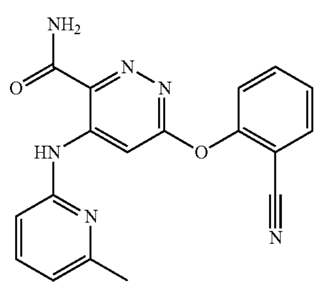 [SMILES: Cc1cccc(Nc2cc(Oc3ccccc3C#N)nnc2C(N)=O)n1] |
| I-7 | 6-(2-ethylphenoxy)-4-(6-methylpyridin-2-ylamino)pyridazine-3-carboxamide | 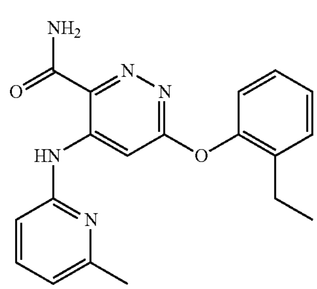 [SMILES: CCc1ccccc1Oc1cc(Nc2cccc(C)n2)c(C(N)=O)nn1] |

TABLE I-continued

| Compound | Nomenclature | Structure |
|---|---|---|
| I-8 | 4-(6-methylpyridin-2-ylamino)-6-(o-tolyloxy)pyridazine-3-carboxamide | 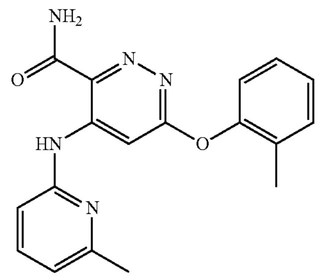 [SMILES: Cc1cccc(Nc2cc(Oc3ccccc3C)nnc2C(N)=O)n1] |
| I-9 | 6-(4-chloro-2-cyanophenoxy)-4-(6-methylpyridin-2-ylamino)pyridazine-3-carboxamide | 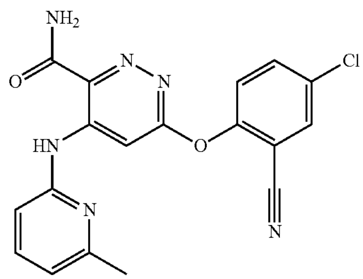 [SMILES: Cc1cccc(Nc2cc(Oc3ccc(Cl)cc3C#N)nnc2C(N)=O)n1] |
| I-10 | 6-(2-cyclopropylphenoxy)-4-(6-methylpyridin-2-ylamino)pyridazine-3-carboxamide | 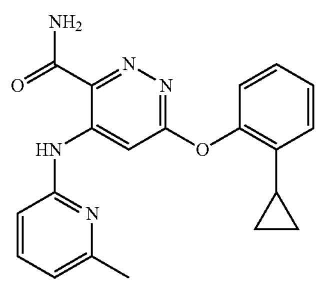 [SMILES: Cc1cccc(Nc2cc(Oc3ccccc3C3CC3)nnc2C(N)=O)n1] |
| I-11 | 4-(6-cyclopropyl-pyridin-2-ylamino)-6-oxo-1,6-dihydro-pyridazine-3-carboxylic acid amide | 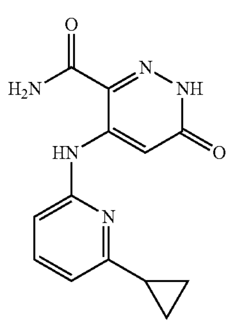 [SMILES: NC(=O)c1n[nH]c(=O)cc1Nc1cccc(C2CC2)n1] |
| I-12 | 6-(1-amino-4-methylpentan-2-ylamino)-4-(6-tert-butylpyridin-2-ylamino)pyridazine-3-carboxamide | 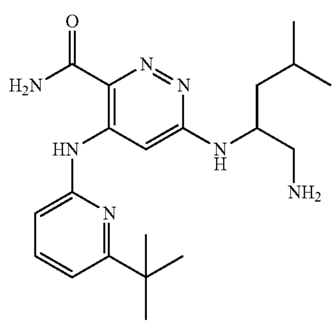 [SMILES: CC(C)CC(CN)Nc1cc(Nc2cccc(C(C)(C)C)n2)c(C(N)=O)nn1] |

TABLE I-continued

| Compound | Nomenclature | Structure |
|---|---|---|
| I-13 | 6-(2-aminoethoxy)-4-(5,6-dimethylpyridin-2-ylamino)pyridazine-3-carboxamide | 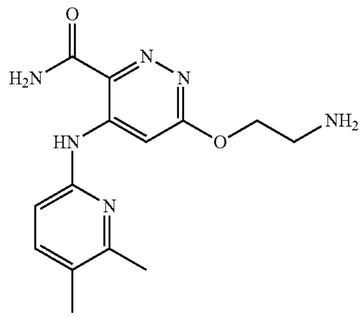 [SMILES: Cc1ccc(Nc2cc(OCCN)nnc2C(N)=O)nc1C] |
| I-14 | 6-chloro-4-(3,5-dimethylphenyl-amino)pyridazine-3-carboxamide | 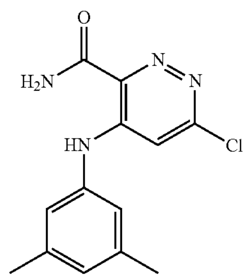 [SMILES: Cc1cc(C)cc(Nc2cc(Cl)nnc2C(N)=O)c1] |
| I-15 | 6-(1-aminomethyl-3-methyl-butylamino)-4-(6-isopropyl-5-methyl-pyridin-2-ylamino)-pyridazine-3-carboxylic acid amide | 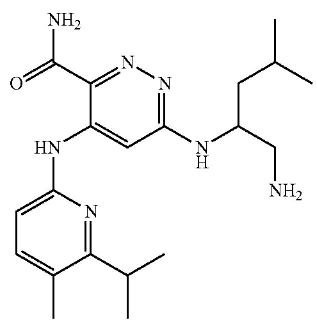 [SMILES: Cc1ccc(Nc2cc(NC(CN)CC(C)C)nnc2C(N)=O)nc1C(C)C] |
| I-16 | 6-(2-aminoethylamino)-4-(6-tert-butylpyridin-2-ylamino)pyridazine-3-carboxamide | 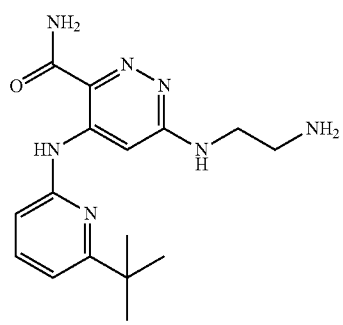 [SMILES: CC(C)(C)c1cccc(Nc2cc(NCCN)nnc2C(N)=O)n1] |
| I-17 | 6-((R)-1-aminomethyl-3-methyl-butylamino)-4-(6-#tert!-butyl-pyridin-2-ylamino)-pyridazine-3-carboxylic acid amide | 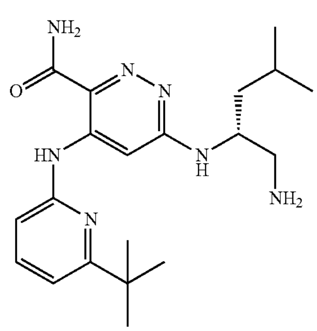 [SMILES: CC(C)C[C@H](CN)Nc1cc(Nc2cccc(C(C)(C)C)n2)c(C(N)=O)nn1] |

TABLE I-continued

| Compound | Nomenclature | Structure |
|---|---|---|
| I-18 | 6-(2-aminoethylamino)-4-(6-isopropyl-5-methylpyridin-2-ylamino)pyridazine-3-carboxamide | 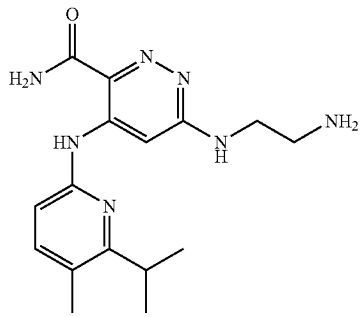 [SMILES: Cc1ccc(Nc2cc(NCCN)nnc2C(N)=O)nc1C(C)C] |
| I-19 | 6-((1-aminocyclopropyl)methylamino)-4-(6-tert-butylpyridin-2-ylamino)pyridazine-3-carboxamide | 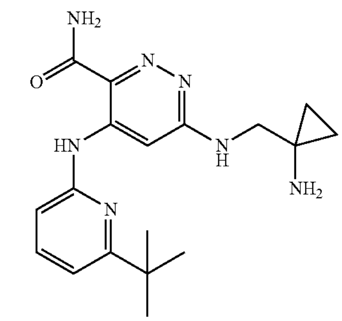 [SMILES: CC(C)(C)c1cccc(Nc2cc(NCC3(N)CC3)nnc2C(N)=O)n1] |
| I-20 | 6-(2-aminoethylamino)-4-(6-isopropyl-5-methoxypyridin-2-ylamino)pyridazine-3-carboxamide | 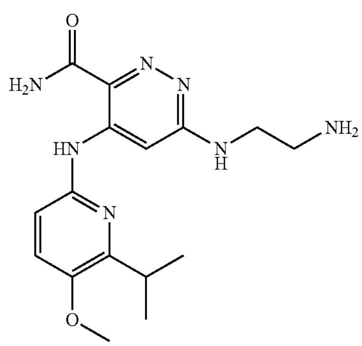 [SMILES: COc1ccc(Nc2cc(NCCN)nnc2C(N)=O)nc1C(C)C] |
| I-21 | 6-(2-aminoethylamino)-4-(6-(2-cyanopropan-2-yl)pyridin-2-ylamino)pyridazine-3-carboxamide | 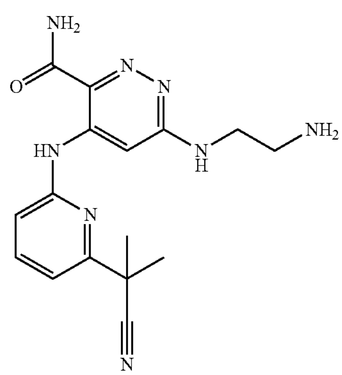 [SMILES: CC(C)(C#N)c1cccc(Nc2cc(NCCN)nnc2C(N)=O)n1] |
| I-22 | 2-(3-amino-propyl)-4-m-tolylamino-pyrimidine-5-carboxylic acid amide | 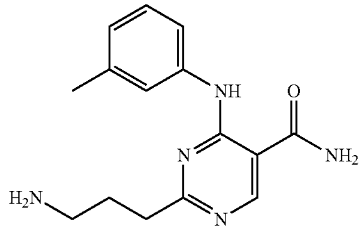 [SMILES: Cc1cccc(Nc2nc(CCCN)ncc2C(N)=O)c1] |

TABLE I-continued

| Compound | Nomenclature | Structure |
|---|---|---|
| I-23 | 6-(2-aminoethylamino)-4-(6-(2-hydroxypropan-2-yl)pyridin-2-ylamino)pyridazine-3-carboxamide | 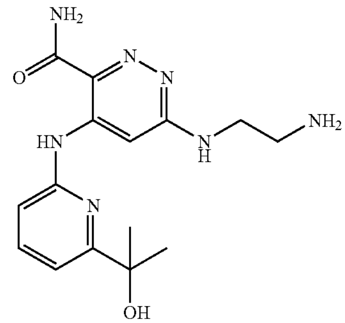 [SMILES: CC(C)(O)c1cccc(Nc2cc(NCCN)nnc2C(N)=O)n1] |
| I-24 | 6-(2-aminoethylamino)-4-(4,6-dimethylpyrimidin-2-ylamino)pyridazine-3-carboxamide | 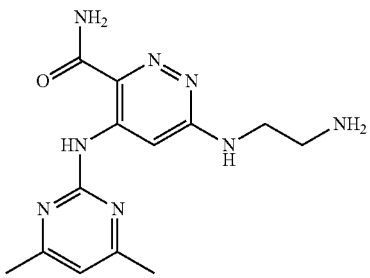 [SMILES: Cc1cc(C)nc(Nc2cc(NCCN)nnc2C(N)=O)n1] |
| I-25 | 6-(2-aminoethylamino)-4-(6-(trifluoromethyl)pyridin-2-ylamino)pyridazine-3-carboxamide | 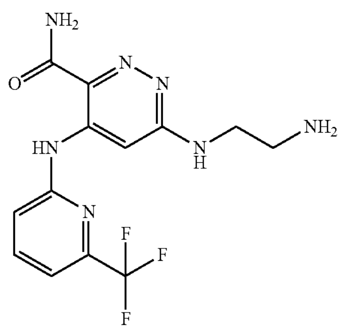 [SMILES: NCCNc1cc(Nc2cccc(C(F)(F)F)n2)c(C(N)=O)nn1] |
| I-26 | 6-(2-aminoethylamino)-4-(5-methoxy-6-propylpyridin-2-ylamino)pyridazine-3-carboxamide | 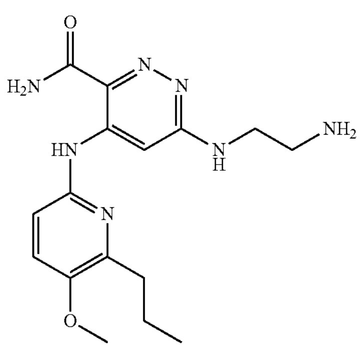 [SMILES: CCCc1nc(Nc2cc(NCCN)nnc2C(N)=O)ccc1OC] |
| I-27 | 6-(2-aminoethylamino)-4-(6-(dimethylamino)-5-methylpyridin-2-ylamino)pyridazine-3-carboxamide | 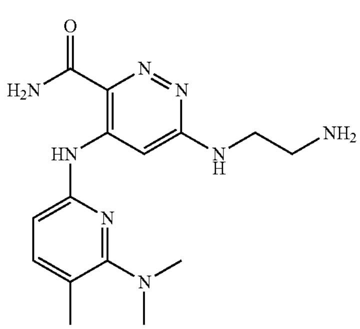 [SMILES: Cc1ccc(Nc2cc(NCCN)nnc2C(N)=O)nc1N(C)C] |

TABLE I-continued

| Compound | Nomenclature | Structure |
|---|---|---|
| I-28 | 6-(2-aminoethylamino)-4-(2-tert-butylpyrimidin-4-ylamino)pyridazine-3-carboxamide | 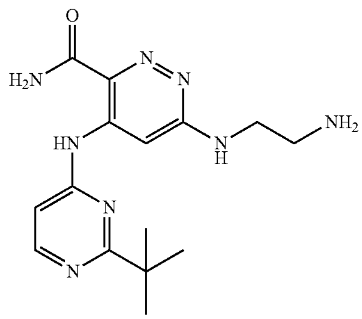 [SMILES: CC(C)(C)c1nccc(Nc2cc(NCCN)nnc2C(N)=O)n1] |
| I-29 | 6-(2-aminoethylamino)-4-(6-(2-methoxypropan-2-yl)pyridin-2-ylamino)pyridazine-3-carboxamide | 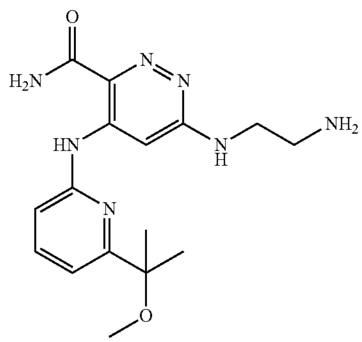 [SMILES: COC(C)(C)c1cccc(Nc2cc(NCCN)nnc2C(N)=O)n1] |
| I-30 | 4-((1R,2S)-2-amino-cyclohexylamino)-2-(6-methyl-pyridin-2-ylamino)-benzamide | 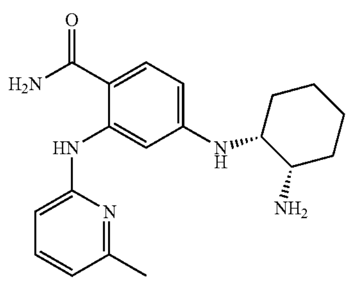 [SMILES: Cc1cccc(Nc2cc(N[C@@H]3CCCC[C@@H]3N)ccc2C(N)=O)n1] |
| I-31 | 6-(2-aminoethylamino)-4-(5-isopropyl-6-methoxypyridin-2-ylamino)pyridazine-3-carboxamide | 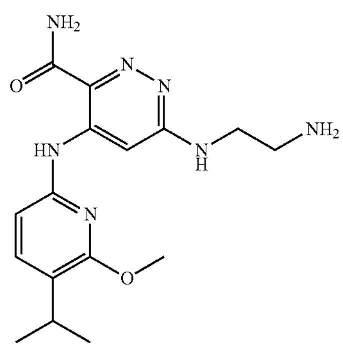 [SMILES: COc1nc(Nc2cc(NCCN)nnc2C(N)=O)ccc1C(C)C] |
| I-32 | 6-(2-aminoethylamino)-4-(5-fluoro-6-isopropylpyridin-2-ylamino)pyridazine-3-carboxamide | 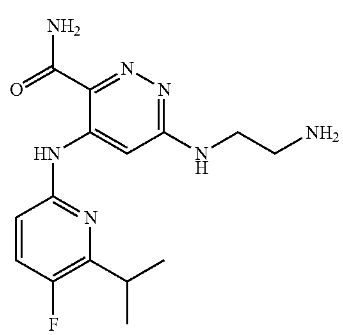 [SMILES: CC(C)c1nc(Nc2cc(NCCN)nnc2C(N)=O)ccc1F] |

TABLE I-continued

| Compound | Nomenclature | Structure |
|---|---|---|
| I-33 | 6-(2-aminoethylamino)-4-(6-isopropoxypyridin-2-ylamino)pyridazine-3-carboxamide | 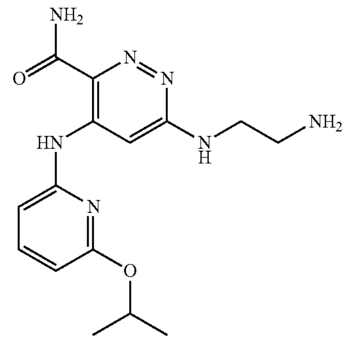 [SMILES: CC(C)Oc1cccc(Nc2cc(NCCN)nnc2C(N)=O)n1] |
| I-34 | 6-(2-aminoethylamino)-4-(5,6-dimethylpyridin-2-ylamino)pyridazine-3-carboxamide | 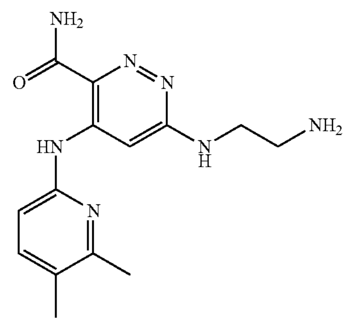 [SMILES: Cc1ccc(Nc2cc(NCCN)nnc2C(N)=O)nc1C] |

Synthesis

General Schemes

In the below general schemes, Q can be CH or N; R1, R2, and R3 can be H or lower alkyl; n can be 0, 1, 2, or 3, Y can be lower alkyl, cycloalkyl, cyano lower alkyl, hydroxy lower alkyl, halo lower alkyl, dialkyl amino, lower alkoxy, H, or halo.

General Scheme I

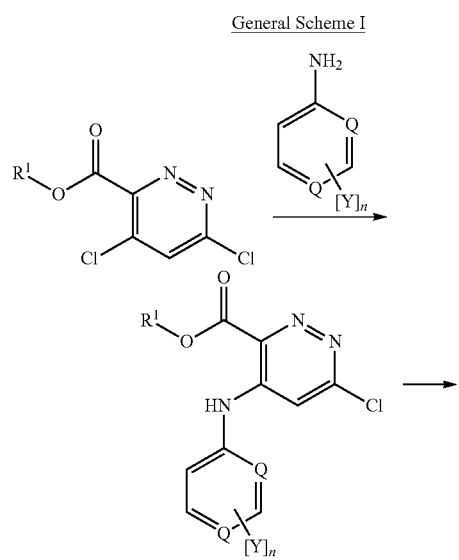

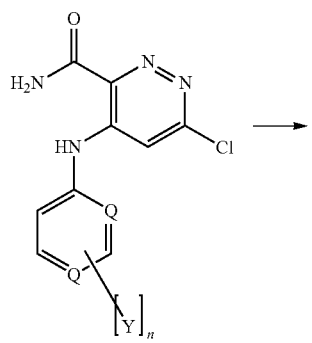

-continued

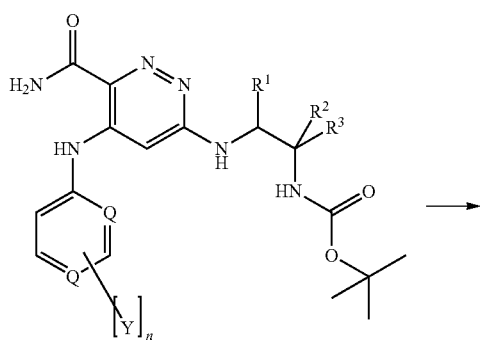

27
-continued
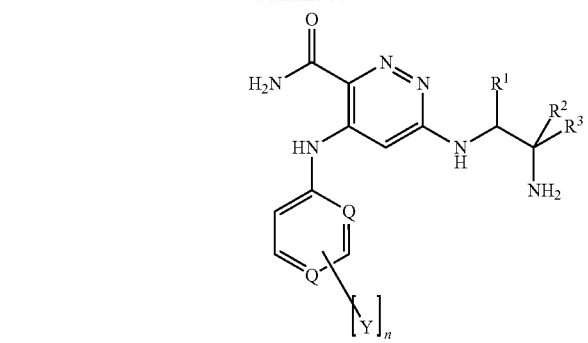
General Scheme II
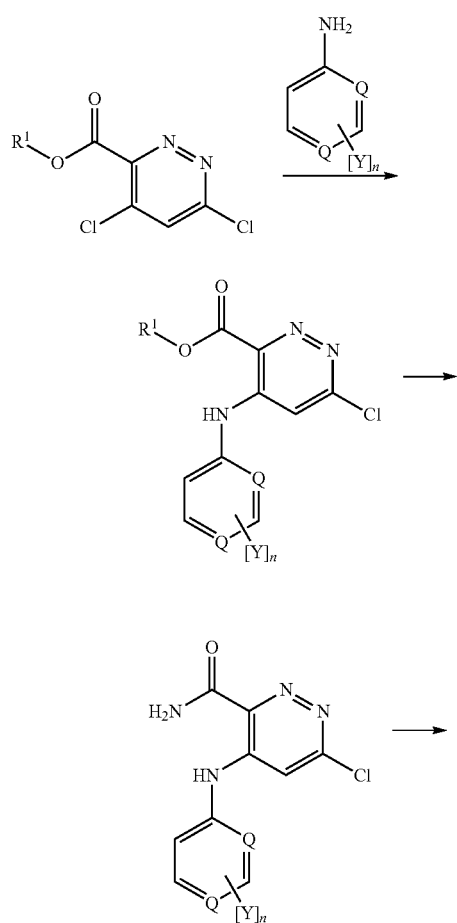
28
General Scheme III
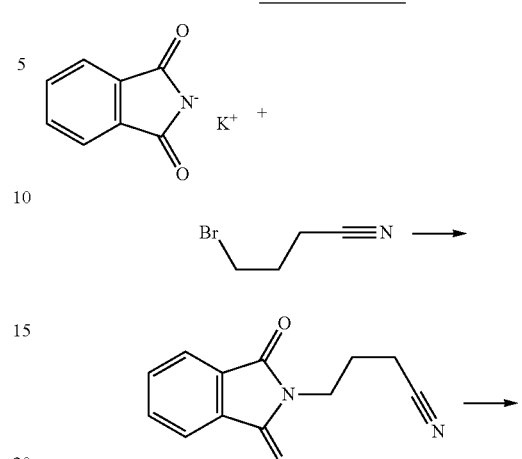

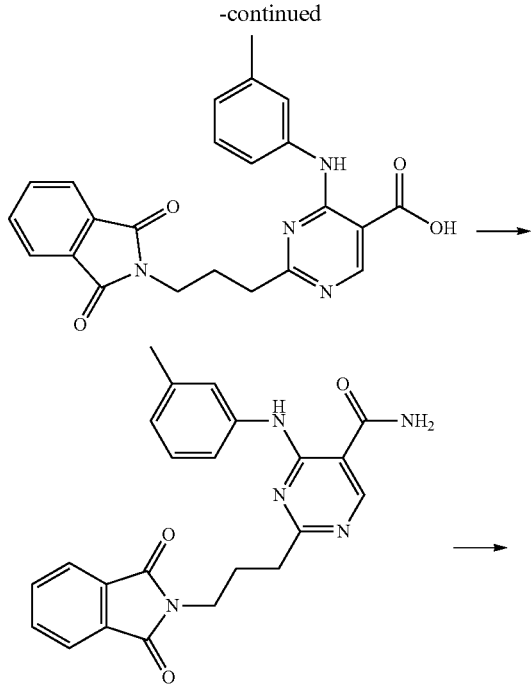

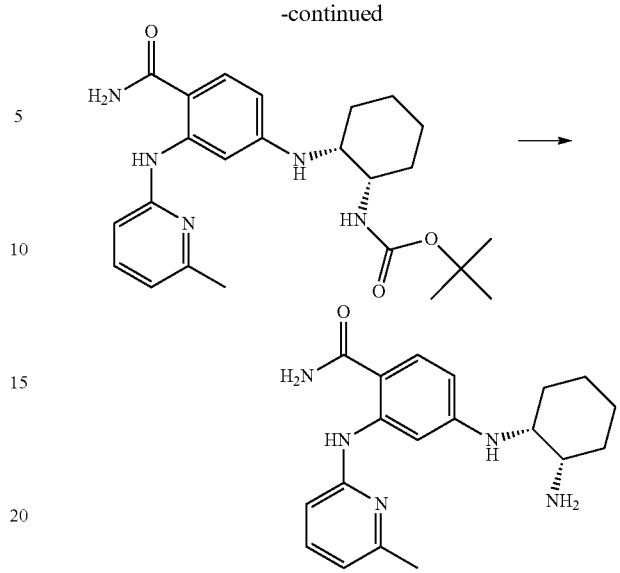

General Scheme V

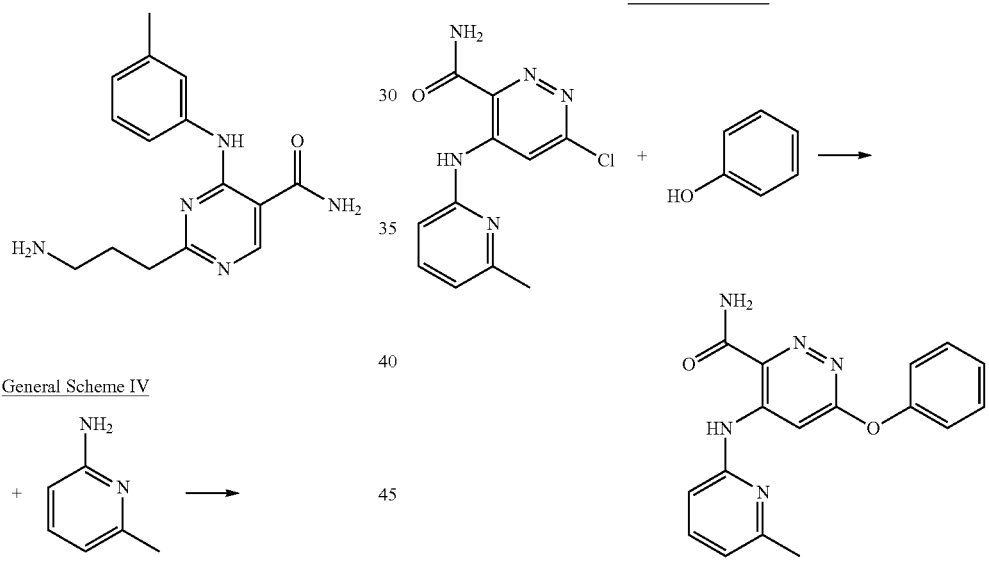

General Scheme IV

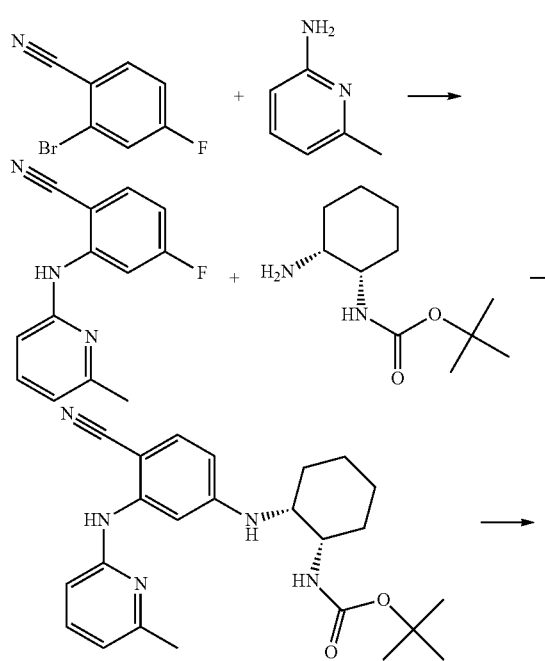

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth;

pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, pre-determined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid. Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 h.

Indications and Methods of Treatment

The compounds described herein are kinase inhibitors, in particular SYK inhibitors. These inhibitors can be useful for treating one or more diseases responsive to kinase inhibition, including diseases responsive to SYK inhibition and/or inhibition of B-cell proliferation, in mammals. Without wishing to be bound to any particular theory, it is believed that the interaction of the compounds of the invention with SYK results in the inhibition of SYK activity and thus in the pharmaceutical utility of these compounds. Accordingly, the invention includes a method of treating a mammal, for instance a human, having a disease responsive to inhibition of SYK activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to SYK include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride (BOC$_2$O), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether (Et$_2$O), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), MeSO$_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) (Pd(dppf)Cl$_2$), palladium(II) acetate (Pd(OAc)$_2$), tris(dibenzylideneacetone)dipalladium(0) (Pd$_2$(dba)$_3$), pyridinium dichromate (PDC), phenyl (Ph), propyl (Pr), isopropyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or Et$_3$N), 2,2,6,6-tetramethylpiperidine 1-oxyl (TEMPO), triflate or CF$_3$SO$_2$— (TO, trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$Si (TMS), p-toluenesulfonic acid monohydrate (TsOH or pTsOH), 4-Me-C$_6$H$_4$SO$_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions.

Unless otherwise stated, all temperatures including melting points (i.e., MP) are in degrees Celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The preceding abbreviations may be used in the Preparations and Examples. All names were generated using Autonom or ChemDraw.

The following preparations and examples are given to enable those skilled in the art to more clearly understand and to practice the present invention. They should not be considered as limiting the scope of the invention, but merely as being illustrative and representative thereof.

PREPARATIVE EXAMPLES

Example 1

4-(6-Methyl-pyridin-2-ylamino)-6-phenoxy-pyridazine-3-carboxamide

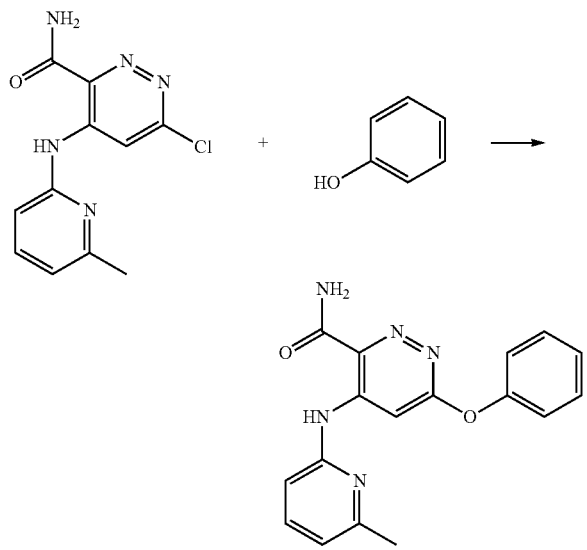

A pressure tube with stir bar was charged with 6-chloro-4-(6-methylpyridin-2-ylamino)pyridazine-3-carboxamide (23.9 mg, 0.0901 mmol), phenol (600 mg, 6 mmol), and potassium hydroxide (98.3 mg, 1.75 mmol). The solid mixture was heated to 120° C., and became a yellow solution, which was stirred at 120° C. for 22 h. After cooling to room temperature, the resulting dark orange solid was partitioned between 10 mL of a 10% aqueous sodium hydroxide solution and 10 mL of dichloromethane. The organic layer was washed with 10 mL of a 10% aqueous sodium hydroxide solution, dried over $Na_2SO_4$, filtered and concentrated to a yellow oily solid. Purification by chromatography (12 g silica gel column from Thompson, eluting from 20% ethyl acetate/hexanes to 40% ethyl acetate/hexanes) afforded 4-(6-methyl-pyridn-2-ylamino)-6-phenoxy-pyridazine-3-carboxamide (11.5 mg, 40%) as a white solid. $^1$H NMR (300 MHz, DMSO-$d_6$) δ ppm 2.22 (s, 3H) 6.83 (dd, J=14.73, 7.93 Hz, 2H) 7.20-7.38 (m, 3H) 7.49 (d, J=7.93 Hz, 2H) 7.62 (s, 1H) 8.02 (br. s., 1H) 8.57-8.65 (m, 1H) 8.65-8.75 (m, 1H) 11.55-12.17 (m, 1H). MS (EI/CI) m/z: 322.1 [M+H].

Example 2

6-(3-Cyanophenoxy)-4-(6-methyl-pyridin-2-ylamino)-pyridazine-3-carboxamide

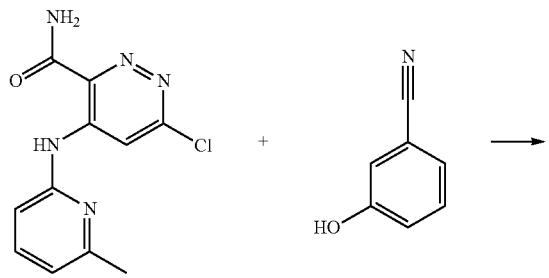

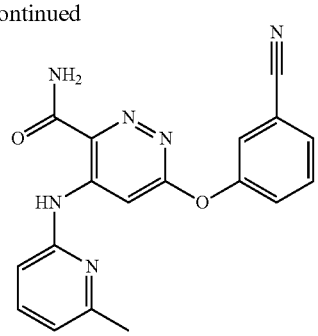

A pressure tube with stir bar was charged with 3-hydroxybenzonitrile (11.8 mg, 0.0991 mmol), 1 mL of tetrahydrofuran and 60% sodium hydride in mineral oil (4 mg, 0.1 mmol). The bubbling, colorless solution was stirred for 5 min. 6-Chloro-4-(6-methylpyridin-2-ylamino)pyridazine-3-carboxamide (20.4 mg, 0.0774 mmol) was added, the tube was sealed and the yellow mixture was stirred at 70° C. overnight then allowed to cool. LC/MS analysis indicated minimal reaction had occurred. Solvent was removed by blowing a stream of nitrogen over the solution, then 1 mL of N,N-dimethylformamide was added. The tube was again sealed and the yellow solution stirred at 70° C. for 3 h, then 90° C. for 3 d. The solution was transferred to a flask, rinsing with diethyl ether, and concentrated to an off-white solid. Purification by chromatography (12 g silica gel column from Thompson, eluting from hexanes to 50% ethyl acetate/hexanes), afforded 6-(3-cyanophenoxy)-4-(6-methyl-pyridn-2-ylamino)-pyridazine-3-carboxamide (13.9 mg, 52%) as a white solid. $^1$H NMR (300 MHz, DMSO-$d_6$) δ ppm 2.33 (s, 3H) 6.81-6.94 (m, 2H) 7.60-7.82 (m, 4H) 7.88-7.94 (m, 1H) 8.02-8.10 (m, 1H) 8.63-8.76 (m, 2H) 11.83-11.98 (m, 1H). MS (EI/CI) m/z: 347.0 [M+H].

Example 3

6-[3-(1-Amino-1-methyl-ethyl)-phenoxy]-4-(6-methyl-pyridin-2-ylamino)-pyridazine-3-carboxamide

Step 1

(S)—N-(1-(3-(Benzyloxy)phenyl)ethylidene)-2-methylpropane-2-sulfinamide

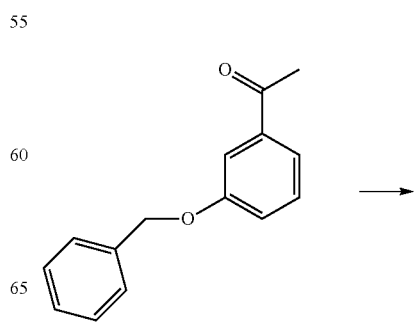

-continued

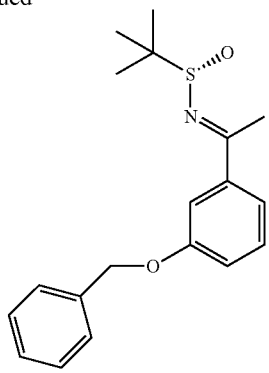

A pressure tube with stir bar was charged with 1-(3-(benzyloxy)phenyl)ethanone (701 mg, 3.10 mmol), 7 mL of tetrahydrofuran, S-2-methylpropane-2-sulfinamide (376 mg, 3.10 mmol) and tetraethoxytitanium (1.3 mL, 6.2 mmol). The pale yellow solution stirred at 75° C. for 3 d, then allowed to cool. Methanol (1 mL) was slowly added, then with rapid stirring 7 mL of a saturated aqueous sodium chloride solution was added. Precipitate was removed by filtration through Celite 545, rinsing with 20 mL of ethyl acetate. The filtrate was washed with 10 mL of a saturated aqueous sodium chloride solution, and the aqueous layer was extracted with 10 mL of ethyl acetate. The combined organic layers were dried over Na$_2$SO$_4$, filtered and concentrated to a yellow oil. Purification by chromatography (12 g silica gel column from Thompson, eluting from hexanes to 33% ethyl acetate/hexanes), afforded (S)—N-(1-(3-(benzyloxy)phenyl)ethylidene)-2-methylpropane-2-sulfinamide (383 mg, 38%) as a yellow viscous oil. $^1$H NMR (300 MHz, CHLOROFORM-d) δ ppm 1.24-1.38 (m, 9H) 2.75 (s, 3H) 5.12 (s, 2H) 7.05-7.17 (m, 1H) 7.29-7.60 (m, 8H). MS (EI/CI) m/z: 330.0 [M+H].

Step 2

2-(3-(Benzyloxy)phenyl)propan-2-amine

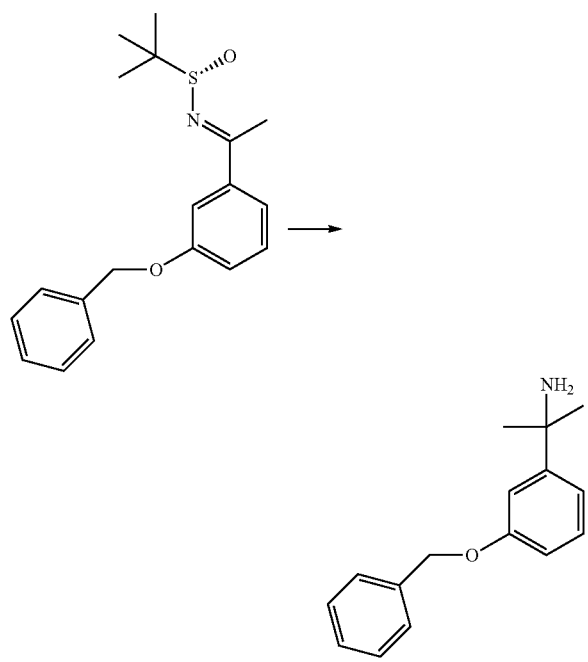

A mixture of (S)—N-(1-(3-(benzyloxy)phenyl)ethylidene)-2-methylpropane-2-sulfinamide (348 mg, 1.06 mmol), 4 mL of toluene, and a 2.0 M trimethylaluminum in heptane solution (0.60 mL, 1.2 mmol) at −78° C. was treated with a 3.0 M methylmagnesium bromide in diethyl ether solution (0.80 mL, 2.4 mmol) over 30 sec. White precipitate forms. The mixture was stirred 16 h, allowing to warm to room temperature. To the resulting pale yellow solution was slowly added 10 mL of a saturated aqueous sodium bicarbonate solution (much bubbling and formation of white precipitate) and the mixture was stirred 5 min. Solids were removed by filtration, rinsing with 15 mL of dichloromethane. The filtrate layers were separated, and the bottom pale yellow organic layer was concentrated in a flask to 344 mg of yellow oil mixed with white solid. To the flask was added a stir bar, 10 mL of methanol, and 1 mL of a 4.0 M hydrochloric acid in dioxane solution. The yellow solution was stirred 3.5 h, then concentrated to a yellow film, which was partitioned between 10 mL of dichloromethane and 10 mL of a 10% aqueous sodium hydroxide solution. The aqueous layer was extracted with 10 mL of dichloromethane. The combined organic layers were dried over Na$_2$SO$_4$, filtered and concentrated to a pale yellow oil. Purification by chromatography (12 g silica gel column from Thompson, eluting from ethyl acetate to 10% methanol/ethyl acetate) afforded slightly impure 2-(3-(benzyloxy)phenyl)propan-2-amine (148 mg, 58%) as a very pale yellow oil, which was used without further purification. $^1$H NMR (300 MHz, CHLOROFORM-d) δ ppm 1.43-1.52 (m, 6H) 1.62 (s, 2H) 5.01-5.14 (m, 2H) 6.77-6.91 (m, 1H) 7.04-7.60 (m, 8H).

Step 3

3-(2-Aminopropan-2-yl)phenol

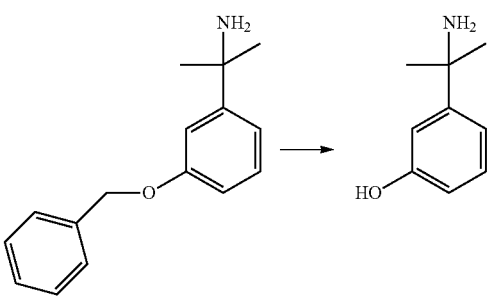 [SMILES: CC(C)(N)c1cccc(OCc2ccccc2)c1 ; CC(C)(N)c1cccc(O)c1]

To a flask containing a stir bar, vacuum inlet, balloon filled with hydrogen, 10% Pd/C (0.1460 g), and 2 mL of tetrahydrofuran was added 2-(3-(benzyloxy)phenyl)propan-2-amine (148 mg g, 0.615 mmol) in a total of 3 mL of tetrahydrofuran. The flask was evacuated and filled with hydrogen, and the black suspension was stirred 18 h under an atmosphere of hydrogen. The suspension was filtered through Celite 545, rinsing well with diethyl ether, and the filtrate was concentrated to crude 3-(2-aminopropan-2-yl)phenol (88.6 mg, 95%) as a tan solid, which was used in the next step without purification. $^1$H NMR (300 MHz, METHANOL-d$_4$) δ ppm 1.36-1.59 (m, 6H) 6.57-6.76 (m, 1H) 6.81-7.05 (m, 2H) 7.07-7.23 (m, 1H). MS (EI/CI) m/z: 135.2 [M−NH$_2$].

Step 4

6-[3-(1-Amino-1-methyl-ethyl)-phenoxy)-4-(6-methyl-pyridin-2-ylamino)-pyridazine-3-carboxamide

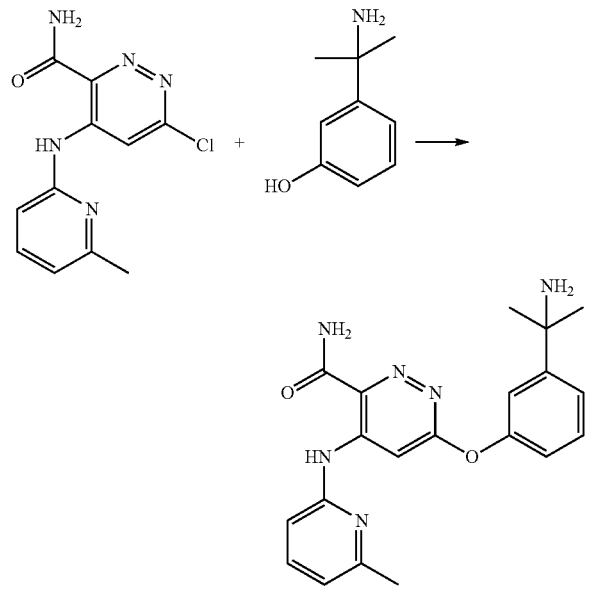

The above-prepared crude 3-(2-aminopropan-2-yl)phenol (20.7 mg, 0.130 mmol) was dissolved in 1 mL of N,N-dimethylformamide and the pale orange solution was chilled to 0-5° C. To the solution was added 60% sodium hydride in mineral oil (7 mg, 0.2 mmol), then more 3-(2-aminopropan-2-yl)phenol (6.3 mg, 0.042 mmol). The mixture was stirred at ambient temperature for 10 min. 6-Chloro-4-(6-methyl-pyridin-2-ylamino)pyridazine-3-carboxamide (30.8 mg, 0.117 mmol) was added, and the yellow mixture was stirred at 90° C. for 3 d. The resulting yellow solution was concentrated to a yellow residue. Purification by chromatography (12 g silica gel column from Thompson, eluting from ethyl acetate to 10% methanol/ethyl acetate), afforded 6-[3-(1-amino-1-methyl-ethyl)-phenoxy)-4-(6-methyl-pyridn-2-ylamino)-pyridazine-3-carboxamide (18.0 mg, 41%) as an off-white solid. $^1$H NMR (300 MHz, DMSO-d$_6$) δ ppm 1.30-1.41 (m, 6H) 2.21 (s, 3H) 6.83 (dd, J=14.35, 7.93 Hz, 2H) 7.07 (d, J=7.55 Hz, 1H) 7.29-7.50 (m, 3H) 7.61 (t, J=7.74 Hz, 1H) 8.01 (br. s., 1H) 8.57-8.64 (m, 1H) 8.68 (br. s., 1H) 11.79-11.92 (m, 1H). MS (EI/CI) m/z: 347.0 [M+H].

Example 4

6-[3-(3-Fluoro-phenoxy)-4-(6-methyl-pyridin-2-ylamino)-pyridazine-3-carboxamide

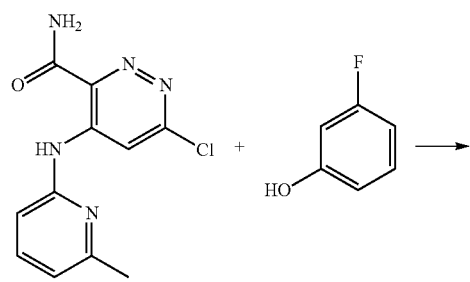

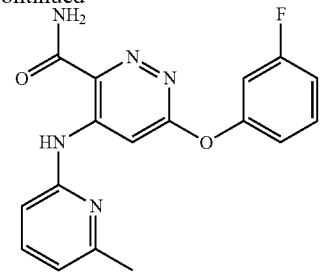

A solution of 3-fluorophenol (0.021 mL, 0.23 mmol) in 1 mL of N,N-dimethylformamide was treated with 60% sodium hydride in mineral oil (9 mg, 0.2 mmol). The yellow solution was stirred for 5 min., then treated with 6-chloro-4-(6-methylpyridin-2-ylamino)pyridazine-3-carboxamide (21.1 mg, 0.0800 mmol) and the yellow solution was stirred at 90° C. for 2 d. The solution was concentrated to a yellow solid. Purification by chromatography (12 g silica gel column from Thompson, eluting from hexanes to 50% ethyl acetate/hexanes), afforded 6-[3-(3-fluoro-phenoxy)-4-(6-methyl-pyridn-2-ylamino)-pyridazine-3-carboxamide (22.2 mg, 82%) as a white solid. $^1$H NMR (300 MHz, DMSO-d$_6$) δ ppm 2.28 (s, 3H) 6.86 (dd, J=15.49, 7.55 Hz, 2H) 7.11-7.22 (m, 2H) 7.28 (d, J=10.20 Hz, 1H) 7.53 (q, J=7.93 Hz, 1H) 7.64 (t, J=7.74 Hz, 1H) 8.04 (br. s., 1H) 8.67 (s, 1H) 8.71 (br. s., 1H) 11.84-11.92 (m, 1H). MS (EI/CI) m/z: 340.1 [M+H].

Example 5

4-(6-Methyl-pyridin-2-ylamino)-6-(pyridine-3-yloxy)-pyridazine-3-carboxamide

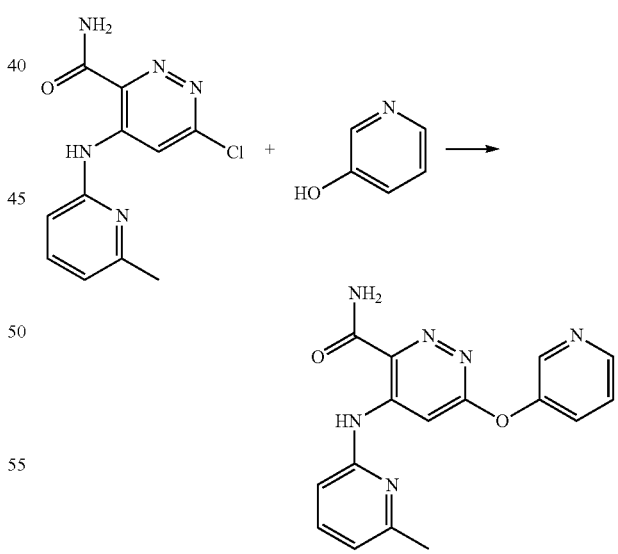

A solution of 3-hydroxypyridine (24.2 mg, 0.254 mmol) in 1 mL of N,N-dimethylformamide at 0-5° C. was treated with 60% sodium hydride in mineral oil (9.5 mg, 0.24 mmol), and the colorless mixture was stirred at 0-5° C. for 30 min. The resulting pale yellow solution was treated with 6-chloro-4-(6-methylpyridin-2-ylamino)pyridazine-3-carboxamide (21.5 mg, 0.0815 mmol), and the bright yellow solution was stirred at 110° C. for 17 h. The orange solution was concentrated to an orange residue. Purification by chromatography (12 g silica gel column from Thompson, eluting from hexanes to 66% ethyl acetate/hexanes), afforded 4-(6-methyl-pyridin-2-ylamino)-6-(pyridine-3-yloxy)-pyridazine-3-carboxamide (16.8 mg, 64%) as an off-white solid, 90% pure by LC/MS analysis. $^1$H NMR (300 MHz, DMSO-d$_6$) δ ppm 2.33 (s, 3H) 6.88 (dd, J=16.05, 7.74 Hz, 2H) 7.54 (dd, J=8.31, 4.91 Hz, 1H) 7.65 (t, J=7.74 Hz, 1H) 7.80 (d, J=7.93 Hz, 1H) 8.05 (br. s., 1H) 8.51 (d, J=4.16 Hz, 1H) 8.60 (d, J=2.64 Hz, 1H) 8.70 (s, 2H) 11.84-11.96 (m, 1H). MS (EI/CI) m/z: 323.0 [M+H].

Example 6

6-(3-Cyano-phenoxy)-4-(6-methyl-pyridin-2-ylamino)-pyridazine-3-carboxamide

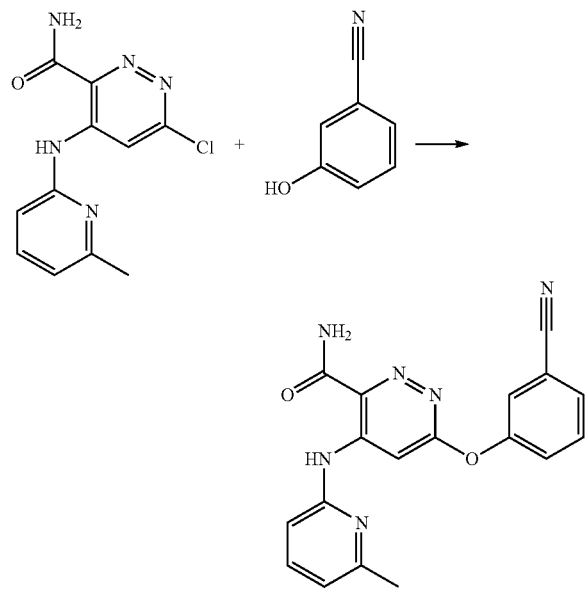

A solution of 3-hydroxybenzonitrile (27.7 mg, 0.233 mmol) in 1 mL of N,N-dimethylformamide at 0-5° C. was treated with 60% sodium hydride in mineral oil (9.5 mg, 0.24 mmol) and the mixture was stirred at 0-5° C. for 25 min. The mixture was then treated with 6-chloro-4-(6-methylpyridin-2-ylamino)pyridazine-3-carboxamide (20.7 mg, 0.0785 mmol) and the yellow mixture was stirred at 110° C. for 15 h, then at 130° C. for 48 h. The orange solution was concentrated to a yellow-stained off-white solid. Purification by chromatography (12 g silica gel column from Thompson, eluting from hexanes to 50% ethyl acetate/hexanes), afforded 6-(3-cyano-phenoxy)-4-(6-methyl-pyridin-2-ylamino)-pyridazine-3-carboxamide (14.0 mg, 52%) as a white solid. $^1$H NMR (300 MHz, DMSO-d$_6$) δ ppm 2.38 (s, 3H) 6.90 (dd, J=15.68, 7.74 Hz, 2H) 7.45-7.60 (m, 2H) 7.62-7.73 (m, 1H) 7.77-7.89 (m, 1H) 7.95-8.03 (m, 1H) 8.08 (br. s., 1H) 8.71 (br. s., 1H) 8.77 (s, 1H) 11.90-11.99 (m, 1H). MS (EI/CI) m/z: 347.0 [M+H].

Example 7

6-(3-Ethyl-phenoxy)-4-(6-methyl-pyridin-2-ylamino)-pyridazine-3-carboxamide

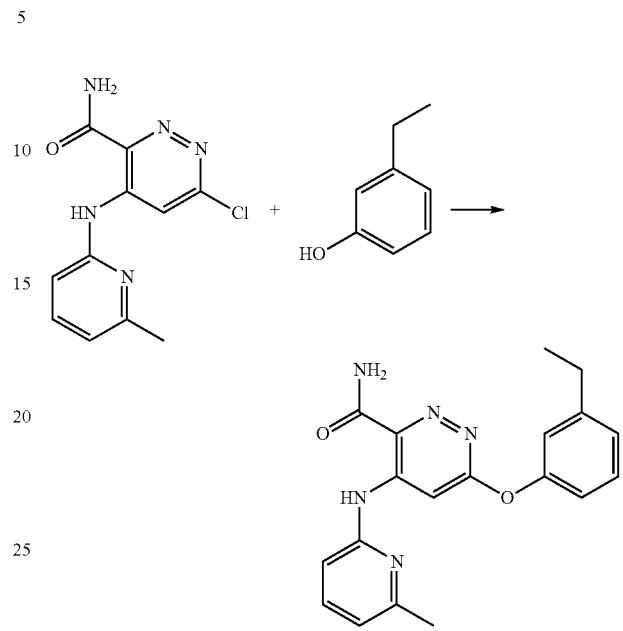

A solution of 2-ethylphenol (0.030 mL, 0.26 mmol) in 1 mL of N,N-dimethylformamide at 0-5° C. was treated with 60% sodium hydride in mineral oil (10 mg, 0.25 mmol) and the mixture was stirred at 0-5° C. for 10 min. The yellow solution was then treated with 6-chloro-4-(6-methylpyridin-2-ylamino)pyridazine-3-carboxamide (20.4 mg, 0.0774 mmol) and the yellow solution was stirred at 130° C. for 23 h, during which time the solution ran dry leaving an orange residue. Purification by chromatography (12 g silica gel column from Thompson, eluting from hexanes to 50% ethyl acetate/hexanes), afforded 6-(3-ethyl-phenoxy)-4-(6-methyl-pyridin-2-ylamino)-pyridazine-3-carboxamide (15.5 mg, 57%) as an off-white solid. $^1$H NMR (300 MHz, DMSO-d$_6$) δ ppm 1.11 (t, J=7.55 Hz, 3H) 2.20 (s, 3H) 6.82 (dd, J=14.73, 7.93 Hz, 2H) 7.12-7.21 (m, 1H) 7.22-7.35 (m, 2H) 7.37-7.48 (m, 1H) 7.61 (t, J=7.74 Hz, 1H) 8.01 (br. s., 1H) 8.55 (s, 1H) 8.68 (br. s., 1H) 11.78-11.89 (m, 1H). In the NMR spectrum, a multiplet presumably corresponding to the ethyl methylene group (2H) is buried underneath the DMSO solvent peak. MS (EI/CI) m/z: 350.1 [M+H].

Example 8

4-(6-Methyl-pyridin-2-ylamino)-6-m-tolyloxy-pyridazine-3-carboxamide

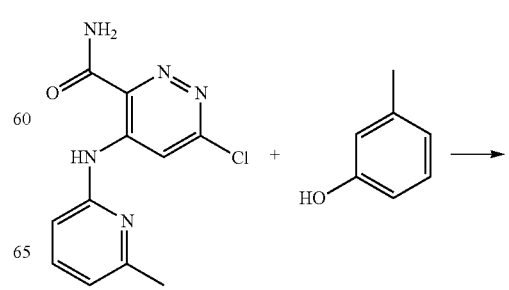

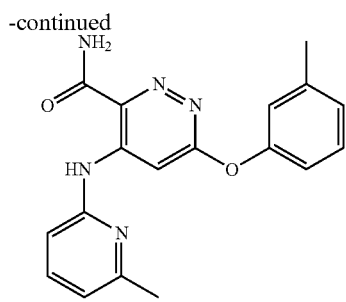

A solution of o-cresol (0.024 mL, 0.23 mmol) in 1 mL of N,N-dimethylformamide at 0-5° C. was treated with 60% sodium hydride in mineral oil (10 mg, 0.25 mmol) and the mixture was stirred at 0-5° C. for 35 min. The yellow mixture was then treated with 6-chloro-4-(6-methylpyridin-2-ylamino)pyridazine-3-carboxamide (20.0 mg, 0.0758 mmol) and the yellow mixture was stirred at 130° C. for 18 h. The yellow solution was concentrated to an orange residue. Purification by chromatography (12 g silica gel column from Thompson, eluting from hexanes to 50% ethyl acetate/hexanes), afforded 4-(6-methyl-pyridin-2-ylamino)-6-m-tolyloxy-pyridazine-3-carboxamide (14.4 mg, 57%) as an off-white solid. $^1$H NMR (300 MHz, DMSO-$d_6$) δ ppm 2.14 (s, 3H) 2.22 (s, 3H) 6.83 (dd, J=15.68, 7.74 Hz, 2H) 7.15-7.43 (m, 4H) 7.61 (t, J=7.74 Hz, 1H) 8.01 (br. s., 1H) 8.53 (s, 1H) 8.68 (br. s., 1H) 11.78-11.89 (m, 1H). MS (EI/CI) m/z: 336.0 [M+H].

Example 9

6-(4-Chloro-2-cyano-phenoxy)-4-(6-methyl-pyridin-2-ylamino)-pyridazine-3-carboxamide

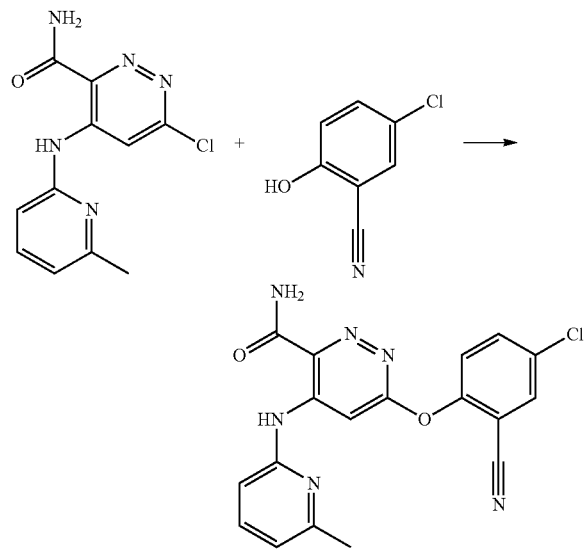

A solution of 5-chloro-2-hydroxybenzonitrile (52.9 mg, 0.344 mmol) in 1 mL of N,N-dimethylformamide at 0-5° C. was treated with 60% sodium hydride in mineral oil (14 mg, 0.35 mmol) and the colorless solution was stirred at 0-5° C. for 30 min. The resulting yellow mixture was then treated with 6-chloro-4-(6-methylpyridin-2-ylamino)pyridazine-3-carboxamide (32.3 mg, 0.122 mmol) and the yellow mixture was stirred at 130° C. for 3 d. The yellow solution was concentrated to a pale yellow solid. Purification by chromatography (12 g silica gel column from Thompson, eluting from hexanes to 50% ethyl acetate/hexanes), followed by trituration of the product with methanol, afforded 6-(4-chloro-2-cyano-phenoxy)-4-(6-methyl-pyridin-2-ylamino)-pyridazine-3-carboxamide (15.2 mg, 33%) as a pale yellow solid, >90% pure by NMR analysis. $^1$H NMR (300 MHz, DMSO-$d_6$) δ ppm 2.41 (s, 3H) 6.91 (dd, J=17.00, 7.55 Hz, 2H) 7.56-7.72 (m, 2H) 7.91 (dd, J=8.69, 2.64 Hz, 1H) 8.10 (br. s., 1H) 8.21 (d, J=2.64 Hz, 1H) 8.71 (br. s., 1H) 8.77-8.82 (m, 1H) 11.90-12.01 (m, 1H). MS (EI/CI) m/z: 381.0 [M+H].

Example 10

6-(3-Cyclopropyl-phenoxy)-4-(6-methyl-pyridin-2-ylamino)-pyridazine-3-carboxamide

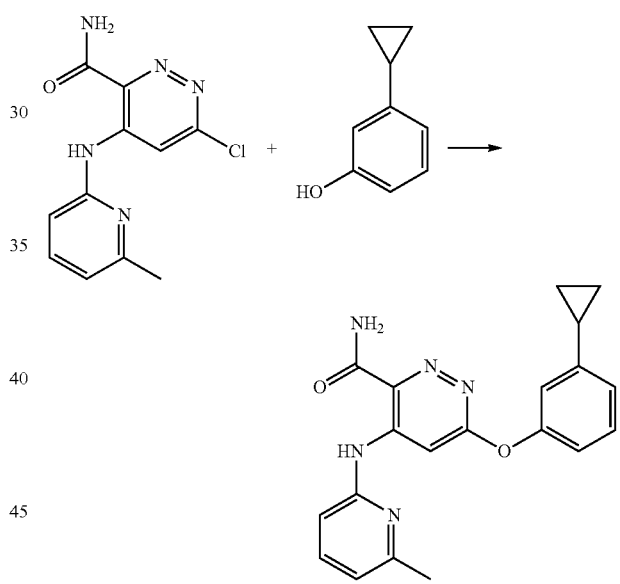

A solution of 2-cyclopropylphenol (34.7 mg, 0.259 mmol) in 1 mL of N,N-dimethylformamide at 0-5° C. was treated with 60% sodium hydride in mineral oil (10 mg, 0.25 mmol) and the pale yellow solution was stirred at 0-5° C. for 45 min. The solution was then treated with 6-chloro-4-(6-methylpyridin-2-ylamino)pyridazine-3-carboxamide (20.4 mg, 0.0774 mmol) and the yellow mixture was stirred at 130° C. for 22 h. The yellow solution was concentrated to a dark yellow residue. Purification by chromatography (12 g silica gel column from Thompson, eluting from hexanes to 50% ethyl acetate/hexanes) afforded 6-(3-cyclopropyl-phenoxy)-4-(6-methyl-pyridin-2-ylamino)-pyridazine-3-carboxamide (15.5 mg, 55%) as an off-white solid. $^1$H NMR (300 MHz, DMSO-$d_6$) δ ppm 0.58-0.69 (m, 2H) 0.72-0.87 (m, 2H) 1.78-1.93 (m, 1H) 2.17 (s, 3H) 6.82 (dd, J=13.60, 7.93 Hz, 2H) 7.03-7.12 (m, 1H) 7.14-7.32 (m, 3H) 7.61 (t, J=7.74 Hz, 1H) 8.00 (br. s., 1H) 8.55 (s, 1H) 8.68 (br. s., 1H) 11.80-11.86 (m, 1H). MS (EI/CI) m/z: 362.0 [M+H].

Example 11

4-(6-Cyclopropyl-pyridin-2-ylamino)-6-oxo-1,6-dihydro-pyridazine-3-carboxylic acid amide Step 1

Ethyl 6-chloro-4-(6-cyclopropylpyridin-2-ylamino)pyridazine-3-carboxylate

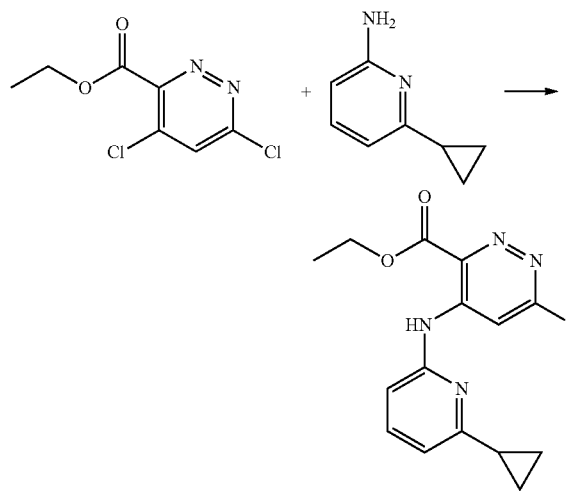

A pressure tube charged with ethyl 4,6-dichloropyridazine-3-carboxylate (300 mg, 1.36 mmol), 6-cyclopropylpyridin-2-amine (273 mg, 2.04 mmol), and acetonitrile (8 mL) was heated at 140° C. for 20 h. After cooling to room temperature, the mixture was concentrated in vacuo and the residue obtained was purified by chromatography (silica, 50 μm, 80 g, Analogix, 0 to 10% acetone in dichloromethane, 20 min) to give ethyl 6-chloro-4-(6-cyclopropylpyridin-2-ylamino)pyridazine-3-carboxylate (145 mg, 34%) as a yellow solid. $^1$H NMR (400 MHz, CHLOROFORM-d) δ ppm 10.64 (br. s., 1H), 9.39 (s, 1H), 7.63 (t, J=7.83 Hz, 1H), 6.94 (d, J=7.58 Hz, 1H), 6.78 (d, J=8.08 Hz, 1H), 4.12 (s, 3H), 1.99-2.10 (m, 1H), 1.06-1.12 (m, 4H). LCMS (EI/CI) m/z: 319 [M+H].

Step 2

6-Chloro-4-(6-cyclopropylpyridin-2-ylamino)pyridazine-3-carboxamide

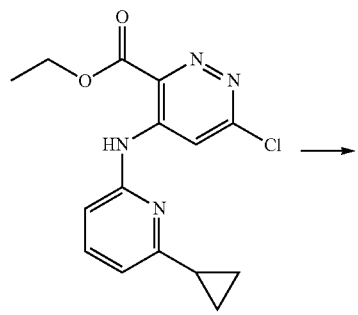

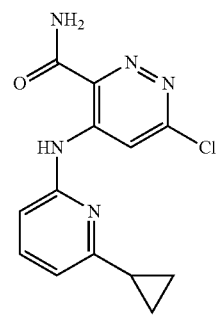

Ethyl 6-chloro-4-(6-cyclopropylpyridin-2-ylamino)pyridazine-3-carboxylate (140 mg, 439 μmol) and ammonia (7M in methanol, 9.44 g, 12 mL, 84.0 mmol) were heated at 50° C. in a sealed tube for 21 h. After cooling to room temperature, concentration in vacuo gave 6-chloro-4-(6-cyclopropylpyridin-2-ylamino)pyridazine-3-carboxamide (112 mg, 88%) as a yellow solid. $^1$H NMR (300 MHz, CHLOROFORM-d) δ ppm 11.51 (br. s., 1H), 9.16 (s, 1H), 8.16 (br. s., 1H), 7.52 (t, J=7.74 Hz, 1H), 6.86-6.96 (m, 1H), 6.68 (d, J=7.93 Hz, 1H), 5.65 (br. s., 1H), 1.99-2.10 (m, 1H), 1.06-1.12 (m, 4H). LCMS (EI/CI) m/z: 290 [M+H]. The crude product was used directly in the next step without further purification.

Step 3

4-(6-Cyclopropyl-pyridin-2-ylamino)-6-oxo-1,6-dihydro-pyridazine-3-carboxylic acid amide

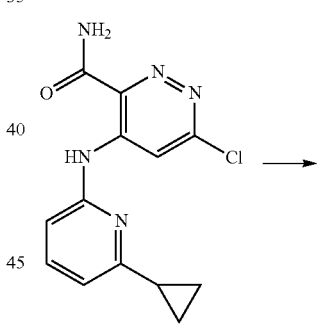

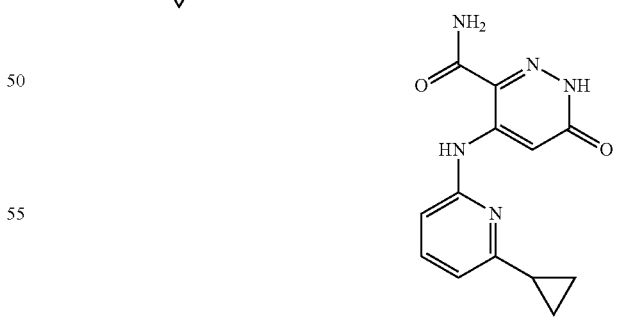

6-Chloro-4-(6-cyclopropylpyridin-2-ylamino)pyridazine-3-carboxamide (50 mg, 173 μmol), acetic acid (2.1 g, 2.00 mL, 34.9 mmol), sodium acetate (21.2 mg, 259 μmol) and water (600 mg, 0.6 mL, 33.3 mmol) were placed in a microwave vial and heated in a microwave reactor at 140° C. for 2 h. The crude mixture was diluted with dichloromethane and MeOH then absorbed on silica gel and purified by chromatography (silica 20-45 μm, 12 g, Versaflash from Supelco, 10 to 60% of a 24:2.4:0.4 dichloromethane:methanol:NH$_4$OH solution in dichloromethane) to give 4-(6-cyclopropyl-pyridin-2-ylamino)-6-oxo-1,6-dihydropyridazine-3-carboxylic acid amide (30 mg, 64%) as a white solid. $^1$H NMR (400 MHz, DMSO-d$_6$) δ ppm 12.95 (s, 1H), 11.42 (s, 1H), 8.13 (s, 1H), 7.94 (s, 1H), 7.78 (s, 1H), 7.58 (t, J=7.71 Hz, 1H), 6.97 (d, J=7.33 Hz, 1H), 6.70 (d, J=8.08 Hz, 1H), 2.04-2.17 (m, 1H), 1.24 (s, 1H), 0.87-1.13 (m, 5H).

Example 12

6-(1-Amino-4-methylpentan-2-ylamino)-4-(6-tert-butylpyridin-2-ylamino)pyridazine-3-carboxamide Step 1

Methyl 4-(6-tert-butylpyridin-2-ylamino)-6-chloropyridazine-3-carboxylate

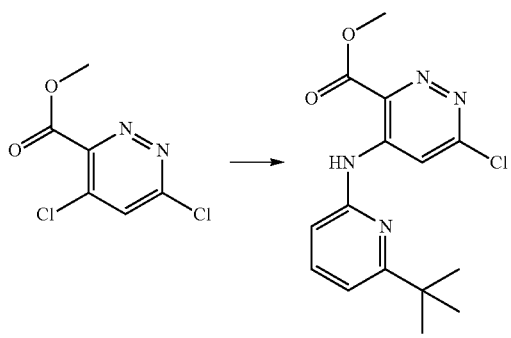 [SMILES: COC(=O)c1nnc(Cl)cc1Cl ; COC(=O)c1nnc(Cl)cc1Nc1cccc(C(C)(C)C)n1]

A mixture of methyl 4,6-dichloropyridazine-3-carboxylate (0.69 g, 3.33 mmol) and 6-tert-butylpyridin-2-amine (1.00 g, 6.67 mmol) was dissolved in acetonitrile (3 mL) and heated at 130° C. for 14 h. The dark brown mixture was cooled, concentrated onto silica, and purified by chromatography (silica, 80 g, 0 to 20% acetone in dichloromethane, 40 min) to give methyl 4-(6-tert-butylpyridin-2-ylamino)-6-chloropyridazine-3-carboxylate (372 mg, 1.16 mmol, 35%) as a yellow solid. MS (EI/CI) m/z: 321.0 [M+H].

Step 2

4-(6-tert-Butylpyridin-2-ylamino)-6-chloropyridazine-3-carboxamide

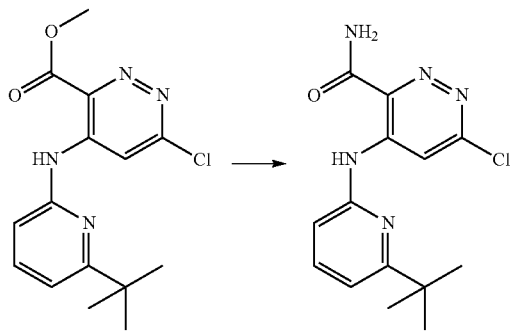 [SMILES: COC(=O)c1nnc(Cl)cc1Nc1cccc(C(C)(C)C)n1 ; CC(C)(C)c1cccc(Nc2cc(Cl)nnc2C(N)=O)n1]

Methyl 4-(6-tert-butylpyridin-2-ylamino)-6-chloropyridazine-3-carboxylate (360 mg, 1.12 mmol) was suspended in 7N ammonia in methanol (12 mL, 84.0 mmol) and stirred at room temperature for 16 h. The mixture was concentrated in vacuo to give 4-(6-tert-butylpyridin-2-ylamino)-6-chloropyridazine-3-carboxamide (317 mg, 1.03 mmol, 92%) as a yellow powder. MS (EI/CI) m/z: 306.0 [M+H]. This material was used directly in the next step without further purification.

Step 3 tert-Butyl 2-(5-(6-tert-butylpyridin-2-ylamino)-6-carbamoylpyridazin-3-ylamino)-4-methylpentylcarbamate

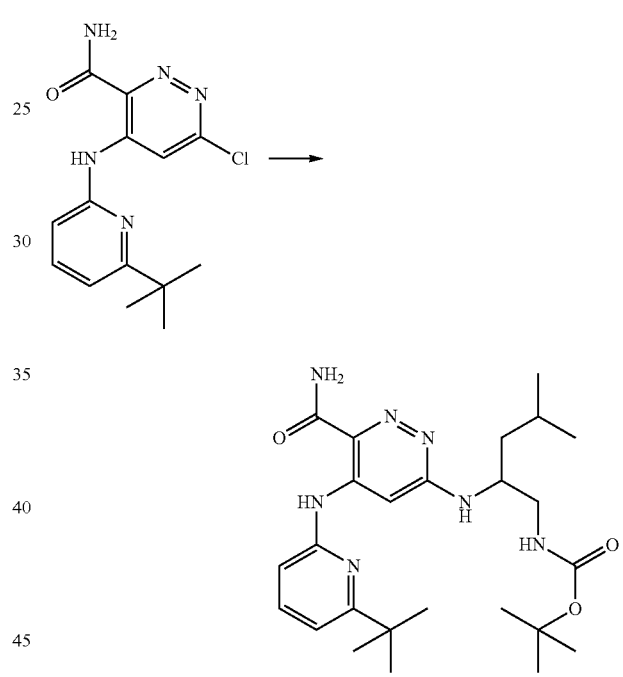

A stirred solution of 4-(6-tert-butylpyridin-2-ylamino)-6-chloropyridazine-3-carboxamide (110 mg, 360 μmol) and tert-butyl 2-amino-4-methylpentylcarbamate (156 mg, 720 μmol) in N-methyl-2-pyrrolidinone (1.5 mL) was heated at 140° C. for 8 h, then 120° C. for 72 h. Additional tert-butyl 2-amino-4-methylpentylcarbamate (156 mg, 720 μmol) was added and then the mixture heated at 140° C. for 6 h. A final portion of tert-butyl 2-amino-4-methylpentylcarbamate (156 mg, 720 μmol) was added and the mixture stirred at 140° C. for an additional 14 h. The resulting pale brown solution was concentrated in vacuo to an orange oil and then purified by chromatography (11 g spherical silica, 5 to 30% acetone in dichloromethane, 30 min) to give tert-butyl 2-(5-(6-tert-butylpyridin-2-ylamino)-6-carbamoylpyridazin-3-ylamino)-4-methylpentylcarbamate (112 mg, 231 μmol, 64%) as a pale yellow gum. This material was used directly into the next step without further purification.

Step 4

6-(1-Amino-4-methylpentan-2-ylamino)-4-(6-tert-butylpyridin-2-ylamino)pyridazine-3-carboxamide

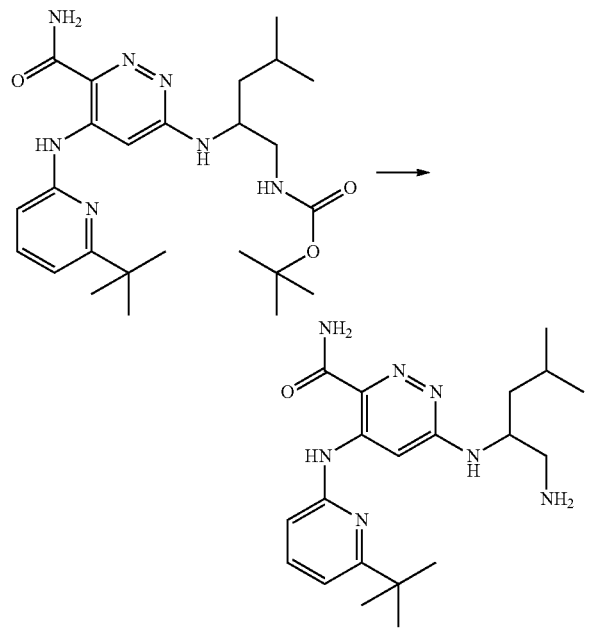

tert-Butyl 2-(5-(6-tert-butylpyridin-2-ylamino)-6-carbamoylpyridazin-3-ylamino)-4-methylpentylcarbamate (110 mg, 227 μmol) was dissolved in dichloromethane (2 mL) and then TFA (1.29 g, 873 μL, 11.3 mmol) was added. The pale yellow, clear solution was stirred at room temperature for 14 h. The yellow solution was concentrated in vacuo to a yellow residue and then purified by chromatography (silica, 11 g spherical, 0 to 10% of a 9:1 MeOH:NH$_4$OH solution in dichloromethane, 20 min) to give a white powder that was dissolved in hot ethanol (30 mL) and reconcentrated in vacuo three times to remove any residual dichloromethane, and finally dried in vacuo to give 6-(1-amino-4-methylpentan-2-ylamino)-4-(6-tert-butylpyridin-2-ylamino)pyridazine-3-carboxamide (44 mg, 114 μmol, 50%) as a white powder. $^1$H NMR (CHLOROFORM-d) δ: 11.52 (br. s., 1H), 8.43 (s, 1H), 8.06 (br. s., 1H), 7.55 (t, J=7.8 Hz, 1H), 6.94 (d, J=7.6 Hz, 1H), 6.71 (d, J=8.1 Hz, 1H), 5.53 (br. s., 1H), 5.12 (br. s., 1H), 4.00 (br. s., 1H), 2.99 (dd, J=13.1, 4.5 Hz, 1H), 2.80 (dd, J=13.1, 5.1 Hz, 1H), 1.79 (dt, J=13.3, 6.9 Hz, 1H), 1.29-1.64 (m, 11H), 0.96 (dd, J=14.0, 6.7 Hz, 6H); MS (EI/CI) m/z: 386.2 [M+H].

Example 13

6-(2-Aminoethoxy)-4-(5,6-dimethylpyridin-2-ylamino)pyridazine-3-carboxamide

Step 1

Ethyl 6-chloro-4-(5,6-dimethylpyridin-2-ylamino)pyridazine-3-carboxylate

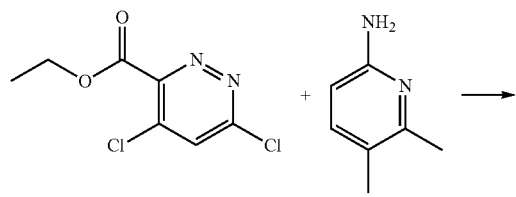

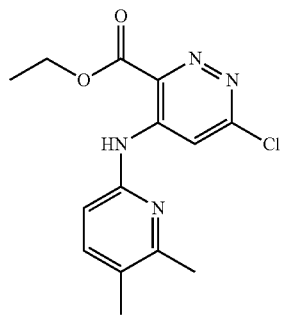

A pressure tube was charged with ethyl 4,6-dichloropyridazine-3-carboxylate (3000 mg, 13.6 mmol), 5,6-dimethylpyridin-2-amine (2.49 g, 20.4 mmol) and acetonitrile (8 mL). The mixture was heated with stirring in an oil bath at 130° C. for 18 h. After cooling to room temperature, the solvent was evaporated and the residue was suspended in dichloromethane, adsorbed on silica gel and then purified by flash chromatography (silica gel, 50 μm, 80 g column from Analogix, 0 to 10% acetone in dichloromethane, 20 min) to afford ethyl 6-chloro-4-(5,6-dimethylpyridin-2-ylamino)pyridazine-3-carboxylate (2.45 g, 59%) as a yellow solid. $^1$H NMR (400 MHz, DMSO-d$_6$) δ ppm 10.20 (s, 1H), 8.86 (s, 1H), 7.57 (d, J=8.08 Hz, 1H), 6.97 (d, J=8.08 Hz, 1H), 4.40 (q, J=7.24 Hz, 2H), 2.42 (s, 3H), 2.23 (s, 3H), 1.35 (t, J=7.20 Hz, 3H); MS (EI/CI) m/z: 307 [M+H]$^+$.

Step 2

6-Chloro-4-(5,6-dimethylpyridin-2-ylamino)pyridazine-3-carboxamide

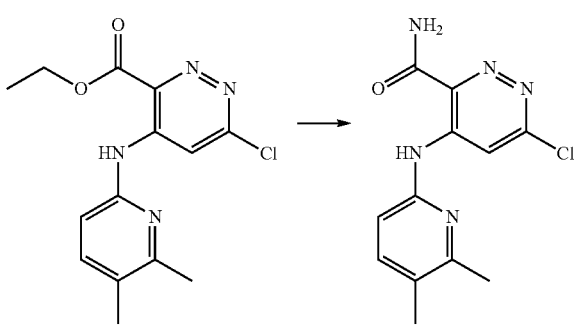 [SMILES: CCOC(=O)c1nnc(Cl)cc1Nc1ccc(C)c(C)n1 ; Cc1ccc(Nc2cc(Cl)nnc2C(N)=O)nc1C]

A pressure tube was charged ethyl 6-chloro-4-(5,6-dimethylpyridin-2-ylamino)pyridazine-3-carboxylate (2.44 g, 7.95 mmol) and ammonia in MeOH (7M, 60 mL, 420 mmol). This mixture was heated with stirring at 50° C. for 18 h. After cooling to room temperature the reaction mixture, a yellow suspension, was filtered and the white residue obtained was dried under high vacuum to give 6-chloro-4-(5,6-dimethylpyridin-2-ylamino)pyridazine-3-carboxamide (2.12 g, 96%). This was used in the next step without further purification. $^1$H NMR (400 MHz, CHLOROFORM-d) δ ppm 11.48 (br. s., 1H), 9.18 (s, 1H), 8.17 (br. s., 1H), 7.43 (d, J=8.34 Hz, 1H), 6.74 (d, J=7.83 Hz, 1H), 5.67 (br. s., 1H), 2.53 (s, 3H), 2.28 (s, 3H); MS (EI/CI) m/z: 278 [M+H]$^+$.

Step 3

4-(5,6-Dimethylpyridin-2-ylamino)-6-oxo-1,6-dihydropyridazine-3-carboxamide

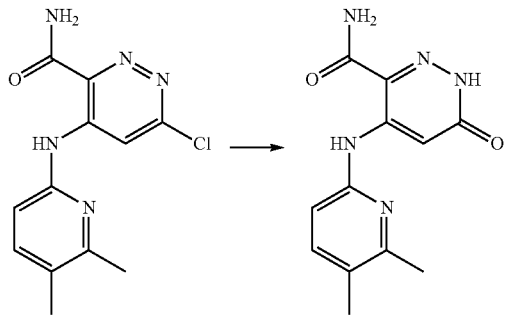 [SMILES: Cc1ccc(Nc2cc(Cl)nnc2C(N)=O)nc1C ; Cc1ccc(Nc2cc(=O)[nH]nc2C(N)=O)nc1C]

A microwave vial was charged with 6-chloro-4-(5,6-dimethylpyridin-2-ylamino)pyridazine-3-carboxamide (185 mg, 666 µmol), AcOH (3.99 g, 3.8 mL, 66.4 mmol), sodium acetate (82.0 mg, 0.999 mmol) and water (1.52 g, 1.52 mL, 84.4 mmol). The reaction mixture was stirred at 140° C. for 2 h in a microwave. After cooling to room temperature, the reaction mixture was concentrated in vacuo and then the crude residue purified by chromatography (spherical silica 20-45 50 µm, 11 g, Versaflash from Supelco, eluting with 0.1:1.9:98 NH$_4$OH:MeOH:dichloromethane to 0.6:11.4:88 NH$_4$OH:MeOH:dichloromethane over 40 min) to give 4-(5,6-dimethylpyridin-2-ylamino)-6-oxo-1,6-dihydropyridazine-3-carboxamide (45 mg, 26%) as a yellow solid $^1$H NMR (400 MHz, DMSO-d$_6$) δ ppm 12.89 (s, 1H), 11.28 (s, 1H), 8.12 (s, 1H), 7.93 (s, 1H), 7.81 (s, 1H), 7.49 (d, J=8.08 Hz, 1H), 6.76 (d, J=8.08 Hz, 1H), 2.38-2.45 (m, 3H), 2.21 (s, 3H); MS (EI/CI) m/z: 260 [M+H]$^+$.

Step 4

4-(5,6-Dimethylpyridin-2-ylamino)-6-(2-(1,3-dioxoisoindolin-2-yl)ethoxy)pyridazine-3-carboxamide

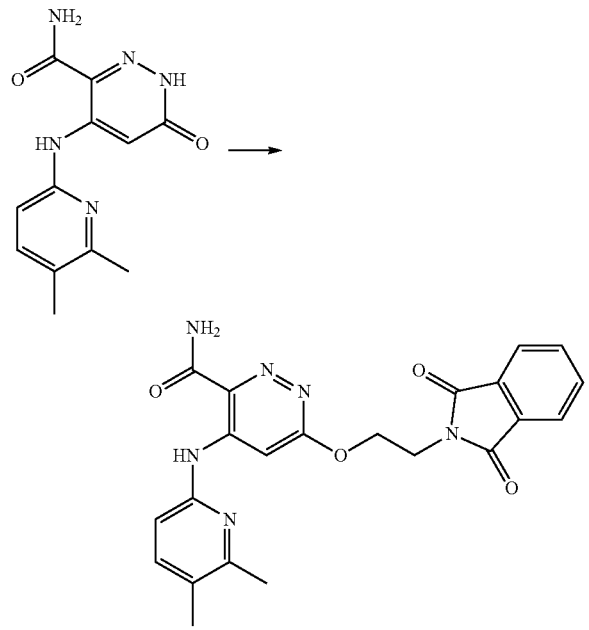

To a stirred solution of 4-(5,6-dimethylpyridin-2-ylamino)-6-oxo-1,6-dihydropyridazine-3-carboxamide (35 mg, 135 µmol) in DMF (3 mL) was added sodium hydride (6.48 mg, 270 µmol) and the reaction mixture was stirred for 30 min at room temperature. 2-(2-bromoethyl)isoindoline-1,3-dione (51.5 mg, 202 µmol) was added and the mixture (a yellow suspension) was stirred for 16 h at room temperature. The reaction mixture was quenched with water (20 mL) and diethyl ether (20 mL). The precipitate was collected by filtration, the filtrates were extracted with ether. The organic extracts were combined with the collected solid and purified by chromatography (spherical silica, 11 g, Versaflash from Supelco, 0% to 10% MeOH in dichloromethane) to give 4-(5,6-dimethylpyridin-2-ylamino)-6-(2-(1,3-dioxoisoindolin-2-yl)ethoxy)pyridazine-3-carboxamide (49 mg, 84%) as a white solid. $^1$H NMR (400 MHz, DMSO-d$_6$) δ ppm 11.26-11.33 (m, 1H), 8.16 (br. s., 1H), 7.83 (br. s., 4H), 7.79 (br. s., 2H), 7.46-7.54 (m, 1H), 6.71-6.80 (m, 1H), 4.28-4.37 (m, 2H), 3.96-4.06 (m, 2H), 2.39 (s, 3H), 2.20 (s, 3H); MS (EI/CI) m/z: 433 [M+H]$^+$.

Step 5

6-(2-Aminoethoxy)-4-(5,6-dimethylpyridin-2-ylamino)pyridazine-3-carboxamide

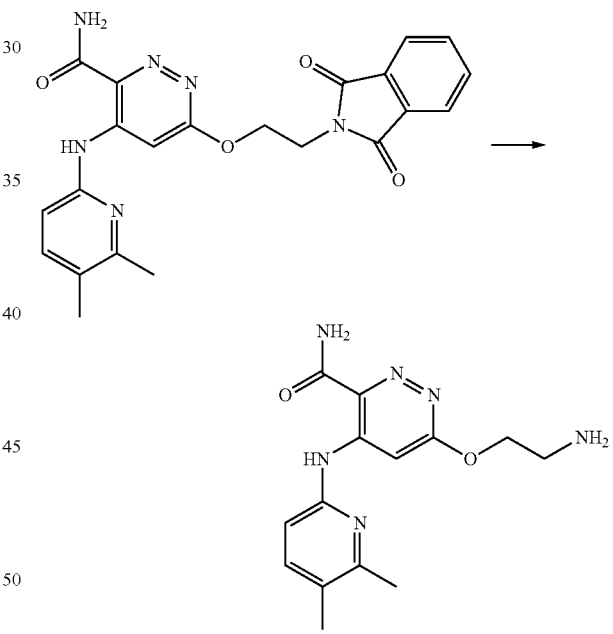

A pressure tube was charged with 4-(5,6-dimethylpyridin-2-ylamino)-6-(2-(1,3-dioxoisoindolin-2-yl)ethoxy) pyridazine-3-carboxamide (30 mg, 69.4 µmol) and EtOH (2 mL). To this solution was added hydrazine (2.67 mg, 2.61 µL, 83.3 µmol) and the reaction mixture was stirred for 3 h at room temperature, then warmed to 50° C. After 2 h, a second portion of hydrazine (2.2 mg, 69.4 µmol) was added and the reaction mixture was stirred overnight at 40° C. The mixture was cooled and concentrated in vacuo to afford a white solid. Purification by chromatography (spherical silica, 11 g, Versaflash from Supelco, eluting with 0.1:1.9:98 NH$_4$OH:MeOH:dichloromethane to 0.6:11.4:88 NH$_4$OH: MeOH:dichloromethane over 40 min) gave 6-(2-aminoethoxy)-4-(5,6-dimethylpyridin-2-ylamino)pyridazine-3-carboxamide (20 mg, 10%) as a white solid. $^1$H NMR (400 MHz, DMSO-d$_6$) d ppm 11.26 (s, 1H), 8.24 (br. s., 1H), 7.96 (br. s., 1H), 7.87 (s, 1H), 7.49 (d, J=8.08 Hz, 1H), 6.77 (d, J=8.08 Hz, 1H), 4.07 (t, J=6.44 Hz, 2H), 2.94 (t, J=6.32 Hz, 2H), 2.41 (s, 3H), 2.21 (s, 3H); MS (EI/CI) m/z: 303 [M+H]$^+$.

Example 14

6-Chloro-4-(3,5-dimethylphenylamino)pyridazine-3-carboxamide

Step 1

Ethyl 6-chloro-4-(3,5-dimethylphenylamino)pyridazine-3-carboxylate

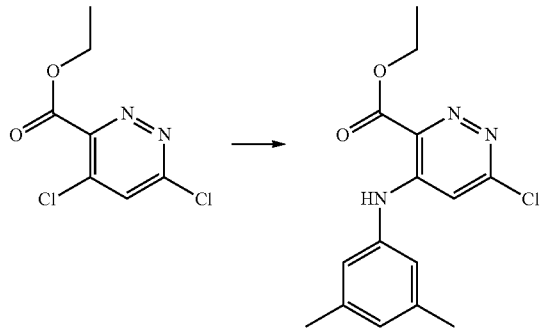 [SMILES: CCOC(=O)c1nnc(Cl)cc1Cl ; CCOC(=O)c1nnc(Cl)cc1Nc1cc(C)cc(C)c1]

To a stirred solution of ethyl 4,6-dichloropyridazine-3-carboxylate (700 mg, 3.17 mmol) in acetonitrile (11 mL) was added ethyl 4,6-dichloropyridazine-3-carboxylate (700 mg, 3.17 mmol) and the mixture heated at 140° C. in a sealed vial for 48 h. The mixture was cooled, concentrated in vacuo, and the residue obtained was then purified by chromatography (silica, 0 to 30% acetone in dichloromethane) to give ethyl 6-chloro-4-(3,5-dimethylphenylamino)pyridazine-3-carboxylate (104 mg, 340 µmol, 11%) as a light brown solid. $^1$H NMR (400 MHz, CHLOROFORM-d) δ ppm 9.70 (s, 1H), 7.03 (s, 1H), 6.99 (s, 1H), 6.88 (s, 2H), 4.57 (q, J=7.6 Hz, 2H), 2.38 (s, 6H), 1.52 (t, J=7.6 Hz, 3H); MS (EI/CI) m/z: 305.9 [M+H].

Step 2

6-Chloro-4-(3,5-dimethylphenylamino)pyridazine-3-carboxamide

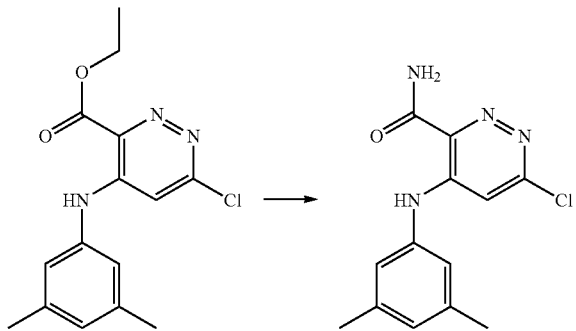 [SMILES: CCOC(=O)c1nnc(Cl)cc1Nc1cc(C)cc(C)c1 ; Cc1cc(C)cc(Nc2cc(Cl)nnc2C(N)=O)c1]

To a solution of ethyl 6-chloro-4-(3,5-dimethylphenylamino)pyridazine-3-carboxylate (104 mg, 340 µmol) in methanol was added 7N ammonia in methanol (4.86 mL, 34.0 mmol) and the mixture stirred at 50° C. for 16 h. The reaction mixture was then concentrated in vacuo to give 6-chloro-4-(3,5-dimethylphenylamino)pyridazine-3-carboxamide (90 mg, 325 µmol, 96%) as a brown solid. $^1$H NMR (400 MHz, DMSO-d) δ ppm 10.84 (s, 1H), 8.72 (s, 1H), 8.08 (s, 1H), 7.12 (s, 1H), 6.98 (s, 2H), 6.98 (s, 1H), 6.93 (s, 1H), 2.30 (s, 6H); MS (EI/CI) m/z: 276.9 [M+H].

Example 15

6-(1-Amino-4-methylpentan-2-ylamino)-4-(6-isopropyl-5-methylpyridin-2-ylamino)pyridazine-3-carboxamide Step 1

Ethyl 6-chloro-4-(6-isopropyl-5-methylpyridin-2-ylamino)pyridazine-3-carboxylate

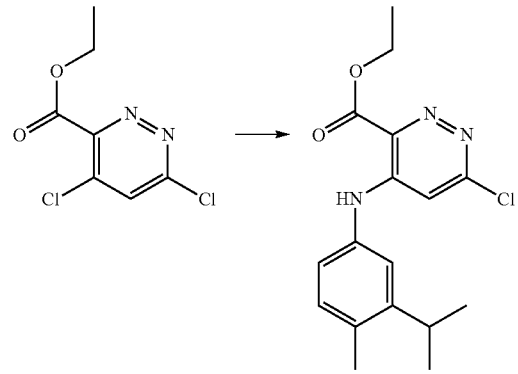 [SMILES: CCOC(=O)c1nnc(Cl)cc1Cl ; CCOC(=O)c1nnc(Cl)cc1Nc1ccc(C)c(C(C)C)c1]

A heavy walled sealable tube was charged with ethyl 4,6-dichloropyridazine-3-carboxylate (0.985 g, 4.46 mmol) and 6-isopropyl-5-methylpyridin-2-amine (1.01 g, 6.69 mmol). To the mixture was added acetonitrile (5 mL) and the yellow solution was heated with stirring at 130° C. for 20 h to give a brown solution. After cooling to room temperature, the acetonitrile was removed in vacuo to give a dark brown solid. This was dissolved in dichloromethane, adsorbed on silica gel and purified by chromatography (spherical silica 20-45 µm, 50 g, Versaflash from Supelco, 0% to 20% acetone in dichloromethane) to give ethyl 6-chloro-4-(6-isopropyl-5-methylpyridin-2-ylamino)pyridazine-3-carboxylate (848 mg, 57%) as yellow crystals. $^1$H NMR (400 MHz, CHLOROFORM-d) δ ppm 10.60 (br. s., 1H), 9.36 (s, 1H), 7.44 (d, J=8.08 Hz, 1H), 6.70 (d, J=8.08 Hz, 1H), 4.58 (q, J=7.07 Hz, 2H), 3.30 (spt, J=6.70 Hz, 1H), 2.34 (s, 3H), 1.52 (t, J=7.20 Hz, 3H), 1.33 (d, J=6.82 Hz, 6H); MS (EI/CI) m/z: 335 [M+H]$^+$

Step 2

6-Chloro-4-(6-isopropyl-5-methylpyridin-2-ylamino)pyridazine-3-carboxamide

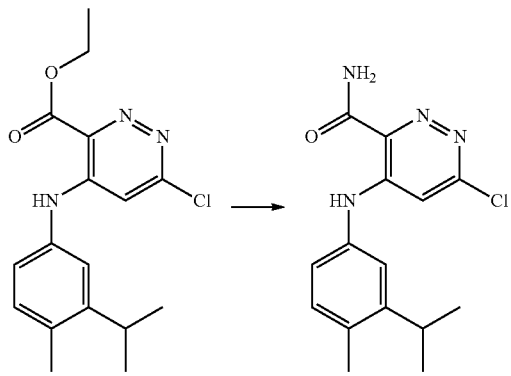 [SMILES: CCOC(=O)c1nnc(Cl)cc1Nc1ccc(C)c(C(C)C)c1 ; Cc1ccc(Nc2cc(Cl)nnc2C(N)=O)cc1C(C)C]

A pressure tube was charged with ethyl 6-chloro-4-(6-isopropyl-5-methylpyridin-2-ylamino)pyridazine-3-carboxylate (850 mg, 2.54 mmol) and a solution of ammonia in methanol (7M, 20 mL, 140 mmol). The light yellow suspension was stirred at 50° C. for 1.5 h, then concentrated in vacuo to give 6-chloro-4-(6-isopropyl-5-methylpyridin-2-ylamino)pyridazine-3-carboxamide (693 mg, 89%) as an orange solid. $^1$H NMR (400 MHz, CHLOROFORM-d) δ ppm 11.48 (br. s., 1H), 9.39 (s, 1H), 8.18 (br. s., 1H), 7.42 (d, J=8.08 Hz, 1H), 6.71 (d, J=8.08 Hz, 1H), 5.67 (br. s., 1H), 3.29 (dt, J=13.52, 6.63 Hz, 1H), 2.33 (s, 3H), 2.26-2.26 (m, 1H), 1.33 (d, J=6.82 Hz, 2H); MS (EI/CI) m/z: 306 [M+H]$^+$.

Step 3

6-(1-Amino-4-methylpentan-2-ylamino)-4-(6-isopropyl-5-methylpyridin-2-ylamino)pyridazine-3-carboxamide

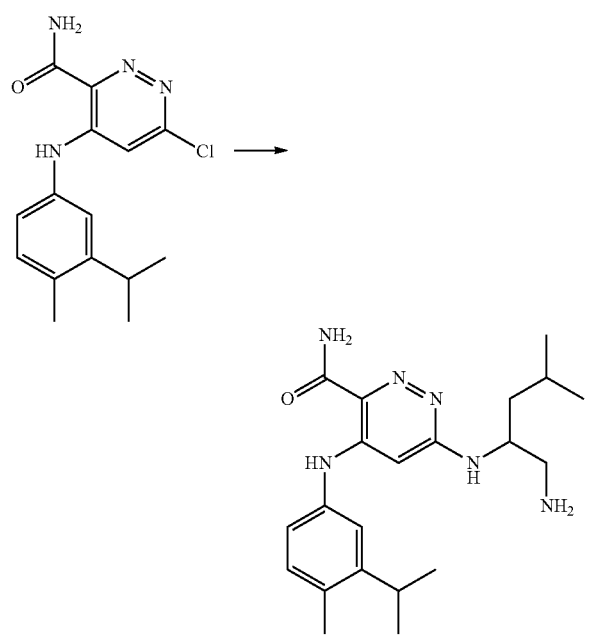

A pressure tube was charged with 6-chloro-4-(6-isopropyl-5-methylpyridin-2-ylamino)pyridazine-3-carboxamide (230 mg, 752 μmol), tert-butyl 2-amino-4-methylpentylcarbamate (244 mg, 1.13 mmol) and NMP (5 mL). The reaction mixture was stirred at 140° C. for 2.5 days. The mixture was concentrated using a Kugelrohr apparatus and high vacuum to give a brown solid. This was then purified by chromatography (spherical silica, 11 g, Versaflash from Supelco, eluting with 100% dichloromethane to 88:11.4:0.6 dichloromethane:MeOH:NH$_4$OH, 40 min) to give a light brown solid (215 mg). This solid was dissolved in dichloromethane (2 mL) and TFA (740 mg, 500 μL, 6.49 mmol). The mixture was stirred at room temperature for 18 h, then concentrated in vacuo to give a residue that was purified by flash chromatography (spherical silica, 11 g, Versaflash from Supelco, eluting with 100% dichloromethane to 88:11.4:0.6 dichloromethane:MeOH:NH$_4$OH, 40 min) to give 6-(1-amino-4-methylpentan-2-ylamino)-4-(6-isopropyl-5-methylpyridin-2-ylamino)pyridazine-3-carboxamide (67 mg, 23%) as an off-white solid. $^1$H NMR (400 MHz, DMSO-d$_6$) δ ppm 11.58 (br. s., 1H), 8.34 (br. s., 1H), 7.87 (br. s., 1H), 7.59 (br. s., 1H), 7.47 (d, J=8.08 Hz, 1H), 6.83 (d, J=8.34 Hz, 1H), 6.70 (d, J=8.34 Hz, 1H), 3.18-3.26 (m, 1H), 2.65 (br. s., 2H), 2.51 (br. m., 1H), 2.25 (s, 3H), 1.68 (d, J=7.33 Hz, 1H), 1.46-1.57 (m, 1H), 1.37-1.46 (m, 1H), 1.25 (d, J=6.32 Hz, 6H), 0.89 (dd, J=19.58, 6.44 Hz, 6H); MS (EI/CI) m/z: 386 [M+H]$^+$.

Example 16

6-((3R,4R)-3-Aminotetrahydro-2H-pyran-4-ylamino)-4-(6-tert-butylpyridin-2-ylamino)pyridazine-3-carboxamide

Step 1

Ethyl 4-(6-tert-butylpyridin-2-ylamino)-6-chloropyridazine-3-carboxylate

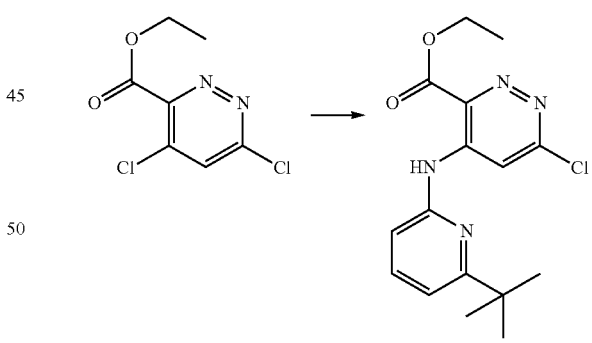

A mixture of ethyl 4,6-dichloropyridazine-3-carboxylate (0.73 g, 3.3 mmol) and 6-tert-butylpyridin-2-amine (992 mg, 6.61 mmol, available commercially from J&W PharmLab, LLC) was dissolved in acetonitrile (3 mL) and heated at 130° C. After 20 h, the a dark brown mixture was cooled, concentrated in vacuo, and then purified by chromatography (spherical silica 20-45 μM, 50 g, Versaflash Supelco, 0 to 20% acetone in dichloromethane, 20 min) to give ethyl 4-(6-tert-butylpyridin-2-ylamino)-6-chloropyridazine-3-carboxylate (539 mg, 49%) as a light brown residue. $^1$H NMR (CHLOROFORM-d) δ: 10.59 (s, 1H), 9.32 (s, 1H), 7.55 (t, J=7.9 Hz, 1H), 6.98 (d, J=7.2 Hz, 1H), 6.66 (d, J=7.9

Hz, 1H), 4.48 (q, J=7.2 Hz, 2H), 1.43 (t, J=7.2 Hz, 3H), 1.28-1.35 (m, 9H); MS (EI/CI) m/z: 335.0, 337.0 [M+H]⁺.

Step 2

4-(6-tert-Butylpyridin-2-ylamino)-6-chloro-pyridazine-3-carboxamide

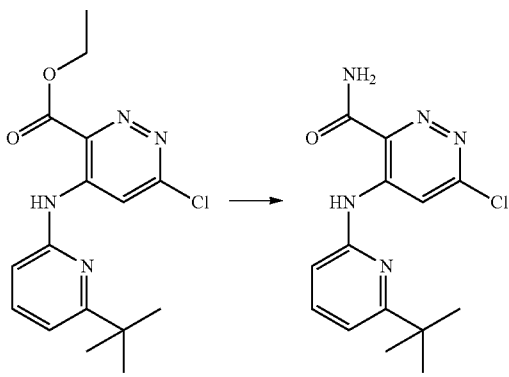 [SMILES: CCOC(=O)c1nnc(Cl)cc1Nc1cccc(C(C)(C)C)n1 ; CC(C)(C)c1cccc(Nc2cc(Cl)nnc2C(N)=O)n1]

Ethyl 4-(6-tert-butylpyridin-2-ylamino)-6-chloro-pyridazine-3-carboxylate (539 mg, 1.61 mmol) was suspended in ammonia (7M in methanol, 7.9 g, 10.0 mL, 70.0 mmol). The reaction was sealed in a flask and stirred at r.t. for 18 h. The mixture was concentrated in vacuo then dried under high vacuum to give 4-(6-tert-butylpyridin-2-ylamino)-6-chloropyridazine-3-carboxamide (492 mg, 100%) as an off-white solid. ¹H NMR (DMSO-d₆) δ: 11.94 (s, 1H), 9.23 (s, 1H), 8.84 (s, 1H), 8.19 (s, 1H), 7.74 (t, J=7.9 Hz, 1H), 7.14 (d, J=7.6 Hz, 1H), 6.92 (d, J=7.9 Hz, 1H), 1.34 (s, 9H); MS (EI/CI) m/z: 306.1, 308.1 [M+H]⁺.

Step 3

6-(2-Aminoethylamino)-4-(6-tert-butylpyridin-2-ylamino)pyridazine-3-carboxamide

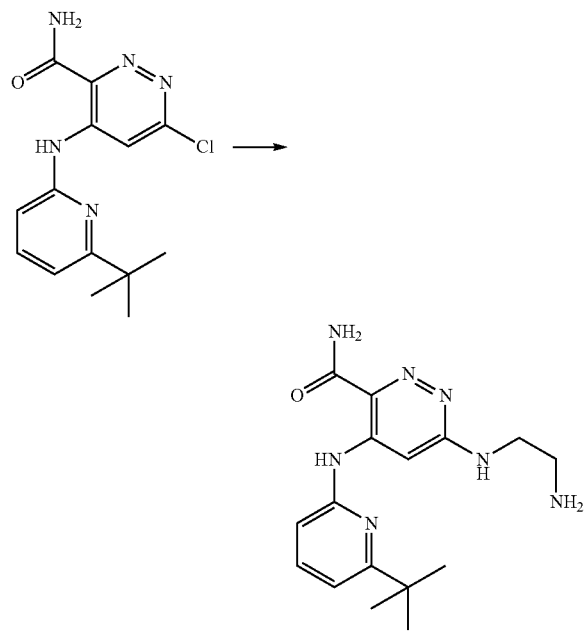

A pressure tube was charged with 4-(6-tert-butyl-pyridin-2-ylamino)-6-chloropyridazine-3-carboxamide (100 mg, 327 μmol) and NMP (2 mL). To this solution was added ethylenediamine (197 mg, 221 μL, 3.27 mmol) and the reaction mixture was heated with stirring at 130° C. for 1.5 h. The mixture was concentrated using a Kugelrohr distillation apparatus under high vacuum at 120° C. to afford a light brown solid. This was purified by chromatography (silica, 40 g, Thomson Scientific, 0 to 10% of a 9:1 MeOH:NH₄OH solution in CH₂Cl₂) to give a residue that was dissolved in hot EtOH and then concentrated. The solid obtained was suspended in EtOH, sonicated and the solid separated by filtration and then dried under high vacuum to finally give 6-(2-aminoethylamino)-4-(6-tert-butylpyridin-2-ylamino)pyridazine-3-carboxamide (27 mg, 25%) as an off-white solid. ¹H NMR (DMSO-d₆) δ: 11.76 (br. s., 1H), 8.37 (br. s., 1H), 7.99 (s, 1H), 7.55-7.72 (m, 2H), 7.19 (br. s., 1H), 6.98 (d, J=7.6 Hz, 1H), 6.73 (d, J=7.9 Hz, 1H), 3.26 (m, 2H), 2.75 (t, J=6.0 Hz, 2H), 1.71 (br. s., 2H), 1.33 (s, 9H); MS (EI/CI) m/z: 330.2 [M+H]⁺.

Example 17

(R)-6-(1-Amino-4-methylpentan-2-ylamino)-4-(6-tert-butylpyridin-2-ylamino)pyridazine-3-carboxamide Step 1

(R)-2-(dibenzylamino)-4-methylpentanamide

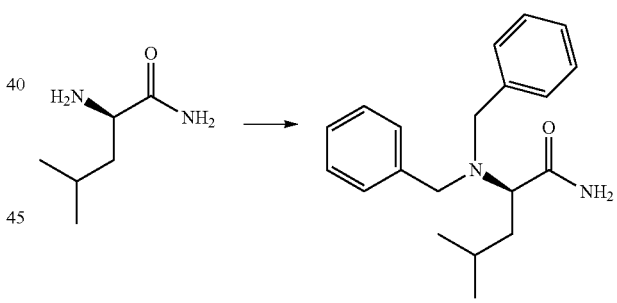

H-D-LEU-NH₂ (2.0 g, 15.4 mmol) and benzaldehyde (1.79 g, 16.9 mmol) were dissolved in dry DCM (90 mL) then sodium triacetoxyborohydride (3.91 g, 18.4 mmol) was added. The suspension was stirred at room temperature for 12 h. A second portion of benzaldehyde (1.79 g, 16.9 mmol) and sodium triacetoxyborohydride (3.91 g, 18.4 mmol) was added. After 24 h, a saturated solution of ammonium chloride was added, and the phases were separated. The organic phase was washed with saturated aqueous sodium bicarbonate then brine, dried (MgSO₄), filtered and concentrated in vacuo to a colorless oil. Purification by chromatography (silica, 80 g, 0-5% acetone in dichloromethane, 30 min) gave (R)-2-(dibenzylamino)-4-methylpentanamide (3.42 g, 11.0 mmol, 72%) as a colorless oil. MS (EI/CI) m/z: 311.2 [M+H]⁻. This contained ~32% benzyl alcohol, and was reacted directly in the next step without further purification.

Step 2

(R)—N2,N2-Dibenzyl-4-methylpentane-1,2-diamine

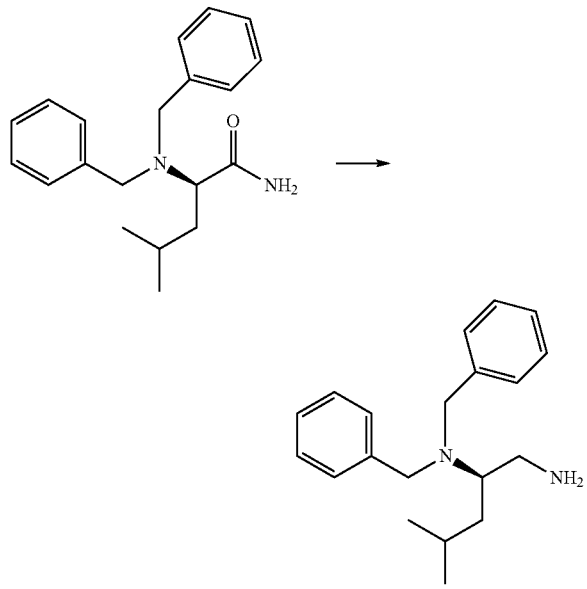

(R)-2-(dibenzylamino)-4-methylpentanamide (3.42 g, 11.0 mmol) was dissolved in THF (30 mL) then LiAlH$_4$ (2 M in THF, 5.51 mL, 11.0 mmol) was added dropwise under nitrogen. The mixture was stirred at room temperature for 18 h. LiAlH$_4$ (2 M in THF, 2.5 mL, 5.0 mmol) was added and the mixture heated to 70° C. After 2 h, the red, cloudy solution was cooled and then quenched with sodium sulfate decahydrate (~2 g). The color was lost, becoming clear. After stirring for 1 h, the mixture was filtered and concentrated in vacuo to a clear yellow oil (2.8 g). The crude material was purified by chromatography (silica, 80 g, 0% to 10% of 1:9 NH$_4$OH:MeOH solution in DCM) to give (R)—N2,N2-dibenzyl-4-methylpentane-1,2-diamine (1.59 g, 5.36 mmol, 49%) as a colorless oil. MS (EI/CI) m/z: 297.2 [M+H]$^+$.

Step 3

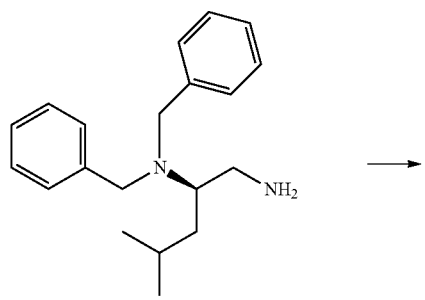

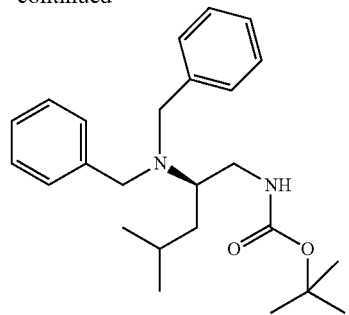

(R)—N2,N2-dibenzyl-4-methylpentane-1,2-diamine (1.593 g, 5.37 mmol) was dissolved in THF (10 mL). To this solution was added Boc$_2$O (1.23 g, 5.64 mmol) and DMAP (67.0 mg, 537 μmol). The solution was stirred for 18 h at room temperature, then the mixture was concentrated in vacuo to afford (R)-tert-butyl 2-(dibenzylamino)-4-methylpentylcarbamate (2.1 g) as a yellow viscous oil which was used in the next step without any further purification.

Step 4

(R)-tert-Butyl 2-amino-4-methylpentylcarbamate

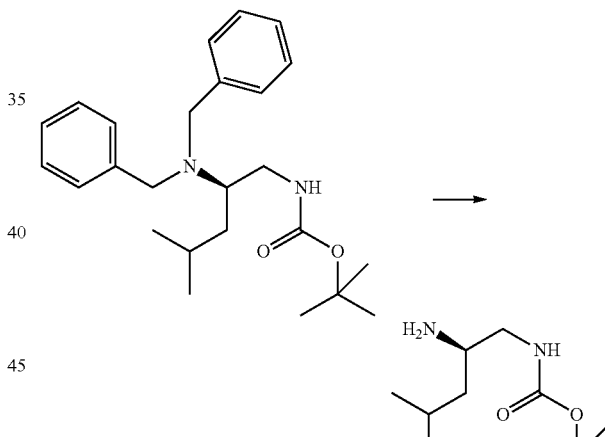

A suspension of 10% Pd/C (500 mg, 4.7 mmol) in MeOH (30 mL) was added to a solution of (R)-tert-butyl 2-(dibenzylamino)-4-methylpentylcarbamate (2.1 g, 5.3 mmol) in MeOH (30 mL). The reaction mixture was shaken in a Parr apparatus for 1.5 h under a hydrogen atmosphere (40 psi). Additional 10% Pd/C (500 mg, 4.7 mmol) was added and the reaction was reacted in the Parr apparatus for a further 3 h. The reaction mixture was filtered over celite and evaporated affording 1.20 g viscous oil. Purification by chromatography (silica, 11 g, Versaflash from Supelco, eluting with 0% to 60% of a solution comprising 2400 mL DCM, 240 mL MeOH and 40 mL NH$_4$OH in dichloromethane) gave (R)-tert-butyl 2-amino-4-methylpentylcarbamate (315 mg, 28%) as a colorless oil. MS (EI/CI) m/z: 217.2 [M+H]$^+$.

Step 5

(R)-6-(1-Amino-4-methylpentan-2-ylamino)-4-(6-tert-butylpyridin-2-ylamino)pyridazine-3-carboxamide

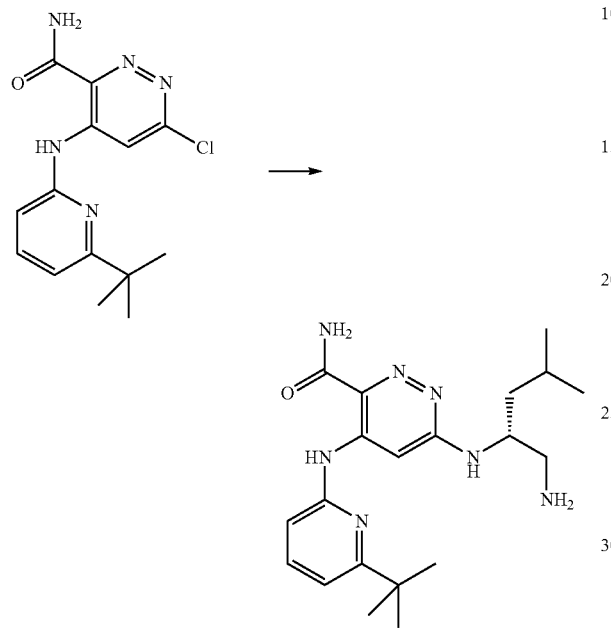

A pressure tube was charged with 4-(6-tert-butylpyridin-2-ylamino)-6-chloropyridazine-3-carboxamide (100 mg, 327 µmol), (R)-tert-butyl 2-amino-4-methylpentylcarbamate (141 mg, 654 µmol) and NMP (3 mL). The reaction mixture was stirred at 140° C. for 22 h, then was cooled and concentrated using a Kugelrohr apparatus under high vacuum and at 120° C. to afford a light brown solid. Purification by chromatography (spherical silica 20-45 µm, 11 g, Versaflash from Supelco, eluting with 100% dichloromethane to 90:9.5:0.5 dichloromethane:MeOH:NH$_4$OH over 40 min) gave (R)-tert.-butyl 2-(5-(6-tert-butylpyridin-2-ylamino)-6-carbamoylpyridazin-3-ylamino)-4-methylpentylcarbamate as a white solid (69 mg, 55%). This product was dissolved in dichloromethane (2 mL) and TFA (740 mg, 500 µL, 6.49 mmol). The mixture was stirred at room temperature for 1.5 h, then concentrated in vacuo and purified chromatography (spherical silica 20-45 µm, 11 g, Versaflash from Supelco, eluting with 100% dichloromethane to 90:9.5:0.5 dichloromethane:MeOH:NH$_4$OH over 40 min) to give (R)-6-(1-amino-4-methylpentan-2-ylamino)-4-(6-tert-butylpyridin-2-ylamino)pyridazine-3-carboxamide (22 mg, 18%) as a white solid. $^1$H NMR (400 MHz, DMSO-d$_6$) δ ppm 11.72 (br. s., 1H), 8.37 (br. s., 1H), 7.92 (br. s., 1H), 7.56-7.76 (m, 3H), 7.00 (d, J=7.33 Hz, 1H), 6.87 (br. s., 1H), 6.76 (d, J=7.83 Hz, 1H), 2.66 (br. s., 2H), 1.21-1.78 (m, 4H), 1.35 (br. s., 9H), 0.88 (dd, J=19.83, 5.68 Hz, 6H); MS (EI/CI) m/z: 386 [M+H]$^+$.

Example 18

6-(2-aminoethylamino)-4-(6-isopropyl-5-methylpyridin-2-ylamino)pyridazine-3-carboxamide

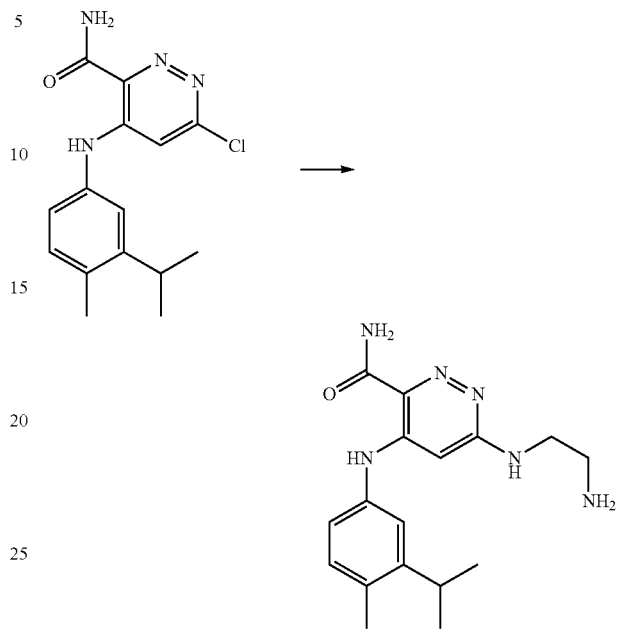

A flask was charged with 6-chloro-4-(6-isopropyl-5-methylpyridin-2-ylamino)pyridazine-3-carboxamide (100 mg, 327 µmol, prepared as described in Example 15) and DMSO (2 mL). To this solution was added ethylenediamine (197 mg, 221 µL, 3.27 mmol) and the reaction mixture was heated with stirring at 120° C. for 1.5 h. The solvents were concentrated under high vacuum and the residue then purified by chromatography (spherical silica 20-45 µM, 23 g, Versaflash Supelco, eluting with 0 to 10% of a 9:1 MeOH:NH$_4$OH solution in dichloromethane, 20 min) to give 6-(2-aminoethylamino)-4-(6-isopropyl-5-methylpyridin-2-ylamino)pyridazine-3-carboxamide (70 mg, 65%) as an off-white solid. $^1$H NMR (DMSO-d6) δ: 11.61 (s, 1H), 8.35 (br. s., 1H), 7.93 (s, 1H), 7.60 (br. s., 1H), 7.45 (d, J=8.3 Hz, 1H), 7.07-7.21 (m, 1H), 6.67 (d, J=8.3 Hz, 1H), 3.14-3.27 (m, 2H), 3.03-3.14 (m, 1H), 2.75 (t, J=6.2 Hz, 2H), 2.23 (s, 3H), 1.55 (br. s., 2H), 1.23 (d, J=6.8 Hz, 6H); MS (EI/CI) m/z: 330.2 [M+H]$^+$.

Example 19

6-((1-Aminocyclopropyl)methylamino)-4-(6-tert-butylpyridin-2-ylamino)pyridazine-3-carboxamide

Step 1 tert-Butyl 1-((5-(6-tert-butylpyridin-2-ylamino)-6-carbamoylpyridazin-3-ylamino)methyl)cyclopropylcarbamate

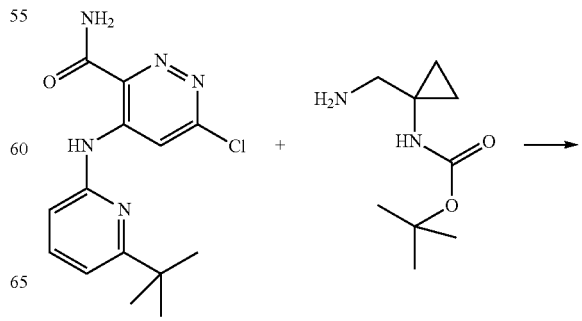

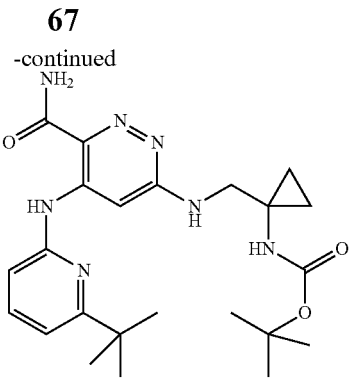

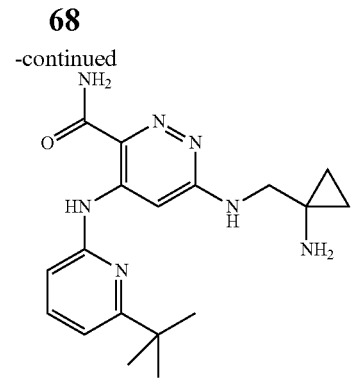

A pressure tube was charged with 4-(6-tert-butylpyridin-2-ylamino)-6-chloropyridazine-3-carboxamide (100 mg, 327 μmol) and NMP (2 mL). To this solution was added tert-butyl 1-(aminomethyl)cyclopropylcarbamate (60.9 mg, 327 μmol) and the reaction mixture was heated with stirring at 130° C. for 18 h. Further tert-butyl 1-(aminomethyl)cyclopropylcarbamate (60.9 mg, 327 μmol) was added in small portions over an 8 h period, then one more equivalent of tert-butyl 1-(aminomethyl)cyclopropylcarbamate (60.9 mg, 327 μmol) was added in a single portion and heating continued 72 h. The reaction mixture was cooled and then concentrated using a Kugelrohr distillation apparatus under high vacuum and at 120° C. to afford a light brown solid. This solid was dissolved in dichloromethane and then purified by chromatography (silica gel 50 μm, 40 g, Analogix, 0 to 5% of a 9:1 MeOH:NH$_4$OH solution in CH$_2$Cl$_2$, 20 min) to yield tert-butyl 1-((5-(6-tert-butylpyridin-2-ylamino)-6-carbamoylpyridazin-3-ylamino)methyl)cyclopropylcarbamate (107 mg, 72%) as a brown foam. $^1$H NMR (CHLOROFORM-d) δ: 11.45 (br. s., 1H), 8.37 (s, 1H), 8.11-8.23 (m, 1H), 7.52 (t, J=7.9 Hz, 1H), 7.14-7.35 (m, 1H), 6.92 (d, J=7.6 Hz, 1H), 6.66 (d, J=8.3 Hz, 1H), 6.06 (br. s., 1H), 5.72 (d, J=3.0 Hz, 1H), 3.35 (d, J=4.9 Hz, 2H), 1.42 (s, 9H), 1.40 (s, 9H), 0.77-0.91 (m, 4H); MS (EI/CI) m/z: 456.2 [M+H]$^+$.

Step 2

6-((1-Aminocyclopropyl)methylamino)-4-(6-tert-butylpyridin-2-ylamino)pyridazine-3-carboxamide

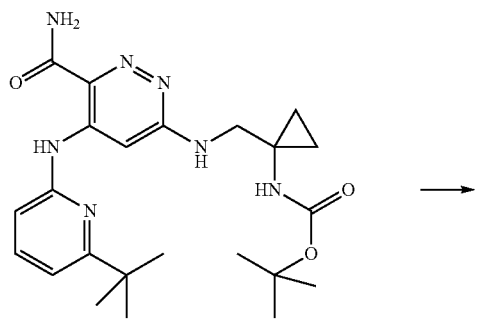

To a solution of tert-butyl 1-((5-(6-tert-butylpyridin-2-ylamino)-6-carbamoylpyridazin-3-ylamino)methyl)cyclopropylcarbamate (107 mg, 235 μmol) in CH$_2$Cl$_2$ (3 mL) was added TFA (1.48 g, 1.00 mL, 13.0 mmol) and the mixture stirred to room temperature for 18 h. The mixture was then concentrated in vacuo and the residue obtained was purified by chromatography (spherical silica 20-45 μM, 23 g, Versaflash Supelco, 0 to 5% of a 9:1 MeOH:NH$_4$OH solution in CH$_2$Cl$_2$, 20 min) to give the title produce that was then recrystallized from hot ethanol to give 6-((1-aminocyclopropyl)methylamino)-4-(6-tert-butylpyridin-2-ylamino)pyridazine-3-carboxamide (31 mg, 37%) as a white solid. $^1$H NMR (DMSO-d$_6$) δ: 11.74 (s, 1H), 8.37 (br. s., 1H), 7.98 (s, 1H), 7.57-7.75 (m, 2H), 7.26 (br. s., 1H), 6.99 (d, J=7.6 Hz, 1H), 6.74 (d, J=7.9 Hz, 1H), 3.22-3.28 (m, 2H), 2.10 (br. s., 2H), 1.33 (s, 9H), 0.47 (m, 4H); MS (EI/CI) m/z: 356.3 [M+H]$^+$.

Example 20

6-(2-aminoethylamino)-4-(6-isopropyl-5-methoxypyridin-2-ylamino)pyridazine-3-carboxamide Step 1

3-Methoxy-6-nitro-2-(prop-1-en-2-yl)pyridine

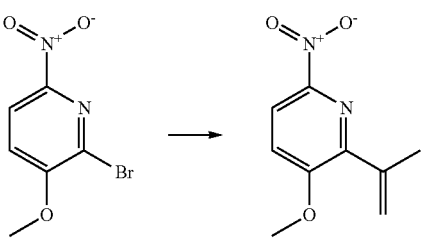

In a microwave vial was added a mixture of 2-bromo-3-methoxy-6-nitropyridine (1.5 g, 6.44 mmol), 4,4,5,5-tetramethyl-2-(prop-1-en-2-yl)-1,3,2-dioxaborolane (1.41 g, 8.37 mmol), tetrakis(triphenylphosphine)palladium (0) (744 mg, 644 μmol), potassium phosphate tribasic (2.73 g, 12.9 mmol), DMA (16.1 mL) and water (5.36 mL). The vial was sealed and heated in the microwave for 20 min at 150° C., then cooled and diluted with ethyl acetate and brine. The organic phase was separated and washed with brine (3×), then concentrated in vacuo and purified by chromatography (silica, 5 to 35% ethyl acetate in hexanes) to give 3-methoxy-6-nitro-2-(prop-1-en-2-yl)pyridine (824 mg, 4.24 mmol, 66%) as a brown solid. MS (EI/CI) m/z: 194.8 [M+H].

Step 2

6-Isopropyl-5-methoxypyridin-2-amine

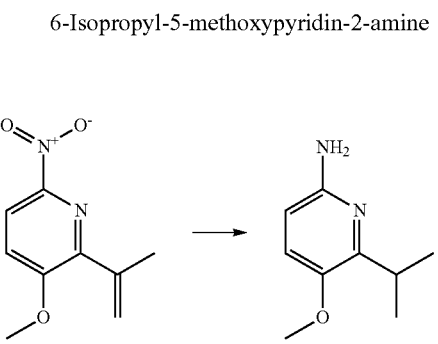

To a solution of 3-methoxy-6-nitro-2-(prop-1-en-2-yl)pyridine (824 mg, 4.24 mmol) in ethanol (14.1 mL) was added 10% palladium on carbon (45.2 mg, 424 µmol). The reaction mixture was evacuated and back filled with hydrogen. This was repeated two more times. The reaction was stirred under hydrogen at 1 atm for 16 h. The mixture was then filtered reaction through a pad of celite, the filtrate concentrated in vacuo, and then purified by chromatography (silica, 10 to 60% ethyl acetate in hexanes) to give 6-isopropyl-5-methoxypyridin-2-amine (562 mg, 3.38 mmol, 80%) as a yellow solid. $^1$H NMR (400 MHz, CHLOROFORM-$d_6$) δ ppm 7.04 (d, J=8.7 Hz, 1H), 6.33 (d, J=8.7 Hz, 1H), 4.12 (br. s, 2H), 3.78 (s, 3H), 3.36 (m, 1H), 1.22 (d, J=7.0 Hz, 6H); MS (EI/CI) m/z: 166.8 [M+H].

Step 3

6-Chloro-4-(6-isopropyl-5-methoxypyridin-2-ylamino)pyridazine-3-carboxylate

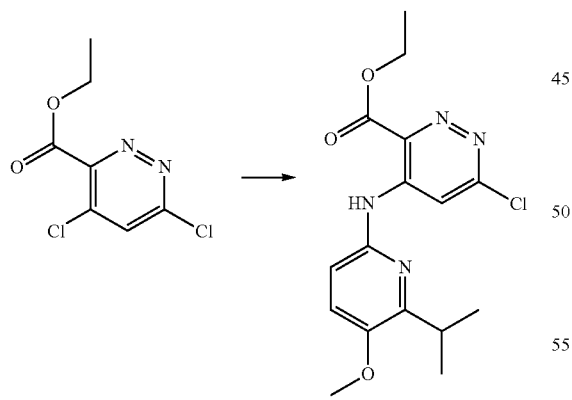

To a solution of ethyl 4,6-dichloropyridazine-3-carboxylate (747 mg, 3.38 mmol) in acetonitrile (11.3 mL) was added 6-isopropyl-5-methoxypyridin-2-amine (562 mg, 3.38 mmol) and heated to 80° C. for 20 h. The mixture was cooled and concentrated in vacuo. Purification by chromatography (silica, 10 to 50% ethyl acetate in hexanes) gave ethyl 6-chloro-4-(6-isopropyl-5-methoxypyridin-2-ylamino)pyridazine-3-carboxylate (438 mg, 1.25 mmol, 37%) as a yellow solid. $^1$H NMR (400 MHz, CHLOROFORM-$d_6$) δ ppm 10.61 (s, 1H), 9.15 (s, 1H), 7.22 (d, J=8.7 Hz, 1H), 6.61 (d, J=8.7 Hz, 1H), 4.57 (q, J=7.6 Hz, 2H), 3.88 (s, 3H), 3.53 (m, 1H), 1.53 (t, J=7.0 Hz, 3H), 1.31 (d, J=6.7 Hz, 6H); MS (EI/CI) m/z: 351.0 [M+H].

Step 4

Ethyl 6-chloro-4-(6-isopropyl-5-methoxypyridin-2-ylamino)pyridazine-3-carboxylate

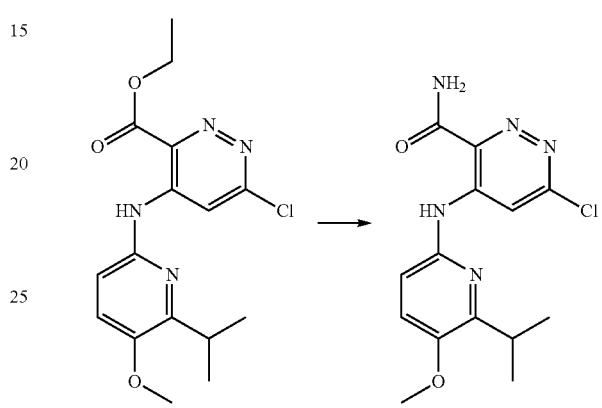

A mixture of ethyl 6-chloro-4-(6-isopropyl-5-methoxypyridin-2-ylamino)pyridazine-3-carboxylate (438 mg, 1.25 mmol) and ammonia in methanol (7 N, 8.92 mL, 62.4 mmol) in methanol (1 mL) was warmed at 40° C. for 16 h. The mixture was then concentrated in vacuo to give ethyl 6-chloro-4-(6-isopropyl-5-methoxypyridin-2-ylamino)pyridazine-3-carboxylate (438 mg, 1.25 mmol, 100%) as an off-white solid. $^1$H NMR (400 MHz, DMSO-$d_6$) δ ppm 11.75 (s, 1H), 9.03 (s, 1H), 8.78 (s, 1H), 8.13 (s, 1H), 7.48 (d, J=8.5 Hz, 1H), 7.00 (d, J=8.5 Hz, 1H), 3.82 (s, 3H), 3.44 (m, 1H), 1.22 (d, J=6.6 Hz, 6H); MS (EI/CI) m/z: 321.9 [M+H].

Step 5

6-(2-Aminoethylamino)-4-(6-isopropyl-5-methoxypyridin-2-ylamino)pyridazine-3-carboxamide

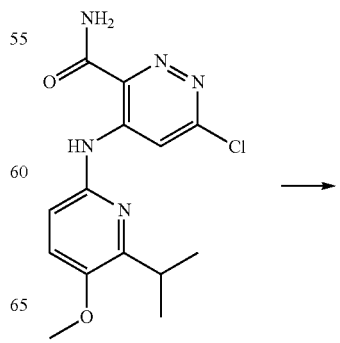

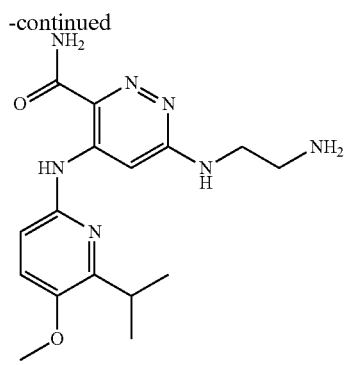

To a solution of 6-chloro-4-(6-isopropyl-5-methoxypyridin-2-ylamino)pyridazine-3-carboxamide (170 mg, 528 µmol) in NMP (1.76 mL) was added ethane-1,2-diamine (127 mg, 142 µl, 2.11 mmol) and the mixture heated to 100° C. for 16 h. The reaction mixture was cooled, concentrated in vacuo, and then diluted with methanol. The precipitate that formed was collected by filtration and dried to give 6-(2-aminoethylamino)-4-(6-isopropyl-5-methoxypyridin-2-ylamino)pyridazine-3-carboxamide (81 mg, 235 µmol, 44%) as a white solid. $^1$H NMR (400 MHz, DMSO-$d_6$) δ ppm 11.48 (s, 1H), 8.31 (s, 1H), 7.75 (s, 1H), 7.57 (s, 1H), 7.41 (d, J=9.0 Hz, 1H), 7.08 (t, J=5.6 Hz, 1H), 6.83 (d, J=8.7 Hz, 1H), 3.79 (s, 3H), 3.40 (m, 1H), 2.78 (t, J=5.9 Hz, 2H), 1.22 (d, J=6.8 Hz, 6H); MS (EI/CI) m/z: 346.3 [M+H].

Example 21

6-((1R,2S)-2-Aminocyclohexylamino)-4-(6-(2-cyanopropan-2-yl)pyridin-2-ylamino)pyridazine-3-carboxamide Step 1

2-(6-Bromopyridin-2-yl)-2-methylpropanenitrile

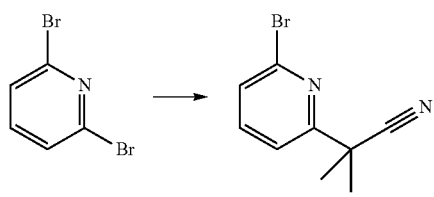

A flask was charged with a solution of iso-butyronitrile (3.29 g, 4.27 mL, 47.6 mmol) in toluene (100 mL), then the solution was cooled to 0° C. and KHMDS (0.5 M in toluene, 100 mL, 50.0 mmol) was added slowly. After complete addition, the reaction mixture was warmed to room temperature over 1 h. The resulting mixture was added to a solution of 2,6-dibromopyridine (28.2 g, 119 mmol, available commercially from Aldrich) in toluene (100 mL). While adding, the light yellow solution became dark red. The reaction mixture was stirred at room temperature for 18 h. The crude mixture was diluted with ether then washed successively with saturated aqueous ammonium chloride solution and brine. The organic phase was dried over magnesium sulfate, filtered and concentrated in vacuo. The semi-solid residue was suspended in a small amount of toluene, filtered, and the recovered starting material discarded. The filtrate was concentrated in vacuo then purified by chromatography (silica gel 50 µm, 220 g, Rediflash Teledyne-Isco, 0 to 50% dichloromethane in hexanes, 20 min) to obtain 2-(6-bromopyridin-2-yl)-2-methylpropanenitrile (7.61 g, 28%) as a light yellow oil that solidified into a white solid upon standing. $^1$H NMR (CHLOROFORM-d) δ: 7.58-7.61 (m, 2H), 7.42-7.46 (m, 1H), 1.76 (s, 6H); MS (EI/CI) m/z: 225.0 226.9 [M+H].

Step 2

2-(6-Aminopyridin-2-yl)-2-methylpropanenitrile

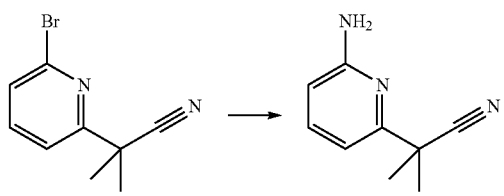

A heavy walled resealable tube was loaded under an argon atmosphere with copper (I) oxide (159 mg, 1.11 mmol), 2-(6-bromopyridin-2-yl)-2-methylpropanenitrile (5.0 g, 22.2 mmol), ammonium hydroxide (28% solution, 26.9 mL, 444 mmol), $K_2CO_3$ (614 mg, 4.44 mmol), N,N-dimethylethylenediamine (196 mg, 244 µL, 2.22 mmol) and ethyleneglycol (44.4 mL). The reaction was stirred for 6 h at 60° C. The reaction mixture was cooled, extracted with dichloromethane (3×25 mL), and then the combined organics were dried over magnesium sulfate. The mixture was concentrated in vacuo then purified by chromatography (silica gel 50 µm, 40 g, Analogix, 0 to 5% of a 9:1 MeOH:NH$_4$OH solution in CH$_2$Cl$_2$, 20 min) to obtain 2-(6-aminopyridin-2-yl)-2-methylpropanenitrile (3.2 g, 89%) as a white solid. $^1$H NMR (CHLOROFORM-d) δ: 7.34-7.46 (m, 1H), 6.81 (d, J=7.2 Hz, 1H), 6.40 (d, J=7.9 Hz, 1H), 4.67 (br. s., 2H), 1.63-1.68 (m, 6H); MS (EI/CI) m/z: 162.1 [M+H].

Step 3

Ethyl 6-chloro-4-(6-(2-cyanopropan-2-yl)pyridin-2-ylamino)pyridazine-3-carboxylate

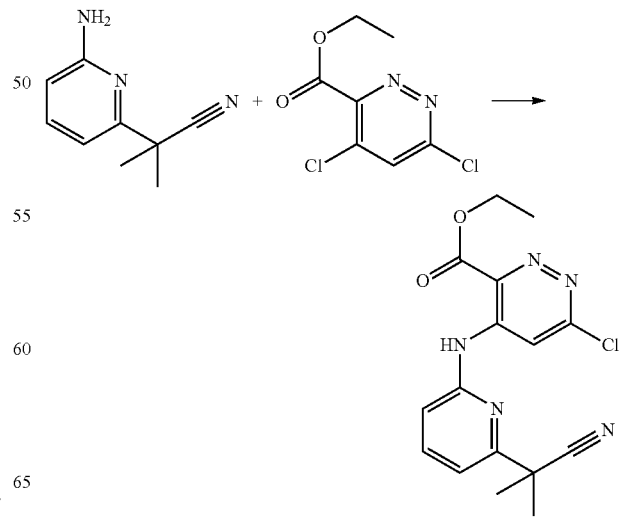

A mixture of ethyl 4,6-dichloropyridazine-3-carboxylate (1.4 g, 6.33 mmol) and 2-(6-aminopyridin-2-yl)-2-methyl-propanenitrile (2.04 g, 12.7 mmol) was dissolved in acetonitrile (3 mL) and heated to 130° C. for 18 h. The mixture was cooled, concentrated, and the residue then adsorbed on silica gel and purified by chromatography (silica gel 45 μM, 160 g, Thomson, 0 to 20% acetone in dichloromethane, 20 min). The fractions containing the desired product were collected, concentrated and then the residue obtained was recrystallized from dichloromethane, filtered and dried to give ethyl 6-chloro-4-(6-(2-cyanopropan-2-yl)pyridin-2-ylamino) pyridazine-3-carboxylate (792 mg, 36%) as an off white solid. $^1$H NMR (CHLOROFORM-d) δ: 10.86 (s, 1H), 9.27 (s, 1H), 7.75 (t, J=7.9 Hz, 1H), 7.26 (d, J=7.9 Hz, 1H), 6.90 (d, J=7.9 Hz, 1H), 4.58 (q, J=7.2 Hz, 2H), 1.81 (s, 6H), 1.52 (t, J=7.2 Hz, 3H); MS (EI/CI) m/z: 346.1 [M+H].

Step 4

6-Chloro-4-(6-(2-cyanopropan-2-yl)pyridin-2-ylamino)pyridazine-3-carboxamide

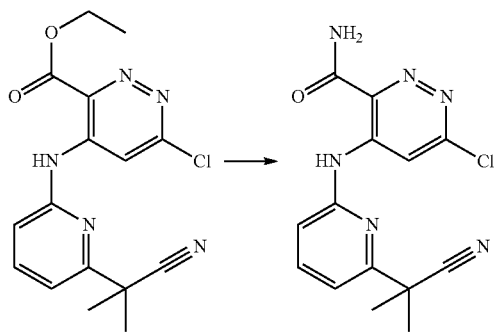 [SMILES: CCOC(=O)c1nnc(Cl)cc1Nc1cccc(C(C)(C)C#N)n1 ; CC(C)(C#N)c1cccc(Nc2cc(Cl)nnc2C(N)=O)n1]

Ethyl 6-chloro-4-(6-(2-cyanopropan-2-yl)pyridin-2-ylamino)pyridazine-3-carboxylate (792 mg, 2.29 mmol) was suspended in ammonia (7M in methanol, 7.87 g, 10.0 mL, 70.0 mmol), then the flask was sealed and stirred at r.t. for 18 h. The solid formed during the reaction was collected by filtration, the filter cake rinsed with methanol and then dried under high vacuum to give 6-chloro-4-(6-(2-cyanopropan-2-yl)pyridin-2-ylamino)pyridazine-3-carboxamide (581 mg, 80%) as an off-white solid. $^1$H NMR (DMSO-$d_6$) δ: 12.14 (s, 1H), 9.22 (s, 1H), 8.89 (s, 1H), 8.23 (s, 1H), 7.87 (t, J=7.9 Hz, 1H), 7.27 (d, J=7.6 Hz, 1H), 7.10 (d, J=7.9 Hz, 1H), 1.73 (s, 6H); MS (EI/CI) m/z: 316.9 [M+H].

Step 5

6-(2-Aminoethylamino)-4-(6-(2-cyanopropan-2-yl) pyridin-2-ylamino)pyridazine-3-carboxamide

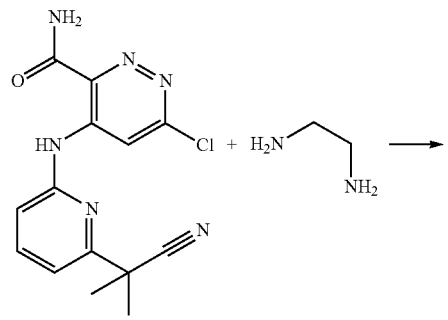

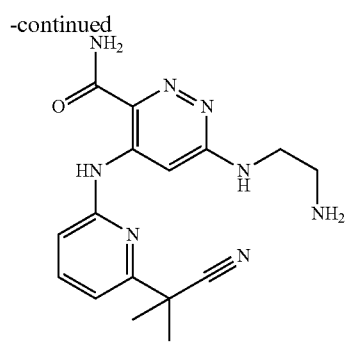

A flask was charged with 6-chloro-4-(6-(2-cyanopropan-2-yl)pyridin-2-ylamino)pyridazine-3-carboxamide (100 mg, 316 μmol) and NMP (1 mL). To this solution was added ethylenediamine (190 mg, 213 μL, 3.16 mmol) and the reaction mixture was heated with stirring at 120° C. for 1 h. The mixture was concentrated using a Kugelrohr distillation apparatus under high vacuum and at 120° C. to afford a light brown solid. This solid was purified by chromatography (spherical silica 20-45 μM, 23 g, Versaflash Supelco, 0 to 10% of a 9:1 MeOH:NH$_4$OH solution in CH$_2$Cl$_2$, 20 min) to give the title product. This was dissolved in hot EtOH and concentrated, then resuspended in cold EtOH, sonicated and the solid collected by decanting mother liquors. The solid residue was then dried under high vacuum to give 6-(2-aminoethylamino)-4-(6-(2-cyanopropan-2-yl)pyridin-2-ylamino)pyridazine-3-carboxamide (68 mg, 63%) as an off-white solid. $^1$H NMR (DMSO-$d_6$) δ: 11.94 (br. s., 1H), 8.41 (br. s., 1H), 7.98 (s, 1H), 7.77 (t, J=7.9 Hz, 1H), 7.68 (br. s., 1H), 7.15 (s, 2H), 6.92 (d, J=8.3 Hz, 1H), 3.36-3.45 (m, 3H), 2.75 (t, J=6.0 Hz, 2H), 1.73 (s, 6H), 1.40-1.68 (m, 2H); MS (EI/CI) m/z: 341.1 [M+H].

Example 22

2-(3-Amino-propyl)-4-m-tolylamino-pyrimidine-5-carboxylic acid amide

Step 1

4-(1,3-Dioxo-1,3-dihydro-isoindol-2-yl)-butyronitrile

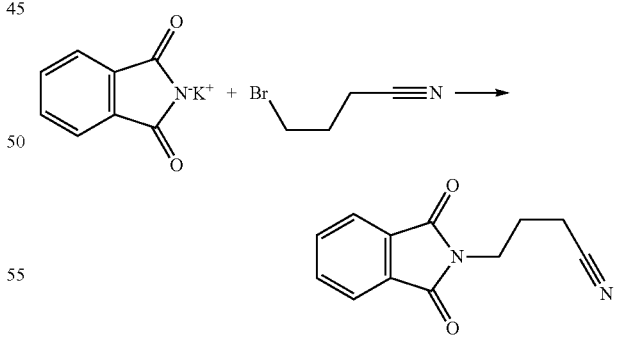

To a stirred suspension of potassium phthalimide (10.0 g, 54.0 mmol) in DMSO (80 mL) was added 4-bromo-butyronitrile (5.4 mL, 54.0 mmol). After 72 h, ethyl acetate (400 mL) was added and the mixture was washed with water (2×500 mL) and brine (200 mL). The organic phase was dried then concentrated in vacuo to obtain a crude mass which was purified by chromatography (silica, 0 to 30% ethyl acetate in hexane) to give pure 4-(1,3-dioxo-1,3-dihydro-isoindol-2-yl)-butyronitrile (6.7 g, 58%) as a white solid. MS (EI/CI) m/z: 232.2 [M+H].

Step 2

Ethyl 4-(1,3-dioxo-2,3-dihydro-1H-isoindol-2-yl)butanecarboximidate hydrochloride

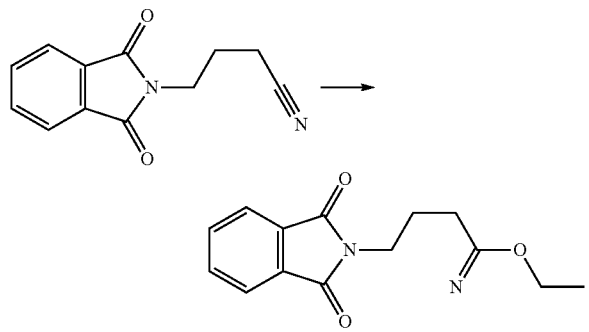

Hydrogen chloride gas was bubbled through a solution of 4-(1,3-dioxo-1,3-dihydro-isoindol-2-yl)-butyronitrile (1.0 g, 4.7 mmol) in a mixture of ethanol (25 mL) and chloroform (25 mL) at 5° C. for 45 min, then the mixture was stirred at room temperature for 2 h. The reaction mixture was concentrated under reduced pressure, then to the sticky crude mass was added diethyl ether (50 mL) and the mixture concentrated under reduced pressure to obtain ethyl 4-(1,3-dioxo-2,3-dihydro-1H-isoindol-2-yl)butanecarboximidate hydrochloride (100%) as a white solid. This was used in the next step directly without further purification.

Step 3

2-[3-(1,3-Dioxo-1,3-dihydro-isoindol-2-yl)-propyl]-4-hydroxy-pyrimidine-5-carboxylic acid ethyl ester

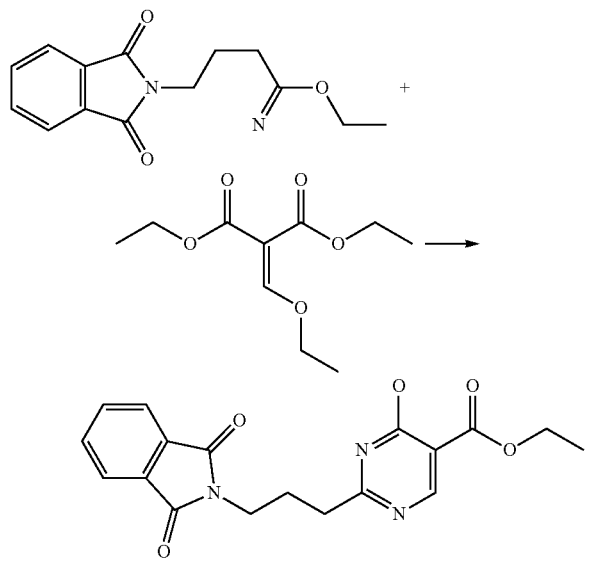

To a stirred suspension of ethyl 4-(1,3-dioxo-2,3-dihydro-1H-isoindol-2-yl)butanecarboximidate hydrochloride (4.7 mmol, material obtained from step 2), in ethanol (30 mL) was added ammonium acetate (513 mg, 9.3 mmol) and the mixture heated at reflux for 2 h. The reaction mixture was concentrated under reduced pressure, then ethanol (50 mL) was added to the residue obtained. NaOMe (1.26 g, 23.3 mmol) and 2-ethoxymethylene-malonic acid diethyl ester (1.9 mL, 9.3 mmol) were added then the mixture was stirred at room temperature for 17 h. The reaction mixture was concentrated under vacuum and then the residue was acidified with aqueous HCl (1 M) until it reached pH 1. The mixture was extracted with ethyl acetate (2×50 mL), and then the organic extracts were combined, washed with water (25 mL) then brine (25 mL), dried, filtered and concentrated under reduced pressure. The crude material obtained was purified by chromatography (silica, ethyl acetate and hexane) to give 2-[3-(1,3-dioxo-1,3-dihydro-isoindol-2-yl)-propyl]-4-hydroxy-pyrimidine-5-carboxylic acid ethyl ester (210 mg, 13%) (two steps) as white solid. MS (EI/CI) m/z: 354.2 [M+H].

Step 4

4-Chloro-2-[3-(1,3-dioxo-1,3-dihydro-isoindol-2-yl)-propyl]-pyrimidine-5-carboxylic acid ethyl ester

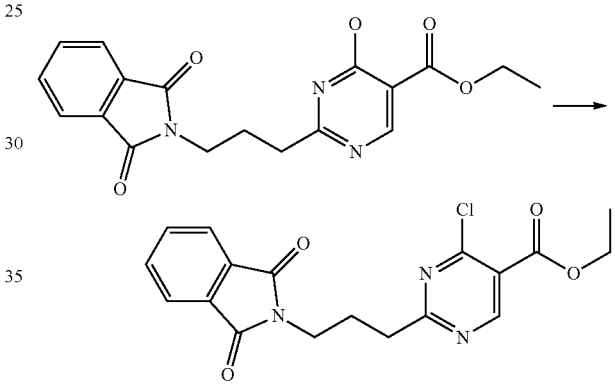

To a mixture of 2-[3-(1,3-dioxo-1,3-dihydro-isoindol-2-yl)-propyl]-4-hydroxy-pyrimidine-5-carboxylic acid ethyl ester (190 mg, 0.54 mmol) and POCl₃ (1.0 mL) was added diethylaniline (0.15 mL, 0.96 mmol) and the mixture stirred at 90° C. for 1 h. The mixture was cooled then poured into ice water. This was extracted with DCM (2×30 mL) and the combined organic extracts were washed with water (25 mL) and then brine (25 mL), dried over anhydrous sodium sulfate and filtered. The filtrate was used directly in the next step; considering quantitative yield.

Step 5

2-[3-(1,3-Dioxo-1,3-dihydro-isoindol-2-yl)-propyl]-4-m-tolylamino-pyrimidine-5-carboxylic acid ethyl ester

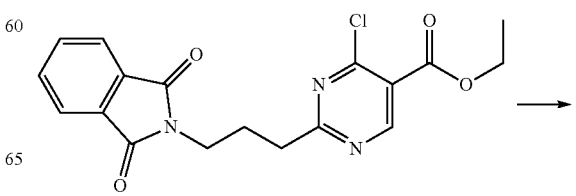

-continued

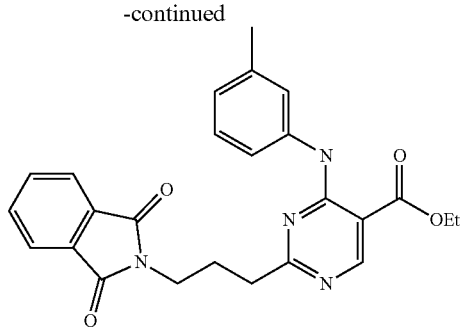

To the above filtrate containing 4-chloro-2-[3-(1,3-dioxo-1,3-dihydro-isoindol-2-yl)-propyl]-pyrimidine-5-carboxylic acid ethyl ester (~0.54 mmol) was added m-toluidine (0.145 mL, 1.34 mmol) and then the mixture concentrated in vacuo at 40° C. over 20 min. The crude mass was purified by chromatography (silica, 15% to 30% ethyl acetate in hexanes) to give 2-[3-(1,3-dioxo-1,3-dihydro-isoindol-2-yl)-propyl]-4-m-tolylamino-pyrimidine-5-carboxylic acid ethyl ester (145 mg, 61%) as and off white sticky solid. MS (EI/CI) m/z: 444.6 [M+H].

Step 6

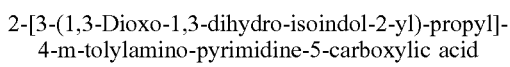

2-[3-(1,3-Dioxo-1,3-dihydro-isoindol-2-yl)-propyl]-4-m-tolylamino-pyrimidine-5-carboxylic acid

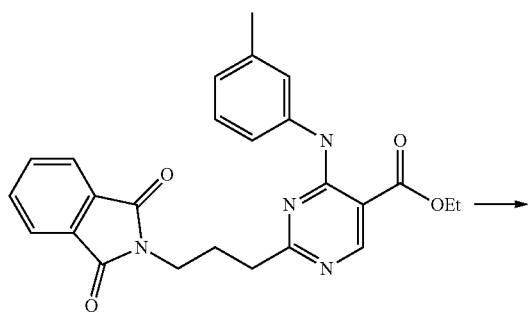

Aqueous NaOH (1M, 0.32 mL, 0.32 mmol) was added to a solution of 2-[3-(1,3-dioxo-1,3-dihydro-isoindol-2-yl)-propyl]-4-m-tolylamino-pyrimidine-5-carboxylic acid ethyl ester (70 mg, 0.16 mmol) in ethanol (2 mL) and THF (2 mL). After stirring at room temperature for 4 h, the reaction mixture was acidified with 1M HCl until it reached pH 1, then extracted with ethyl acetate (2×25 mL). The combined organic extracts were washed with water (20 mL) and brine (20 mL), then dried and concentrated under vacuum to give 2-[3-(1,3-dioxo-1,3-dihydro-isoindol-2-yl)-propyl]-4-m-tolylamino-pyrimidine-5-carboxylic acid (64 mg, 98%) as off white solid. MS (EI/CI) m/z: 433.0 [M+H$_2$O].

Step 7

2-[3-(1,3-Dioxo-1,3-dihydro-isoindol-2-yl)-propyl]-4-m-tolylamino-pyrimidine-5-carboxylic acid amide

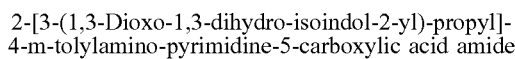

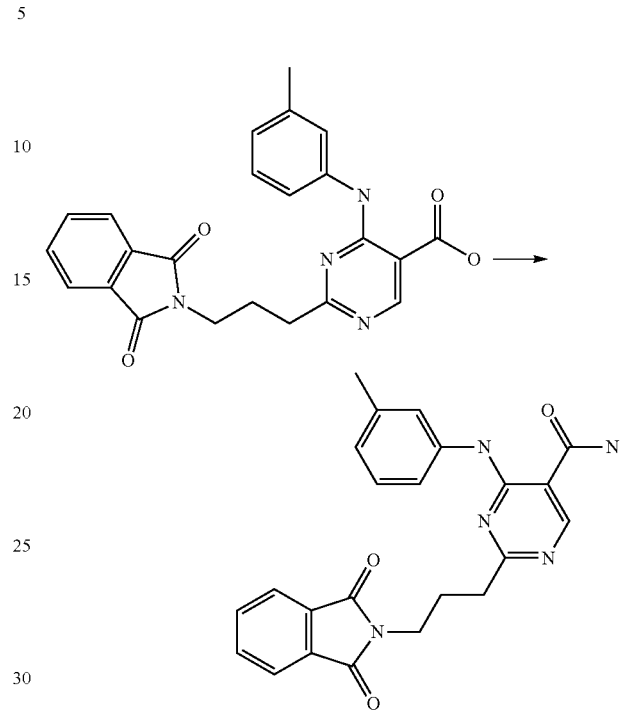

EDCI (33 mg, 0.17 mmol) and HOBT (23 mg, 0.17 mmol) were added to a solution of 2-[3-(1,3-dioxo-1,3-dihydro-isoindol-2-yl)-propyl]-4-m-tolylamino-pyrimidine-5-carboxylic acid (60 mg, 0.14 mmol) in DMF (5 mL) and the mixture stirred at room temperature for 1 h. An aqueous solution of NH$_4$OH (25%; 0.11 mL) was added and the reaction mixture was stirred for 16 h. The reaction mixture was diluted with ethyl acetate (30 mL), washed with water (2×20 mL), and brine (20 mL). The organic phase was dried, concentrated under reduced pressure and then purified by chromatography (silica) to give 2-[3-(1,3-dioxo-1,3-dihydro-isoindol-2-yl)-propyl]-4-m-tolylamino-pyrimidine-5-carboxylic acid amide (10 mg, 17%) as a yellow sticky solid. MS (EI/CI) m/z: 416.0 [M+H].

Step 8

2-(3-Amino-propyl)-4-m-tolylamino-pyrimidine-5-carboxylic acid amide

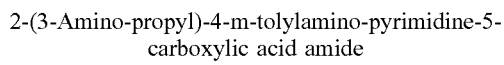

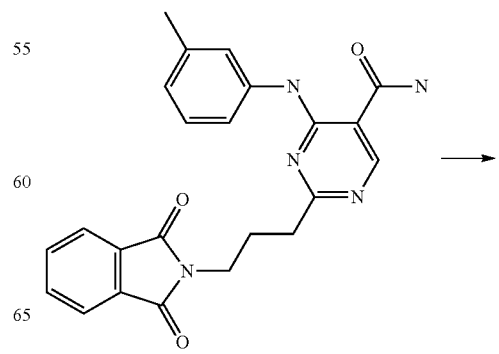

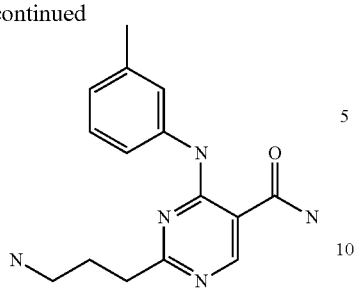

To a stirred solution of 2-[3-(1,3-dioxo-1,3-dihydro-isoindol-2-yl)-propyl]-4-m-tolylamino-pyrimidine-5-carboxylic acid amide (40 mg, 0.1 mmol) in methanol (2.5 mL) was added hydrazine monohydrate (0.04 mL; 0.82 mmol) and the mixture stirred at room temperature for 6 h. The mixture was concentrated under vacuum, then the crude residue was purified by preparative HPLC [Column; Xterra RP 18; Mobile phase; $NH_4OH$ (0.1% in water) in ACN] to give 2-(3-amino-propyl)-4-m-tolylamino-pyrimidine-5-carboxylic acid amide (5 mg, 18%) as a yellow solid. $^1H$ NMR (400 MHz, MeOD) δ ppm 8.69 (s, 1H), 7.57 (d, J=7.9 Hz, 1H), 7.48 (s, 1H), 7.23 (t, J=7.8 Hz, 1H), 6.93 (d, J=7.6 Hz, 1H), 2.85 (t, J=7.5 Hz, 2H), 2.76 (t, J=7.2 Hz, 2H), 2.35 (s, 3H), 2.00 (app. quintet, J=7.4 Hz, 2H); MS (EI/CI) m/z: 286.2 [M+H].

Example 23

6-(2-Aminoethylamino)-4-(6-(2-hydroxypropan-2-yl)pyridin-2-ylamino)pyridazine-3-carboxamide Step 1

2-(6-Bromopyridin-2-yl)propan-2-ol

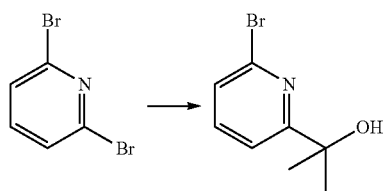

A dry 250 mL round bottomed flask fitted with a stir bar and septum was charged with n-butyllithium 1.6 M in hexane (30.3 mL, 48.5 mmol), the flask was cooled in a dry-ice acetone bath to −76° C. then THF (30 mL) was added followed by a solution of 2,6-dibromopyridine (11.5 g, 48.5 mmol) in THF (60 mL) slowly via cannula over 15 min. The dark yellow-brown solution was stirred for 30 minutes in the dry-ice bath, then propan-2-one (4.75 g, 6 mL, 81.7 mmol) was added. The deep green solution was stirred in the dry-ice bath for 15 minutes then was warmed to room temperature over 1 hour. A saturated aqueous solution of ammonium chloride (100 mL) was carefully added and the mixture extracted with dichloromethane (3×200 mL). The combined organic extracts were dried over magnesium sulfate then concentrated in vacuo and purified by chromatography (silica gel 50 μm, 150 g, Analogix, eluting with 0 to 50% dichloromethane in hexanes) to obtain 2-(6-bromopyridin-2-yl)propan-2-ol (9.9 g, 94%) as a light yellow, clear liquid. $^1H$ NMR (CHLOROFORM-d) δ: 7.52- 7.59 (m, 1H), 7.33-7.40 (m, 2H), 4.05 (br. s., 1H), 1.55 (s, 6H); MS (EI/CI) m/z: 216.1, 218.1 [M+H].

Step 2

2-(6-Aminopyridin-2-yl)propan-2-ol

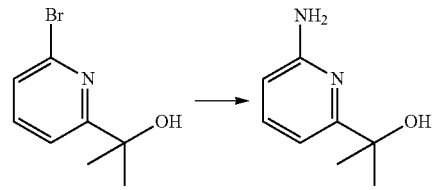

A heavy walled sealable tube was loaded under an argon atmosphere with copper (I) oxide (53.0 mg, 370 μmol), 2-(6-bromopyridin-2-yl)propan-2-ol (1600 mg, 7.4 mmol), ammonium hydroxide 28% solution (16.5 M, 9.0 mL, 148 mmol), $K_2CO_3$ (205 mg, 1.48 mmol), N,N-dimethylethylenediamine (65 mg, 81 μL, 740 μmol) and ethyleneglycol (14.8 mL). The reaction was stirred for 6 h at 60° C., then cooled to room temperature and extracted with dichloromethane (3×25 mL). The combined organic extracts were dried over magnesium sulfate, concentrated in vacuo and then purified by chromatography (spherical silica 20-45 μM, 23 g, Versaflash Supelco, eluting with 0 to 5% of a 1:9 ammonium hydroxide:methanol solution in dichloromethane, 20 min) to obtain 2-(6-aminopyridin-2-yl)propan-2-ol (626 mg, 56%) as a light yellow liquid. $^1H$ NMR (CHLOROFORM-d) δ: 7.44 (t, J=7.7 Hz, 1H), 6.67 (d, J=7.6 Hz, 1H), 6.38 (d, J=7.9 Hz, 1H), 5.12 (s, 1H), 4.38-4.55 (m, 2H), 1.49 (s, 6H); MS (EI/CI) m/z: 153.1, 155.1 [M+H].

Step 3

Ethyl 6-chloro-4-(6-(2-hydroxypropan-2-yl)pyridin-2-ylamino)pyridazine-3-carboxylate

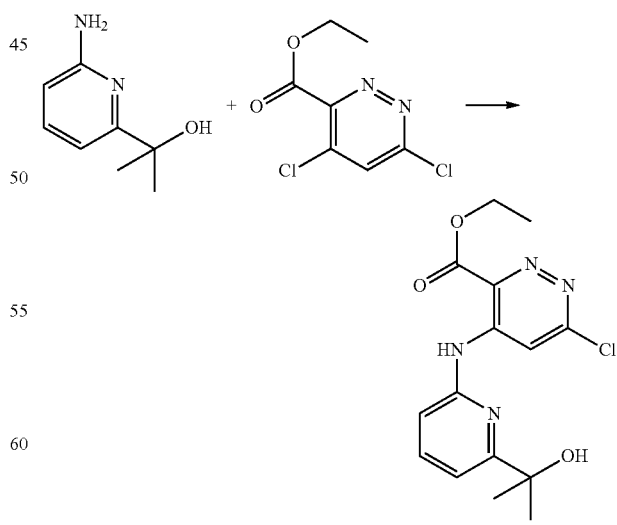

A mixture of ethyl 4,6-dichloropyridazine-3-carboxylate (0.45 g, 2.04 mmol) and 2-(6-aminopyridin-2-yl)propan-2-ol (620 mg, 4.07 mmol) was dissolved in acetonitrile (3 mL)

and heated at 130° C. for 18 h. The mixture was cooled, concentrated, then the residue was adsorbed on silica gel and purified by chromatography (silica gel 45 μM, 160 g, Thomson, eluting with 0 to 100% ethyl acetate in hexanes, 40 min) to yield ethyl 6-chloro-4-(6-(2-hydroxypropan-2-yl)pyridin-2-ylamino)pyridazine-3-carboxylate (405 mg, 59%). $^1$H NMR (CHLOROFORM-d) δ: 10.72 (s, 1H), 9.00 (s, 1H), 7.76 (t, J=7.9 Hz, 1H), 7.34 (d, J=7.9 Hz, 1H), 6.89 (d, J=7.9 Hz, 1H), 5.21 (br. s., 1H), 4.60 (q, J=7.2 Hz, 2H), 1.67 (s, 6H), 1.54 (t, J=7.9 Hz, 3H); MS (EI/CI) m/z: 337.0, 339.0 [M+H].

Step 4

6-Chloro-4-(6-(2-hydroxypropan-2-yl)pyridin-2-ylamino)pyridazine-3-carboxamide

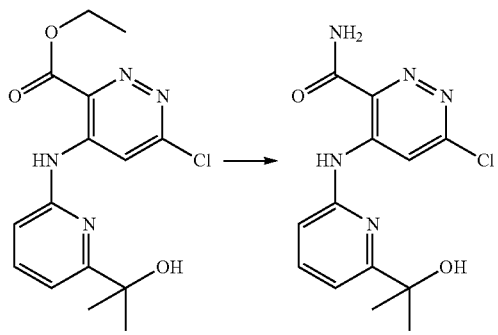 [SMILES: CCOC(=O)c1nnc(Cl)cc1Nc1cccc(C(C)(C)O)n1 ; CC(C)(O)c1cccc(Nc2cc(Cl)nnc2C(N)=O)n1]

Ethyl 6-chloro-4-(6-(2-hydroxypropan-2-yl)pyridin-2-ylamino)pyridazine-3-carboxylate (792 mg, 2.35 mmol) was suspended in ammonia (7M in methanol, 7.87 g, 10.0 mL, 70.0 mmol), then the flask was sealed and stirred at r.t. for 5 h. The mixture was concentrated in vacuo and the residue obtained was purified by chromatography (spherical silica 20-45 μM, 50 g, Versaflash Supelco, 0 to 5% of a 9:1 MeOH:NH$_4$OH solution in CH$_2$Cl$_2$, 20 min) to give 6-chloro-4-(6-(2-hydroxypropan-2-yl)pyridin-2-ylamino)pyridazine-3-carboxamide (241 mg, 33%) as an off-white solid. $^1$H NMR (CHLOROFORM-d) δ: 11.64 (s, 1H), 8.96 (s, 1H), 8.18 (br. s., 1H), 7.71 (t, J=7.9 Hz, 1H), 7.25 (d, J=7.6 Hz, 1H), 6.86 (d, J=8.3 Hz, 1H), 5.70 (br. s., 1H), 1.64 (s, 6H); MS (EI/CI) m/z: 308.0, 310.0 [M+H].

Step 5

6-(2-Aminoethylamino)-4-(6-(2-hydroxypropan-2-yl)pyridin-2-ylamino)pyridazine-3-carboxamide

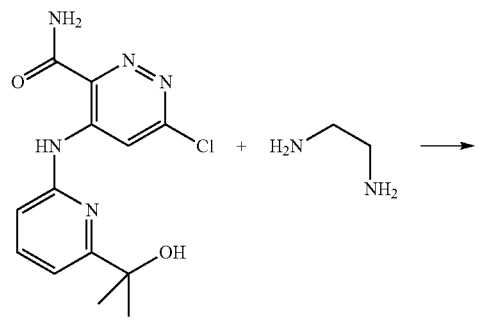

To a stirred solution of 6-chloro-4-(6-(2-hydroxypropan-2-yl)pyridin-2-ylamino)pyridazine-3-carboxamide (127 mg, 413 μmol) in NMP (1 mL) was added ethylenediamine (248 mg, 279 μL, 4.13 mmol) and the reaction mixture heated at 120° C. for 1.5 h. The mixture was concentrated using a Kugelrohr distillation apparatus under high vacuum at 120° C. to afford a light brown solid. The crude solid was purified by chromatography (spherical silica 20-45 μM, 23 g, Versaflash Supelco), 0 to 10% of a 9:1 MeOH:NH$_4$OH solution in CH$_2$Cl$_2$, 20 min) to give the title compound which was dissolved in hot EtOH and then concentrated. The residual solid was suspended in cold EtOH, sonicated and the solid separated by decanting mother liquor, then dried under high vacuum to give 6-(2-aminoethylamino)-4-(6-(2-hydroxypropan-2-yl)pyridin-2-ylamino)pyridazine-3-carboxamide (57 mg, 42%) as an off-white solid. $^1$H NMR (DMSO-d$_6$) δ: 11.74 (s, 1H), 8.37 (br. s., 1H), 7.96 (s, 1H), 7.58-7.72 (m, 2H), 7.21 (d, J=7.2 Hz, 2H), 6.75 (d, J=8.3 Hz, 1H), 5.17 (br. s., 1H), 3.27 (t, J=6.2 Hz, 2H), 2.75 (t, J=6.2 Hz, 2H), 1.50-1.65 (m, 2H), 1.48 (s, 6H); MS (EI/CI) m/z: 332.1 [M+H].

Example 24

6-(2-aminoethylamino)-4-(4,6-dimethylpyrimidin-2-ylamino)pyridazine-3-carboxamide Step 1

Ethyl 6-chloro-4-(4,6-dimethylpyrimidin-2-ylamino)pyridazine-3-carboxylate

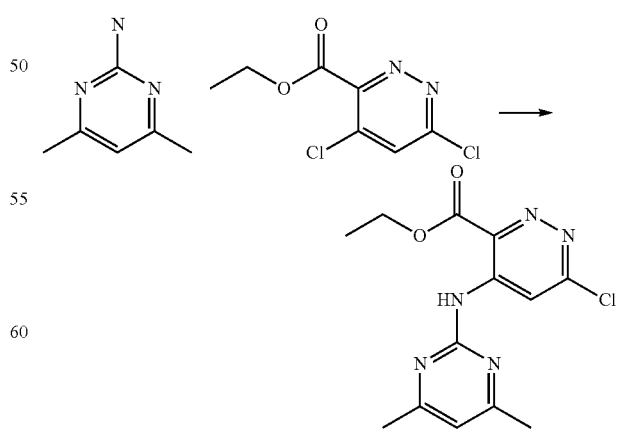

A microwave vessel was charged with 4,6-dimethylpyrimidin-2-amine (682 mg, 5.54 mmol), ethyl 4,6-dichloropyridazine-3-carboxylate (0.306 g, 1.38 mmol) and acetonitrile (0.50 mL). The mixture was and heated under microwave irradiation at 150° C. for 3 h. After cooling, the mixture was adsorbed on silica gel and purified by chromatography (silica gel 45 μM, 80 g, Thomson, eluting with 0 to 10% of a 9:1 MeOH:NH₄OH solution in CH₂Cl₂, 20 min) to give ethyl 6-chloro-4-(4,6-dimethylpyrimidin-2-ylamino) pyridazine-3-carboxylate (85 mg) as a brown foam which was ~60% pure and used directly in the next reaction without further purification.

Step 2

6-Chloro-4-(4,6-dimethylpyrimidin-2-ylamino) pyridazine-3-carboxamide

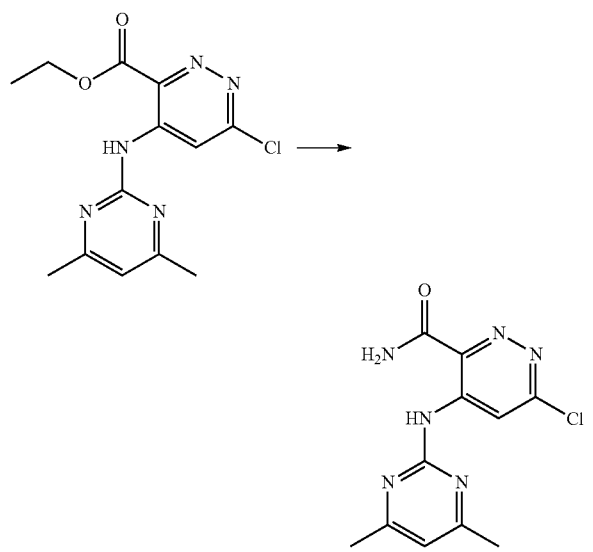

A flask was charged with ethyl 6-chloro-4-(4,6-dimethylpyrimidin-2-ylamino)pyridazine-3-carboxylate (85 mg, 276 μmol) and 7M ammonia in methanol (7.87 g, 10.0 mL, 70.0 mmol). The flask was sealed and stirred at room temperature for 5 h. The yellow solid was collected by filtration, rinsed with methanol and dried to give 6-chloro-4-(4,6-dimethylpyrimidin-2-ylamino)pyridazine-3-carboxamide (20 mg, 71.8 μmol, 5% yield for two steps) as a yellow solid. ¹H NMR (DMSO-d₆) δ: 12.10 (s, 1H), 9.10 (s, 1H), 8.88 (s, 1H), 8.24 (s, 1H), 6.95 (s, 1H), 2.40 (s, 6H); MS (EI/CI) m/z: 306.0, 308.0 [M+H].

Step 3

6-(2-Aminoethylamino)-4-(4,6-dimethylpyrimidin-2-ylamino)pyridazine-3-carboxamide

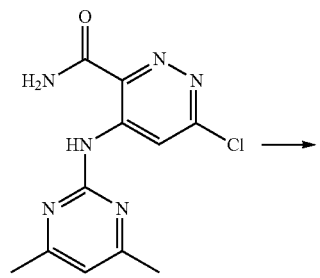

A flask was charged with 6-chloro-4-(4,6-dimethylpyrimidin-2-ylamino)pyridazine-3-carboxamide (20 mg, 71.8 μmol) and DMSO (1 mL). To this solution was added ethylenediamine (43.1 mg, 48.5 μL, 718 μmol) and the reaction mixture was heated with stirring at 120° C. for 45 min. The solvent was removed under high vacuum, and the crude material obtained was purified by chromatography (spherical silica 20-45 μM, 23 g, Versaflash Supelco, eluting with 0 to 10% of a 9:1 MeOH:NH₄OH solution in CH₂Cl₂, 20 min) to give 6-(2-aminoethylamino)-4-(4,6-dimethylpyrimidin-2-ylamino)pyridazine-3-carboxamide (11 mg, 36 μmol, 51%) as a light yellow solid. ¹H NMR (CHLOROFORM-d) δ: 11.63 (s, 1H), 8.34 (s, 1H), 8.01 (br. s., 1H), 6.63 (s, 1H), 5.44 (br. s., 3H), 3.51-3.61 (m, 3H), 3.06 (t, J=6.0 Hz, 2H), 2.43 (s, 6H), 1.69 (br. s., 4H); MS (EI/CI) m/z: 303.1 [M+H].

Example 25

6-(2-Aminoethylamino)-4-(6-(trifluoromethyl)pyridin-2-ylamino)pyridazine-3-carboxamide Step 1

Ethyl 6-chloro-4-(6-(trifluoromethyl)pyridin-2-ylamino)pyridazine-3-carboxylate

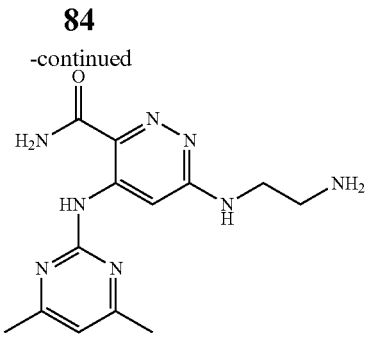

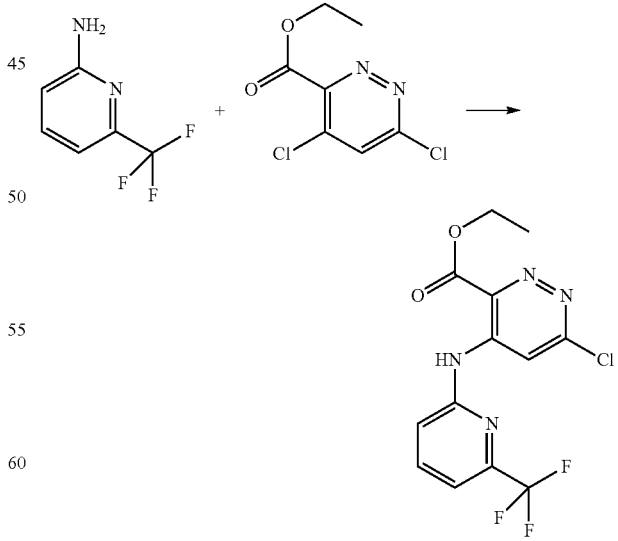

A mixture of ethyl 4,6-dichloropyridazine-3-carboxylate (400 mg, 1.81 mmol) and 6-(trifluoromethyl)pyridin-2-amine (587 mg, 3.62 mmol, available commercially from Aldrich), was dissolved in acetonitrile (3 mL) and heated at 120° C. for 24 h. The mixture was cooled, concentrated, and the residue was adsorbed on silica gel and purified by chromatography (silica gel 45 μM, 160 g, Thomson, eluting with 0 to 20% acetone in dichloromethane over 20 min) to give the desired ethyl 6-chloro-4-(6-(trifluoromethyl)pyridin-2-ylamino)pyridazine-3-carboxylate (116 mg, 19%). $^1$H NMR (CHLOROFORM-d) δ: 10.97 (s, 1H), 9.16 (s, 1H), 7.79 (t, J=7.9 Hz, 1H), 7.33 (d, J=7.6 Hz, 1H), 7.05 (d, J=8.3 Hz, 1H), 4.51 (q, J=7.2 Hz, 2H), 1.52 (br. s., 1H), 1.45 (t, J=7.2 Hz, 3H); MS (EI/CI) m/z: 347.0 [M+H].

Step 2

6-Chloro-4-(6-(trifluoromethyl)pyridin-2-ylamino)pyridazine-3-carboxamide

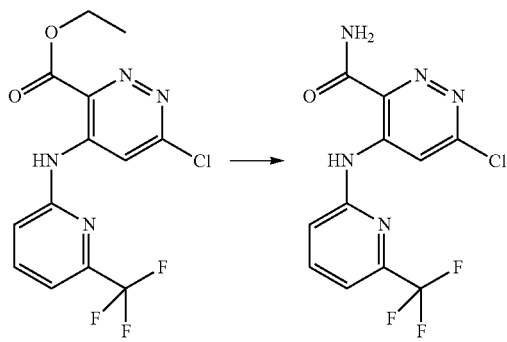 [SMILES: CCOC(=O)c1nnc(Cl)cc1Nc1cccc(C(F)(F)F)n1 ; NC(=O)c1nnc(Cl)cc1Nc1cccc(C(F)(F)F)n1]

Ethyl 6-chloro-4-(6-(trifluoromethyl)pyridin-2-ylamino)pyridazine-3-carboxylate (116 mg, 335 μmol) was suspended in ammonia (7M in methanol, 3.94 g, 5.0 mL, 35.0 mmol), the flask sealed, and the mixture stirred at r.t. for 6 h. The mixture was concentrated in vacuo then dried to give 6-chloro-4-(6-(trifluoromethyl)pyridin-2-ylamino)pyridazine-3-carboxamide (106 mg, 100%) as an off-white solid. $^1$H NMR (DMSO-d$_6$) δ: 12.30 (br. s., 1H), 8.85-9.10 (m, 2H), 8.28 (br. s., 1H), 8.05 (t, J=7.9 Hz, 1H), 7.58 (d, J=7.6 Hz, 1H), 7.46 (d, J=8.3 Hz, 1H); MS (EI/CI) m/z: 318.0 [M+H].

Step 3

6-(2-Aminoethylamino)-4-(6-(trifluoromethyl)pyridin-2-ylamino)pyridazine-3-carboxamide

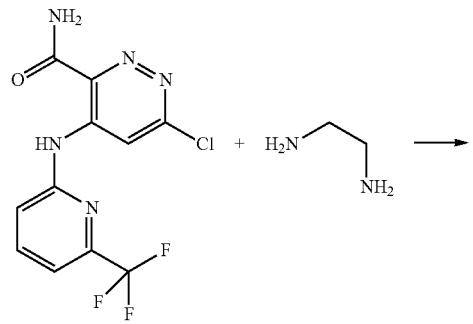

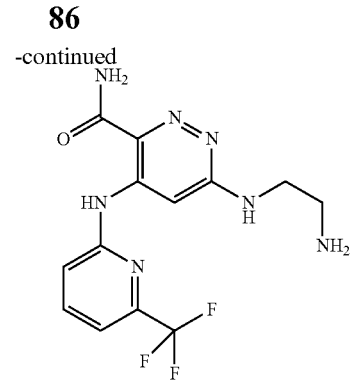

A flask was charged with 6-chloro-4-(6-(trifluoromethyl)pyridin-2-ylamino)pyridazine-3-carboxamide (106 mg, 334 μmol) and DMSO (1 mL), then to this solution was added ethylenediamine (201 mg, 225 μL, 3.34 mmol) and the reaction mixture heated with stirring at 120° C. for 1.5 h. The solvents were removed using a Kugelrohr distillation apparatus under high vacuum at 120° C. to afford a light brown solid. This crude solid was purified by chromatography (silica gel 50 μm, 40 g, Analogix, eluting with 0 to 10% of a 9:1 MeOH:NH$_4$OH solution in CH$_2$Cl$_2$, 15 min) to give the title compound. This was dissolved in hot EtOH and concentrated to dryness. The solid was suspended in cold EtOH, sonicated, and then separated by decanting mother liquor and finally dried under high vacuum to give 6-(2-aminoethylamino)-4-(6-(trifluoromethyl)pyridin-2-ylamino)pyridazine-3-carboxamide (66 mg, 58%) as an off-white solid. $^1$H NMR (DMSO-d$_6$) δ: 12.11 (br. s., 1H), 8.44 (br. s., 1H), 7.86-8.09 (m, 2H), 7.72 (br. s., 1H), 7.32-7.55 (m, 2H), 7.26 (d, J=8.3 Hz, 1H), 3.40-3.52 (m, 2H), 2.75 (t, J=5.9 Hz, 2H), 1.63 (br. s., 2H); MS (EI/CI) m/z: 342.0 [M+H].

Example 26

6-(2-Aminoethylamino)-4-(5-methoxy-6-propylpyridin-2-ylamino)pyridazine-3-carboxamide Step 1

2-Allyl-3-methoxy-6-nitropyridine

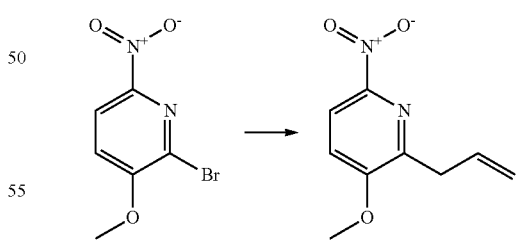

2-Bromo-3-methoxy-6-nitropyridine (3.22 g, 13.8 mmol), cesium fluoride (6.3 g, 41.5 mmol) and tetrakis(triphenylphosphine)palladium (0) (1.6 g, 1.38 mmol) were combined with 2-allyl-4,4,5,5-tetramethyl-1,3,2-dioxaborolane (2.55 g, 2.85 mL, 15.2 mmol) in THF (27 mL) and heated at 66° C. for 20 h. The mixture was cooled then diluted with water and ethyl acetate. The phases were separated then the organic phase was washed with water (2×) and brine, concentrated in vacuo and then purified by chromatography (silica, 10 to 50% ethyl acetate in hexanes) to give 2-allyl-3-methoxy-6-nitropyridine (2.0 g, 10.3 mmol, 75%) as a blue solid. MS (EI/CI) m/z: 194.8 [M+H].

Step 2

5-Methoxy-6-propylpyridin-2-amine

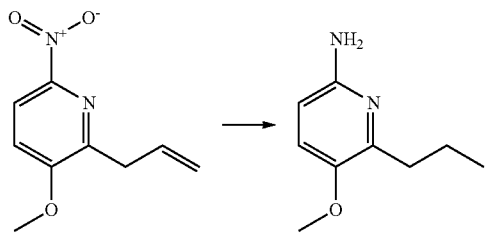

To a solution of 2-allyl-3-methoxy-6-nitropyridine (2.0 g, 10.3 mmol) in ethanol (34 mL) was added 10% palladium on carbon (219 mg, 2.06 mmol). The reaction was evacuated and back filled with hydrogen. This was repeated two more times. The reaction mixture was stirred under hydrogen at 1 atm for 16 h, then filtered through a pad of celite and the filter cake washed thoroughly with ethyl acetate. The filtrates were concentrated in vacuo and purified by chromatography (silica, 25 to 90% ethyl acetate in hexanes) to give 5-methoxy-6-propylpyridin-2-amine (1.41 g, 8.48 mmol, 82%) as an off white solid. $^1$H NMR (400 MHz, CHLOROFORM-$d_6$) δ ppm 7.09 (d, J=8.8 Hz, 1H), 6.38 (d, J=8.8 Hz, 1H), 4.28 (br. s, 2H), 3.77 (s, 3H), 2.68 (t, J=7.9 Hz, 2H), 1.69 (m, 2H), 0.99 (t, J=7.4 Hz, 3H); MS (EI/CI) m/z: 166.8 [M+H].

Step 3

Ethyl 6-chloro-4-(5-methoxy-6-propylpyridin-2-ylamino)pyridazine-3-carboxylate

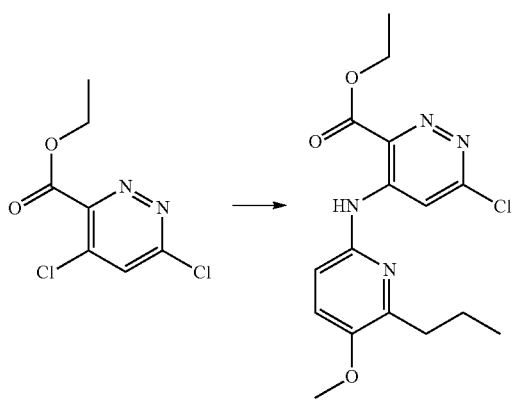 [SMILES: CCOC(=O)c1nnc(Cl)cc1Cl ; CCCc1nc(Nc2cc(Cl)nnc2C(=O)OCC)ccc1OC]

To a solution of ethyl 4,6-dichloropyridazine-3-carboxylate (1.9 g, 8.6 mmol) in acetonitrile (28.7 mL) was added 5-methoxy-6-propylpyridin-2-amine (1.43 g, 8.6 mmol) and the mixture heated at 70° C. for 72 h. The mixture was concentrated in vacuo then purified by chromatography (silica, 10 to 60% ethyl acetate in hexanes) to give ethyl 6-chloro-4-(5-methoxy-6-propylpyridin-2-ylamino)pyridazine-3-carboxylate (1.22 g, 3.48 mmol, 41%) as a yellow solid. $^1$H NMR (400 MHz, CHLOROFORM-$d_6$) δ ppm 10.58 (s, 1H), 8.84 (s, 1H), 7.25 (d, J=8.7 Hz, 1H), 6.88 (d, J=8.5 Hz, 1H), 4.58 (q, J=7.3 Hz, 2H), 3.88 (s, 3H), 2.87 (t, J=7.5 Hz, 2H), 1.84 (m, 2H), 1.52 (t, J=7.3 Hz, 3H), 1.05 (t, J=7.1 Hz, 3H); MS (EI/CI) m/z: 351.0 [M+H].

Step 4

6-Chloro-4-(5-methoxy-6-propylpyridin-2-ylamino)pyridazine-3-carboxamide

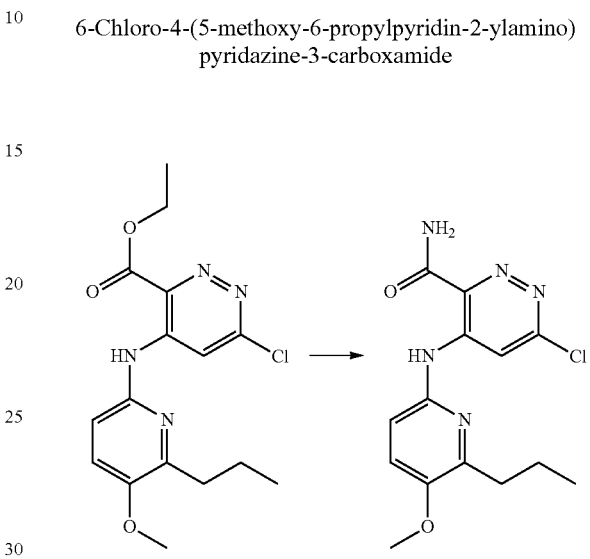

To a mixture of ethyl 6-chloro-4-(5-methoxy-6-propylpyridin-2-ylamino)pyridazine-3-carboxylate (1.22 g, 3.48 mmol) in methanol (10 mL) was added 7 N ammonia in methanol (23.6 g, 30 mL, 210 mmol) and the mixture stirred at 50° C. in a sealed tube for 16 h. The mixture was concentrated in vacuo to give 6-chloro-4-(5-methoxy-6-propylpyridin-2-ylamino)pyridazine-3-carboxamide (1.113 g, 3.46 mmol, 100%) as a yellow solid. $^1$H NMR (400 MHz, DMSO-$d_6$) δ ppm 11.72 (s, 1H), 8.89 (s, 1H), 8.77 (s, 1H), 8.13 (s, 1H), 7.47 (d, J=8.6 Hz, 1H), 7.01 (d, J=8.6 Hz, 1H), 3.81 (s, 3H), 2.74 (t, J=7.3 Hz, 2H), 1.75 (m, 2H), 0.97 (t, J=7.3 Hz, 3H); MS (EI/CI) m/z: 321.9 [M+H].

Step 5

6-(2-aminoethylamino)-4-(5-methoxy-6-propylpyridin-2-ylamino)pyridazine-3-carboxamide

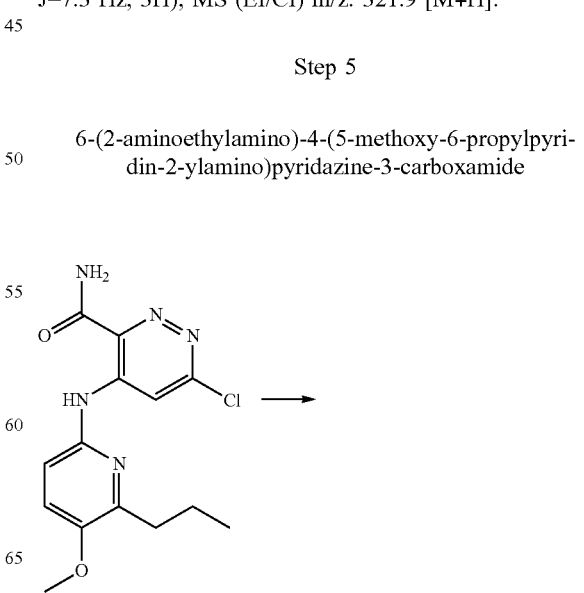

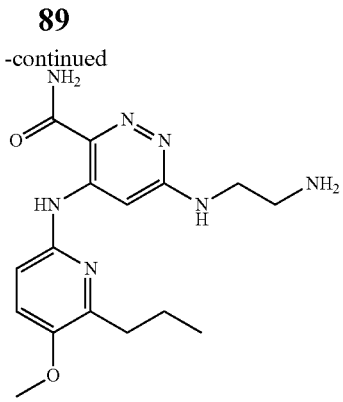

To a solution of 6-chloro-4-(5-methoxy-6-propylpyridin-2-ylamino)pyridazine-3-carboxamide (200 mg, 622 µmol) in NMP (2 mL) was added ethane-1,2-diamine (149 mg, 167 µL, 2.49 mmol) and the mixture heated to 100° C. for 16 h. The mixture was concentrated in vacuo and the residue purified by reverse phase chromatography (C-18; 10-100% water in acetonitrile gradient) followed by HPLC (C-18, 10-100% water in methanol gradient with NH$_4$OAc modifier). The solid obtained was recrystallized from water and filtered to give 6-(2-aminoethylamino)-4-(5-methoxy-6-propylpyridin-2-ylamino)pyridazine-3-carboxamide (80 mg, 232 µmol, 37%) as a light yellow solid. $^1$H NMR (400 MHz, DMSO-d$_6$) δ ppm 11.40 (s, 1H), 8.30 (s, 1H), 7.77 (s, 1H), 7.56 (s, 1H), 7.41 (d, J=8.5 Hz, 1H), 7.09 (t, J=5.4 Hz, 1H), 6.83 (d, J=8.5 Hz, 1H), 3.78 (s, 3H), 2.77 (t, J=6.2 Hz, 2H), 2.71 (t, J=7.5 Hz, 2H), 1.70 (m, 2H), 0.94 (t, J=7.4 Hz, 3H); MS (EI/CI) m/z: 346.2 [M+H].

Example 27

6-(2-Aminoethylamino)-4-(6-(dimethylamino)-5-methylpyridin-2-ylamino)pyridazine-3-carboxamide Step 1

N2,N2,3-Trimethylpyridine-2,6-diamine

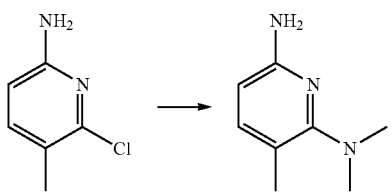

A microwave vial was charged with a mixture of 6-chloro-5-methylpyridin-2-amine (800 mg, 5.61 mmol, available commercially from Ark Pharm, Inc.) and dimethylamine (40% in water, 3.56 g, 4.00 mL, 31.6 mmol). The mixture was heated at 170° C. in a microwave for 5 h. The mixture was cooled and concentrated in vacuo, then purified by chromatography (spherical silica 20-45 µM, 120 g, Teledyne Isco, eluting with 0 to 20% acetone in dichloromethane over 20 min) to give N2,N2,3-trimethylpyridine-2,6-diamine (408 mg, 48%). $^1$H NMR (CHLOROFORM-d) δ: 7.15 (d, J=7.6 Hz, 1H), 6.04 (d, J=7.9 Hz, 1H), 4.11 (br. s., 2H), 2.80 (s, 6H), 2.17 (s, 3H). MS (EI/CI) m/z: 152.1 [M+H].

Step 2

Ethyl 6-chloro-4-(6-(dimethylamino)-5-methylpyridin-2-ylamino)pyridazine-3-carboxylate

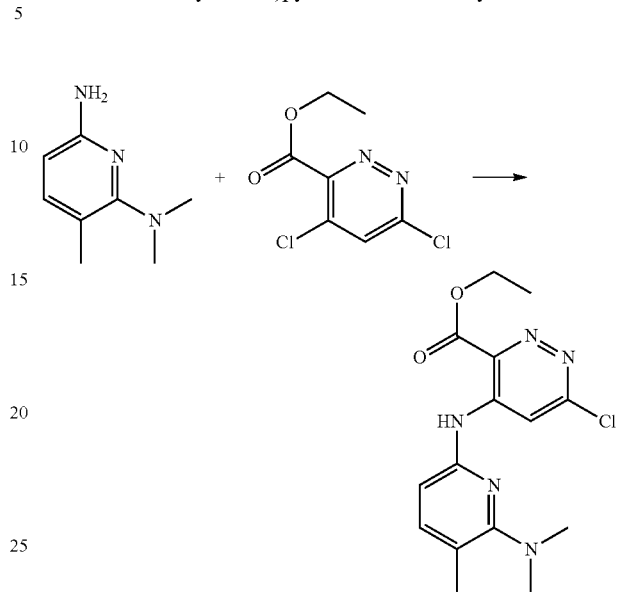

A mixture of ethyl 4,6-dichloropyridazine-3-carboxylate (0.373 g, 1.69 mmol) and N2,N2,3-trimethylpyridine-2,6-diamine (511 mg, 3.38 mmol) was dissolved in acetonitrile (2 mL) and heated at 90° C. for 72 h. The mixture was cooled, concentrated, and the residue obtained purified by chromatography (spherical silica 20-45 µM, 50 g, Versaflash Supelco, 0 to 20% acetone in dichloromethane, 20 min) to yield ethyl 6-chloro-4-(6-(dimethylamino)-5-methylpyridin-2-ylamino)pyridazine-3-carboxylate (428 mg, 76%) as a dense yellow liquid. $^1$H NMR (CHLOROFORM-d) δ: 10.49 (s, 1H), 9.27 (s, 1H), 7.35 (d, J=7.9 Hz, 1H), 6.41 (d, J=7.9 Hz, 1H), 4.55 (q, J=7.2 Hz, 2H), 2.91-3.00 (m, 6H), 2.27 (s, 3H), 1.50 (t, J=7.2 Hz, 3H); MS (EI/CI) m/z: 336.0 [M+H].

Step 3

6-Chloro-4-(6-(dimethylamino)-5-methylpyridin-2-ylamino)pyridazine-3-carboxamide

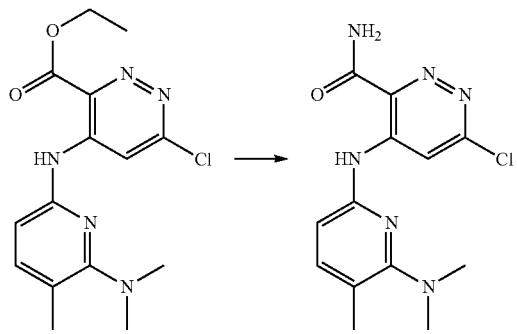 [SMILES: CCOC(=O)c1nnc(Cl)cc1Nc1ccc(C)c(N(C)C)n1 ; Cc1ccc(Nc2cc(Cl)nnc2C(N)=O)nc1N(C)C]

Ethyl 6-chloro-4-(6-(dimethylamino)-5-methylpyridin-2-ylamino)pyridazine-3-carboxylate (428 mg, 1.27 mmol) was suspended in ammonia (7M in methanol, 7.87 g, 10.0 mL, 70.0 mmol), the flask sealed and stirred at r.t. for 18 h. The abundant solid that was formed during the reaction was separated by filtration, the filter cake rinsed with methanol and dried under high vacuum to give 6-chloro-4-(6-(dimethylamino)-5-methylpyridin-2-ylamino)pyridazine-3-carboxamide (355 mg, 91%) as a light yellow solid. ¹H NMR (DMSO-d₆) δ: 11.76 (s, 1H), 9.13 (s, 1H), 8.80 (br. s., 1H), 8.15 (br. s., 1H), 7.44 (d, J=7.9 Hz, 1H), 6.51 (d, J=7.9 Hz, 1H), 2.85 (s, 6H), 2.20 (s, 3H); MS (EI/CI) m/z: 307.0 [M+H].

Step 4

6-(2-Aminoethylamino)-4-(6-(dimethylamino)-5-methylpyridin-2-ylamino)pyridazine-3-carboxamide

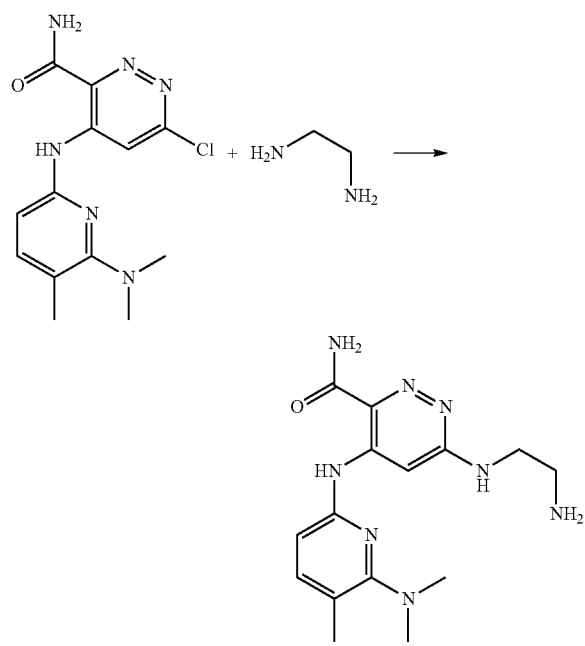

A flask was charged with 6-chloro-4-(6-(dimethylamino)-5-methylpyridin-2-ylamino)pyridazine-3-carboxamide (155 mg, 505 μmol) and DMSO (1 mL). To this solution was added ethylenediamine (304 mg, 341 μL, 5.05 mmol) and the reaction mixture was heated with stirring at 120° C. for 1.5 h. The mixture was concentrated using a Kugelrohr distillation apparatus under high vacuum and at 120° C. to afford a light brown solid. The crude solid was purified by chromatography (spherical silica 20-45 μM, 50 g, Versaflash Supelco, 0 to 10% of a 9:1 MeOH:NH₄OH solution in CH₂Cl₂) to give the title compound. This was dissolved in hot EtOH and concentrated to dryness. The solid was recrystallized from hot EtOH, filtered, the filter cake rinsed with fresh EtOH and finally dried under high vacuum to give 6-(2-aminoethylamino)-4-(6-(dimethylamino)-5-methylpyridin-2-ylamino)pyridazine-3-carboxamide (125 mg, 75%) as a white solid. ¹H NMR (DMSO-d₆) δ: 11.51 (br. s., 1H), 8.34 (br. s., 1H), 7.82 (s, 1H), 7.59 (br. s., 1H), 7.37 (d, J=7.9 Hz, 1H), 7.07 (br. s., 1H), 6.38 (d, J=7.6 Hz, 1H), 3.28 (m, 2H), 2.83 (s, 6H), 2.73 (t, J=6.0 Hz, 2H), 2.17 (s, 3H), 1.61 (br. s., 2H); MS (EI/CI) m/z: 331.0 [M+H].

Example 28

6-(2-Aminoethylamino)-4-(2-tert-butylpyrimidin-4-ylamino)pyridazine-3-carboxamide Step 1

Ethyl 4-(2-tert-butylpyrimidin-4-ylamino)-6-chloropyridazine-3-carboxylate

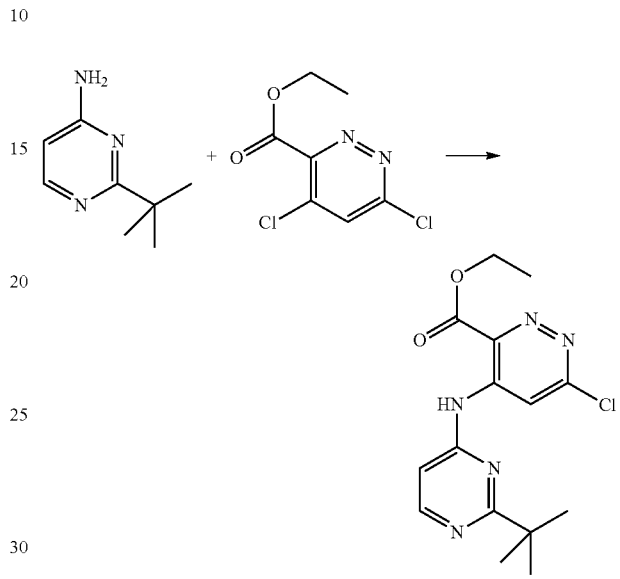

A microwave vessel was charged with 2-tert-butylpyrimidin-4-amine (1.00 g, 6.61 mmol, available commercially from J&W PharmLab, LLC) and ethyl 4,6-dichloropyridazine-3-carboxylate (0.545 g, 2.47 mmol) followed by acetonitrile (500 μL) and heated in a microwave at 150° C. for 3 h. After cooling to room temperature the mixture was evaporated and purified by chromatography (silica gel 45 μM, 80 g, Thomson, eluting with 0 to 10% acetone in CH₂Cl₂, 20 min) to give ethyl 4-(2-tert-butylpyrimidin-4-ylamino)-6-chloropyridazine-3-carboxylate (31 mg, 4%). ¹H NMR (CHLOROFORM-d) δ: 10.89 (br. s., 1H), 9.47 (s, 1H), 8.56 (d, J=5.3 Hz, 1H), 6.69 (d, J=5.7 Hz, 1H), 4.58 (q, J=7.2 Hz, 2H), 1.52 (t, J=7.2 Hz, 3H), 1.46 (s, 9H). MS (EI/CI) m/z: 336.0 [M+H].

Step 2

4-(2-tert-Butylpyrimidin-4-ylamino)-6-chloropyridazine-3-carboxamide

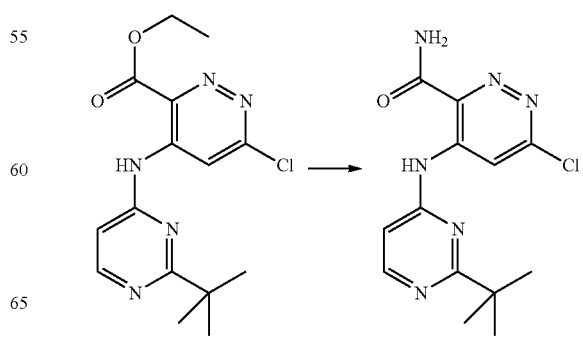

Ethyl 4-(2-tert-butylpyrimidin-4-ylamino)-6-chloropyridazine-3-carboxylate (31 mg, 92.3 μmol) was suspended in ammonia (7M in methanol, 2.36 g, 3.0 mL, 21.0 mmol), the flask sealed and stirred at r.t. for 5 h. The reaction mixture was then concentrated in vacuo to give 4-(2-tert-butylpyrimidin-4-ylamino)-6-chloropyridazine-3-carboxamide (28 mg, 99%) as an off-white solid. $^1$H NMR (DMSO-d$_6$) δ: 12.13 (s, 1H), 9.26 (s, 1H), 8.93 (br. s., 1H), 8.56 (d, J=5.7 Hz, 1H), 8.29 (br. s., 1H), 7.01 (d, J=5.7 Hz, 1H), 1.37 (s, 9H); MS (EI/CI) m/z: 307.0 [M+H].

Step 3

6-(2-Aminoethylamino)-4-(2-tert-butylpyrimidin-4-ylamino)pyridazine-3-carboxamide

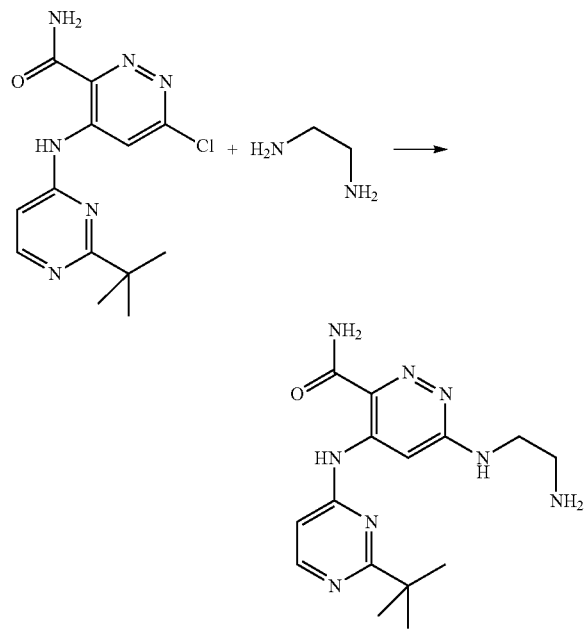

A flask was charged with 4-(2-tert-butylpyrimidin-4-ylamino)-6-chloropyridazine-3-carboxamide (28 mg, 91.3 μmol) and DMSO (1 mL). To this solution was added ethylenediamine (54.9 mg, 61.6 μL, 913 μmol) and the reaction mixture was heated in an oil bath with stirring at 120° C. for 1.5 h. The mixture was cooled and concentrated using a Kugelrohr distillation apparatus under high vacuum at 120° C. to afford a light brown solid. The solid was purified by chromatography (spherical silica 20-45 μM, 23 g, Versaflash Supelco, 0 to 10% of a 9:1 MeOH:NH$_4$OH solution in CH$_2$Cl$_2$, 20 min). The product obtained was dissolved in hot EtOH and concentrated to dryness, then recrystallized from ethanol and heptane. The off-white solid was separated by decanting the mother liquor then dried under high vacuum to give 6-(2-aminoethylamino)-4-(2-tert-butylpyrimidin-4-ylamino)pyridazine-3-carboxamide (22 mg, 73%) as a white solid. $^1$H NMR (CHLOROFORM-d) δ: 11.78 (br. s., 1H), 8.34-8.51 (m, 2H), 8.07 (br. s., 1H), 6.61 (d, J=5.7 Hz, 1H), 5.59 (br. s., 1H), 5.46 (br. s., 1H), 3.50 (m, 2H), 3.06 (m, 2H), 1.50-1.72 (m, 2H), 1.45 (s, 9H); MS (EI/CI) m/z: 331.0 [M+H].

Example 29

6-(2-Aminoethylamino)-4-(6-(2-methoxypropan-2-yl)pyridin-2-ylamino)pyridazine-3-carboxamide Step 1

2-Bromo-6-(2-methoxypropan-2-yl)pyridine

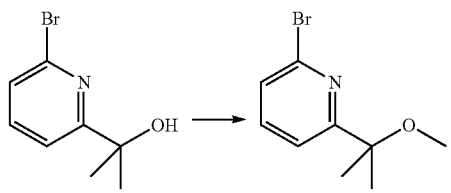

A dry flask fitted with a stir bar and septum was charged with 2-(6-bromopyridin-2-yl)propan-2-ol (1.66 g, 7.68 mmol), MeI (3.27 g, 1.44 mL, 23.0 mmol) and THF (40 mL). NaH (60% in mineral oil, 922 mg, 23.0 mmol) was added portion wise over 10 min and the reaction then stirred at room temperature overnight. Saturated aqueous ammonium chloride (20 mL) was added and the mixture extracted with dichloromethane (3×75 mL). The combined organic extracts were dried over magnesium sulfate, concentrated in vacuo, and purified by a chromatography (silica gel 50 μm, 80 g, Analogix, eluting with dichloromethane) to give 2-bromo-6-(2-methoxypropan-2-yl)pyridine (1.473 g, 81%) as a clear liquid $^1$H NMR (CHLOROFORM-d) δ: 7.49-7.57 (m, 2H), 7.34 (dd, J=6.6, 2.1 Hz, 1H), 3.19 (s, 3H), 1.54 (s, 6H); MS (EI/CI) m/z: 230.0, 232.0 [M+H].

Step 2

6-(2-Methoxypropan-2-yl)pyridin-2-amine

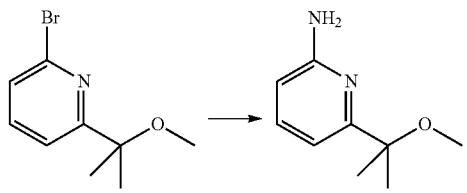

A heavy walled sealable tube was loaded under an argon atmosphere with copper (I) oxide (44.4 mg, 310 μmol), 2-bromo-6-(2-methoxypropan-2-yl)pyridine (1.427 g, 6.2 mmol), ammonium hydroxide (28% solution, 7.52 mL, 124 mmol), K$_2$CO$_3$ (171 mg, 1.24 mmol), N,N-dimethylethylenediamine (54.7 mg, 68.1 μL, 620 μmol) and ethyleneglycol (12.4 mL). The reaction was stirred for 6 h at 60° C. The reaction mixture was extracted with dichloromethane (3×25 mL), then the combined organic extracts were dried over magnesium sulfate, concentrated in vacuo and purified by chromatography (silica gel 50 μm, 40 g, Analogix, 0 to 5% of a 1:9 ammonium hydroxide:methanol solution in dichloromethane, 20 min) to obtain 6-(2-methoxypropan-2-yl)pyridin-2-amine (749 mg, 73%) as a white solid. $^1$H NMR (CHLOROFORM-d) δ: 7.42 (t, J=7.7 Hz, 1H), 6.85 (d, J=7.6 Hz, 1H), 6.37 (d, J=7.9 Hz, 1H), 4.41 (br. s., 2H), 3.15 (s, 3H), 1.51 (s, 6H); MS (EI/CI) m/z: 167.1 [M+H].

Step 3

Ethyl 6-chloro-4-(6-(2-methoxypropan-2-yl)pyridin-2-ylamino)pyridazine-3-carboxylate

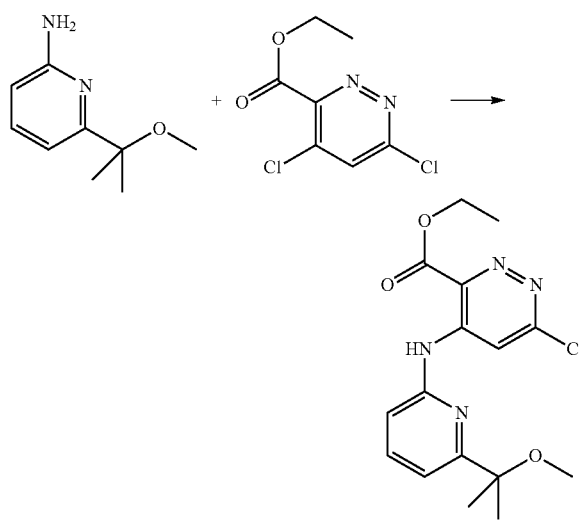

A mixture of ethyl 4,6-dichloropyridazine-3-carboxylate (665 mg, 3.01 mmol) and 6-(2-methoxypropan-2-yl)pyridin-2-amine (500 mg, 3.01 mmol) was dissolved in acetonitrile (3.3 mL) and heated at 95° C. for 72 h. The mixture was cooled, concentrated, and purified by chromatography (silica gel 45 μM, 80 g, Thomson, 0 to 10% acetone in dichloromethane, 20 min) to give ethyl 6-chloro-4-(6-(2-methoxypropan-2-yl)pyridin-2-ylamino)pyridazine-3-carboxylate (489 mg, 46%) as an off-white solid. $^1$H NMR (CHLOROFORM-d) δ: 10.72 (s, 1H), 9.27 (s, 1H), 7.71 (t, J=7.9 Hz, 1H), 7.24-7.31 (m, 1H), 6.81 (d, J=7.9 Hz, 1H), 4.56 (q, J=6.9 Hz, 2H), 3.21 (s, 3H), 1.60 (s, 6H), 1.50 (t, J=7.2 Hz, 3H); MS (EI/CI) m/z: 351.0, 353.0 [M+H].

Step 4

6-Chloro-4-(6-(2-methoxypropan-2-yl)pyridin-2-ylamino)pyridazine-3-carboxamide

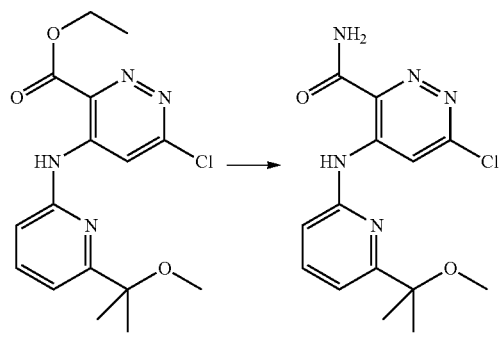 [SMILES: CCOC(=O)c1nnc(Cl)cc1Nc1cccc(C(C)(C)OC)n1 ; COC(C)(C)c1cccc(Nc2cc(Cl)nnc2C(N)=O)n1]

Ethyl 6-chloro-4-(6-(2-methoxypropan-2-yl)pyridin-2-ylamino)pyridazine-3-carboxylate (489 mg, 1.39 mmol) was suspended in ammonia (7M in methanol, 7.87 g, 10.0 mL, 70.0 mmol), the flask sealed and stirred at r.t. for 2 h. The mixture was concentrated in vacuo then dried under high vacuum to give 6-chloro-4-(6-(2-methoxypropan-2-yl)pyridin-2-ylamino)pyridazine-3-carboxamide (436 mg, 97%) as an off-white solid. $^1$H NMR (DMSO-d$_6$) δ: 11.98 (s, 1H), 9.14 (s, 1H), 8.85 (br. s., 1H), 8.20 (br. s., 1H), 7.81 (t, J=7.7 Hz, 1H), 7.21 (d, J=7.6 Hz, 1H), 7.00 (d, J=8.3 Hz, 1H), 3.08 (s, 3H), 1.50 (s, 6H); MS (EI/CI) m/z: 322.0, 324.0 [M+H].

Step 5

6-(2-Aminoethylamino)-4-(6-(2-methoxypropan-2-yl)pyridin-2-ylamino)pyridazine-3-carboxamide

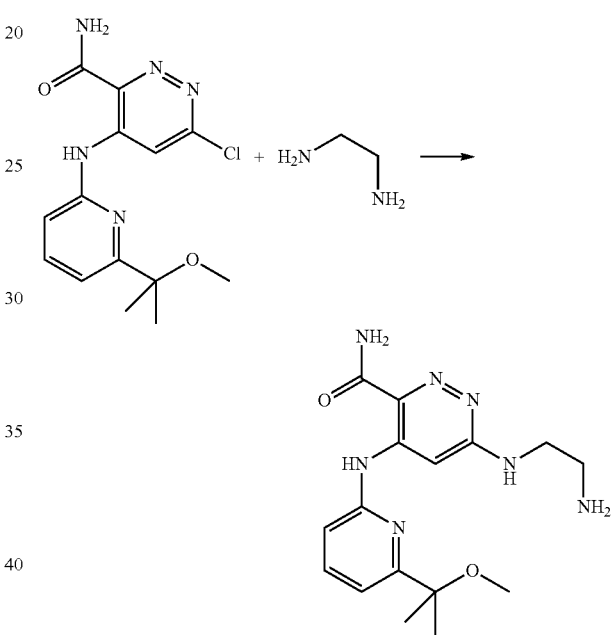

6-Chloro-4-(6-(2-methoxypropan-2-yl)pyridin-2-ylamino)pyridazine-3-carboxamide (186 mg, 578 μmol) dissolved in DMSO (2 mL). To this solution was added ethylenediamine (347 mg, 390 μL, 5.78 mmol) and the reaction mixture was heated at 120° C. for 1.5 h. The mixture was cooled and concentrated using a Kugelrohr distillation under high vacuum at 120° C. to afford a light brown solid. The crude solid was purified by chromatography (spherical silica 20-45 μM, 23 g, Versaflash Supelco, 0 to 10% of a 9:1 MeOH:NH$_4$OH solution in CH$_2$Cl$_2$, 20 min). The product was dissolved in hot EtOH and concentrated to dryness. The solid was recrystallized from ethanol, separated by decanting the mother liquor, and then dried to give 6-(2-aminoethylamino)-4-(6-(2-methoxypropan-2-yl)pyridin-2-ylamino)pyridazine-3-carboxamide (135 mg, 68%) as an off-white solid. $^1$H NMR (DMSO-d$_6$) δ: 11.78 (s, 1H), 8.37 (br. s., 1H), 7.93 (s, 1H), 7.71 (t, J=7.9 Hz, 1H), 7.64 (br. s., 1H), 7.21 (t, J=5.5 Hz, 1H), 7.08 (d, J=7.6 Hz, 1H), 6.81 (d, J=7.9 Hz, 1H), 3.23-3.29 (m, 2H), 3.08 (s, 3H), 2.75 (t, J=6.4 Hz, 2H), 1.53-1.68 (br. s., 2H), 1.50 (s, 6H); MS (EI/CI) m/z: 346.1 [M+H].

Example 30

4-((1R,2S)-2-Amino-cyclohexylamino)-2-(6-methyl-pyridin-2-ylamino)-benzamide Step 1

4-Fluoro-2-(6-methyl-pyridin-2-ylamino)-benzonitrile

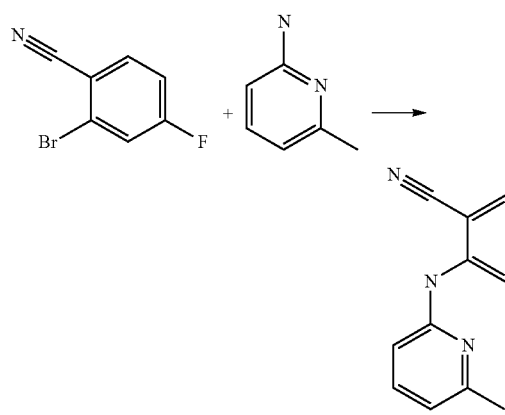

2-Bromo-4-fluoro-benzonitrile (1.0 g, 5.0 mmol), 6-methyl-pyridin-2-ylamine (540 mg, 5.0 mmol) and $Cs_2CO_3$ (4.88 g, 15.0 mmol) were dissolved in dioxane (30 mL), then the reaction mixture was de-gassed with nitrogen (purged through the solution for 5 min). $Pd_2dba_3$ (229 mg, 0.25 mmol) and Xantphos (289 mg, 0.5 mmol) were added under nitrogen and the mixture heated to 90° C. for 4 h. The reaction mixture was cooled, filtered and the filter cake washed with EtOAc (20 mL). The combined filtrates were concentrated under reduced pressure to give a crude residue that was purified by chromatography (silica, 10% to hexane to 15% EtOAc in hexanes) to give 4-fuoro-2-(6-methyl-pyridin-2-ylamino)-benzonitrile (470 mg, 41%) as white solid. MS (EI/CI) m/z: 228.2 [M+H].

Step 2

{(1S,2R)-2-[4-Cyano-3-(6-methyl-pyridin-2-ylamino)-phenylamino]-cyclohexyl}-carbamic acid tert-butyl ester

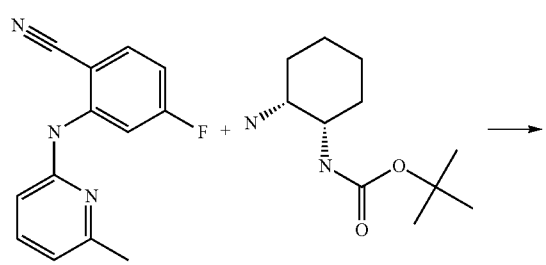

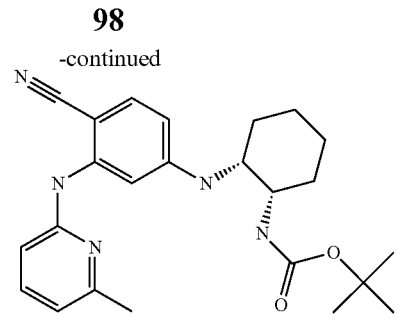

4-Fluoro-2-(6-methyl-pyridin-2-ylamino)-benzonitrile (400 mg, 1.76 mmol) and ((1S,2R)-2-amino-cyclohexyl)-carbamic acid tert-butyl ester (566 mg, 2.64 mmol) and methoxytrimethylsilane (916 mg, 8.8 mmol) were dissolved in NMP (5 mL), then heated at 140° C. in a sealed tube for 72 h. The reaction mixture was concentrated by high vacuum distillation. The residue obtained was purified by preparative HPLC (acetonitrile spiked with 5 mM $NH_4OAc$) to give {(1S,2R)-2-[4-cyano-3-(6-methyl-pyridin-2-ylamino)-phenylamino]-cyclohexyl}-carbamic acid tert-butyl ester (65 mg, 9%) as yellow solid. MS (EI/CI) m/z: 422.0 [M+H].

Step 3

{(1S,2R)-2-[4-Carbamoyl-3-(6-methyl-pyridin-2-ylamino)-phenylamino]-cyclohexyl}-carbamic acid tert-butyl ester

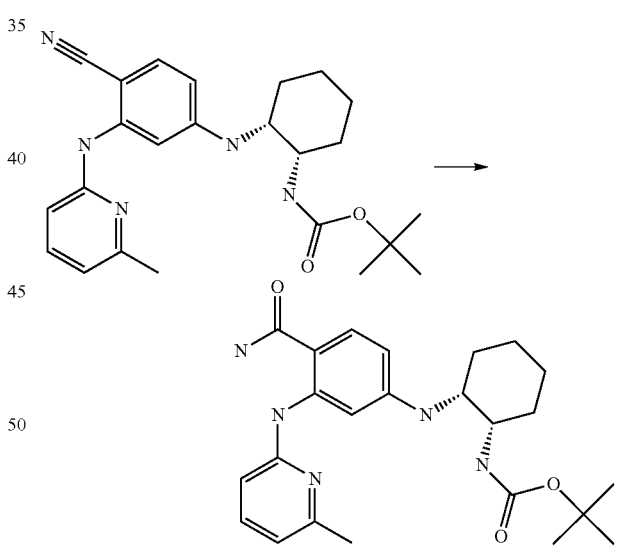

{(1S,2R)-2-[4-Cyano-3-(6-methyl-pyridin-2-ylamino)-phenylamino]-cyclohexyl}-carbamic acid tert-butyl ester (40 mg, 0.1 mmol) was dissolved in DMSO (1.5 mL) then $K_2CO_3$ (1.3 mg, 0.01 mmol) was added. The mixture was cooled to 0° C. and then $H_2O_2$ (30%, 1.5 mL) was added slowly. After 1 h, the reaction mixture was diluted with water (10 mL) and extracted with EtOAc (3×10 mL). The combined extracts were washed with water (3×15 mL), dried, filtered, and concentrated. The crude residue was purified by preparative TLC (40% EtOAc in hexane) to give {(1S,2R)-2-[4-carbamoyl-3-(6-methyl-pyridin-2-ylamino)- phenylamino]-cyclohexyl}-carbamic acid tert-butyl ester (27 mg, 65%) as a brown solid. MS (EI/CI) m/z: 440.3 [M+H].

Step 4

4-((1R,2S)-2-Amino-cyclohexylamino)-2-(6-methyl-pyridin-2-ylamino)-benzamide

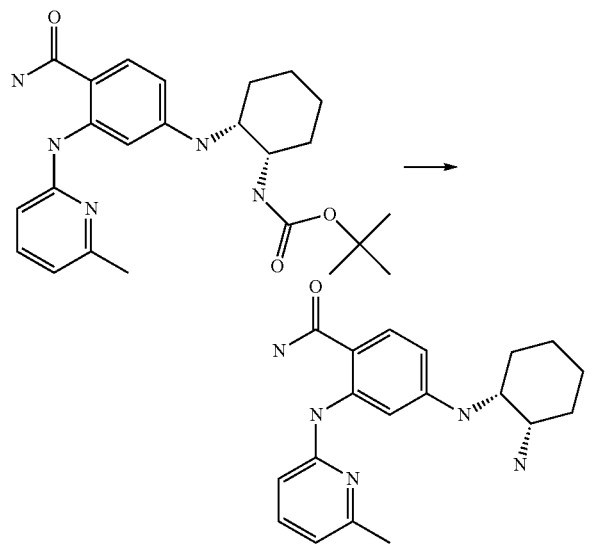

{(1S,2R)-2-[4-Carbamoyl-3-(6-methyl-pyridin-2-ylamino)-phenylamino]-cyclohexyl}-carbamic acid tert-butyl ester (25 mg, 0.057 mmol) was dissolved in DCM (1 mL) and cooled to 0° C. TFA (0.5 mL, 6.8 mmol) was added and the mixture stirred at room temperature for 1 h. The mixture was concentrated in vacuo then the residue obtained was triturated with Et₂O to get 4-((1R,2S)-2-amino-cyclohexylamino)-2-(6-methyl-pyridin-2-ylamino)-benzamide as the trifluoroacetate salt (24 mg, 93%) as a brown solid. MS (EI/CI) m/z: 340.4 [M+H].

Example 31

6-(2-aminoethylamino)-4-(5-isopropyl-6-methoxy-pyridin-2-ylamino)pyridazine-3-carboxamide Step 1

6-Methoxy-5-(prop-1-en-2-yl)pyridin-2-amine

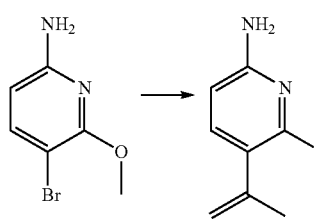

To a solution 5-bromo-6-methoxypyridin-2-amine (1.72 g, 8.47 mmol) in dimethylacetamide (26 mL) was added 4,4,5,5-tetramethyl-2-(prop-1-en-2-yl)-1,3,2-dioxaborolane (2.07 mL, 11.0 mmol), palladium tetrakis(triphenylphosphine) (979 mg, 847 μmol) and tribasic potassium phosphate (3.6 g, 16.9 mmol) in water (7.63 mL, 424 mmol). The mixture was sealed in a microwave vial and heated at 150° C. in a microwave reactor for 15 min. Upon cooling, the mixture was diluted with EtOAc and Et₂O, washed with water and brine, concentrated, adsorbed onto silica gel, and purified by chromatography (10% to 40% EtOAc in hexanes) to give 6-methoxy-5-(prop-1-en-2-yl)pyridin-2-amine contaminated with catalyst-derived impurities (~950 mg, used into the next step without further purification). $^1$H NMR (400 MHz, CHLOROFORM-$d_6$) δ ppm 7.34 (d, J=8.0 Hz, 1H), 6.06 (d, J=8.1 Hz, 1H), 5.19 (m, 1H), 5.09 (m, 1H), 4.29 (br. s, 2H), 3.91 (s, 3H), 2.10 (s, 3H).

Step 2

5-Isopropyl-6-methoxypyridin-2-amine

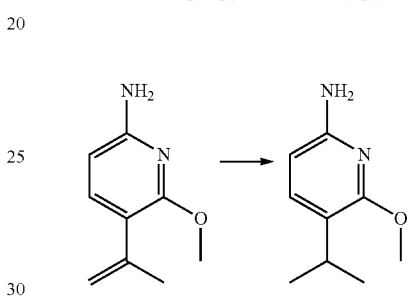

To a solution of 5-fluoro-6-isopropenyl-pyridin-2-ylamine (crude from Step 1, 8.47 mmol) in methanol (17.5 mL) was added 10% palladium on carbon (123 mg) at room temperature. A hydrogen balloon (1 atm) was attached and the mixture was stirred overnight. After 18 hours, the mixture was filtered over celite, concentrated, adsorbed onto silica gel, and purified by chromatography (10% to 40% ethyl acetate in hexanes) to give 5-isopropyl-6-methoxy-pyridin-2-amine (740 mg, 53% over two steps). $^1$H NMR (400 MHz, CHLOROFORM-$d_6$) δ ppm 7.26 (d, J=7.8 Hz, 1H), 6.07 (d, J=8.1 Hz, 1H), 4.19 (br. s, 2H), 3.90 (s, 3H), 3.08 (m, 1H), 1.17 (d, J=6.9 Hz, 6H).

Step 3

Ethyl 6-chloro-4-(5-isopropyl-6-methoxypyridin-2-ylamino)pyridazine-3-carboxylate

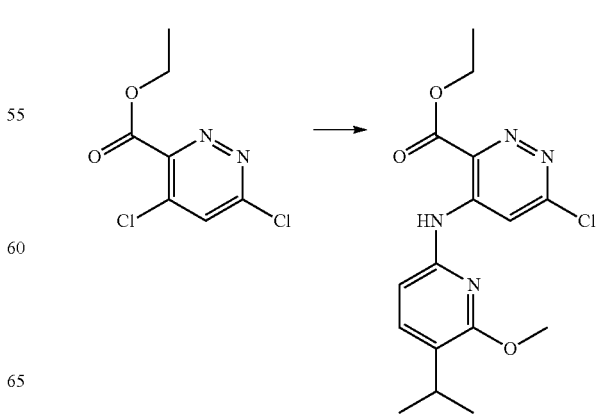

To a solution of ethyl 4,6-dichloropyridazine-3-carboxylate (1.47 g, 6.64 mmol) in acetonitrile (7.6 mL) was added 5-isopropyl-6-methoxypyridin-2-amine (830 mg, 4.99 mmol) and the mixture heated at 100° C. in a sealed tube for 18 h. Upon completion, the mixture was concentrated, adsorbed onto silica gel and purified by chromatography (silica, 10% to 80% ethyl acetate in hexanes) to give ethyl 6-chloro-4-(5-isopropyl-6-methoxypyridin-2-ylamino)pyridazine-3-carboxylate (500 mg, 28.5%). MS (EI/CI) m/z: 351.2 [M+H].

Step 4

6-Chloro-4-(5-isopropyl-6-methoxypyridin-2-ylamino)pyridazine-3-carboxamide

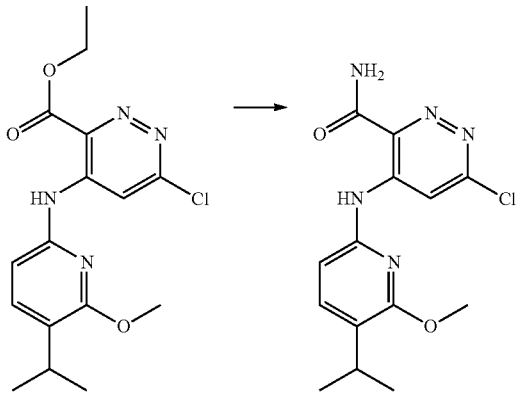 [SMILES: CCOC(=O)c1nnc(Cl)cc1Nc1ccc(C(C)C)c(OC)n1 ; COc1nc(Nc2cc(Cl)nnc2C(N)=O)ccc1C(C)C]

To a solution of ethyl 6-chloro-4-(5-isopropyl-6-methoxypyridin-2-ylamino)pyridazine-3-carboxylate (500 mg, 1.43 mmol) was added 7N ammonia in MeOH (20.5 mL, 143 mmol). The mixture was stirred at 40° C. for 18 h, after which the solvent was removed to give 6-chloro-4-(5-isopropyl-6-methoxy-pyridin-2-ylamino)-pyridazine-3-carboxylic acid amide (450 mg, 98%) as an off-white solid. $^1$H NMR (400 MHz, CHLOROFORM-$d_6$) δ ppm 11.47 (s, 1H), 9.10 (s, 1H), 8.17 (s, 1H), 7.48 (d, J=8.0 Hz, 1H), 6.53 (d, J=7.7 Hz, 1H), 5.71 (s, 1H), 4.04 (s, 3H), 3.18 (m, 1H), 1.23 (d, J=7.1 Hz, 6H).

Step 5

6-(2-aminoethylamino)-4-(5-isopropyl-6-methoxy-pyridin-2-ylamino)pyridazine-3-carboxamide

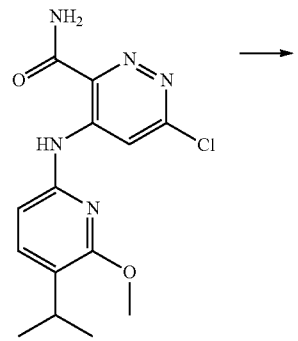

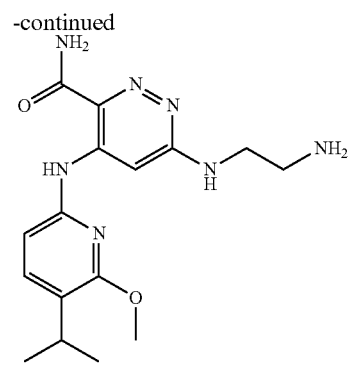

To a solution of 6-chloro-4-(5-isopropyl-6-methoxypyridin-2-ylamino)pyridazine-3-carboxamide (210 mg, 653 µmol) in NMP (2.18 mL) was added ethane-1,2-diamine (157 mg, 175 µl, 2.61 mmol) and the mixture heated at 100° C. for 24 h. The mixture was concentrated in vacuo then purified by HPLC (C-18, 10-100% water in acetonitrile gradient containing acetic acid modifier). The product obtained was neutralized with NH$_4$OH solution to give 6-(2-aminoethylamino)-4-(5-isopropyl-6-methoxypyridin-2-ylamino)pyridazine-3-carboxamide (8 mg, 23 µmol, 4%) as a white solid. $^1$H NMR (400 MHz, DMSO-$d_6$) δ ppm 11.59 (s, 1H), 8.34 (s, 1H), 7.79 (s, 1H), 7.66 (s, 1H), 7.53 (d, J=7.9 Hz, 1H), 7.19 (t, J=6.1 Hz, 1H), 6.51 (d, J=7.7 Hz, 1H), 3.97 (s, 3H), 3.43 (m, 2H), 3.07 (m, 1H), 2.87 (t, J=5.7 Hz, 2H), 1.16 (d, J=6.1 Hz, 6H); MS (EI/CI) m/z: 346.2 [M+H].

Example 32

6-(2-aminoethylamino)-4-(5-fluoro-6-isopropylpyridin-2-ylamino)pyridazine-3-carboxamide Step 1

(6-Bromo-5-fluoro-pyridin-2-yl)-carbamic acid tert-butyl ester

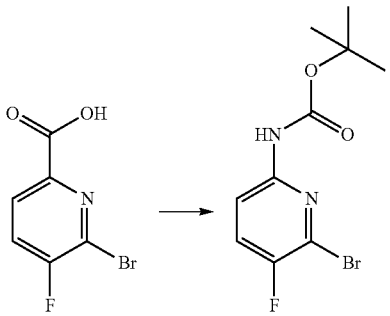 [SMILES: O=C(O)c1ccc(F)c(Br)n1 ; CC(C)(C)OC(=O)Nc1ccc(F)c(Br)n1]

To a solution of 6-bromo-5-fluoro-2-picolinic acid (2 g, 9.09 mmol) in tert-butanol (46 mL) and triethylamine (1.27 mL, 9.09 mmol, Eq: 1.00) was added DPPA (1.97 mL, 9.09 mmol). The slurry was stirred at room temperature until all solids dissolved (~15 min), after which it was heated to 85° C. for 2 h. Upon cooling, the mixture was concentrated, adsorbed onto silica gel and purified by chromatography (silica, 5% to 30% EtOAc in hexanes) to give (6-bromo-5-fluoro-pyridin-2-yl)-carbamic acid tert-butyl ester (1.55 g, 59%). $^1$H NMR (400 MHz, CHLOROFORM-$d_6$) δ ppm 7.97 (d, J=8.6 Hz, 1H), 7.43 (d, J=8.6 Hz, 1H), 1.53 (s, 9H).

Step 2

6-Bromo-5-fluoro-pyridin-2-ylamine

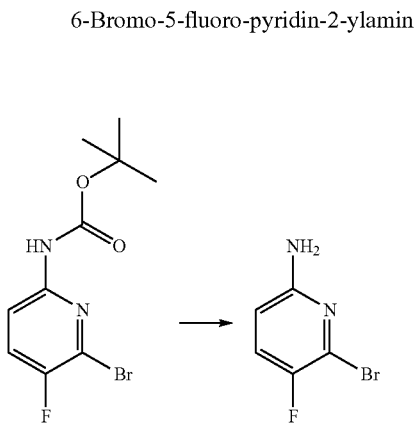

To a solution of (6-bromo-5-fluoro-pyridin-2-yl)-carbamic acid tert-butyl ester (1.43 g, 4.91 mmol,) in DCM (25 mL) was added TFA (3.78 mL, 49.1 mmol, Eq: 10.0). The mixture was stirred at room temperature for 2 h, after which it was concentrated in vacuo, and redissolved in EtOAc. The organic layer was washed with sat. aq. NaHCO$_3$ followed by water and brine. The resulting organic layer was concentrated, adsorbed onto silica gel and purified by chromatography (10% to 40% EtOAc/hexanes) to give 6-bromo-5-fluoro-pyridin-2-ylamine (850 mg, 91%). $^1$H NMR (400 MHz, CHLOROFORM-$d_6$) δ ppm 7.23 (dd, J=8.6, 7.5 Hz, 1H), 6.41 (dd, J=8.6, 2.6 Hz, 1H), 4.40 (br. s, 2H).

Step 3

5-Fluoro-6-isopropenyl-pyridin-2-ylamine

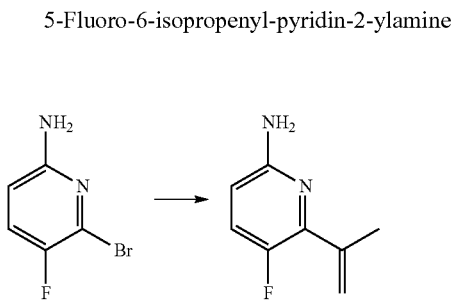

To a solution 6-bromo-5-fluoro-pyridin-2-ylamine (850 mg, 4.45 mmol) in dimethylacetamide (13.5 mL) was added 4,4,5,5-tetramethyl-2-(prop-1-en-2-yl)-1,3,2-dioxaborolane (1.09 mL, 5.79 mmol), palladium tetrakis(triphenylphosphine) (514 mg, 445 μmol) and tribasic potassium phosphate (1.89 g, 8.9 mmol) in water (4 mL). The mixture was sealed in a microwave vial and heated at 150° C. in a microwave reactor for 15 min. Upon cooling, the mixture was diluted with EtOAc, washed with water and brine, concentrated, adsorbed onto silica gel, and purified by chromatography (20% to 100% EtOAc in hexanes) to give 5-fluoro-6-isopropenyl-pyridin-2-ylamine contaminated with catalyst-derived impurities (~800 mg) that was used directly in the next step without further purification.

Step 4

5-Fluoro-6-isopropylpyridin-2-amine

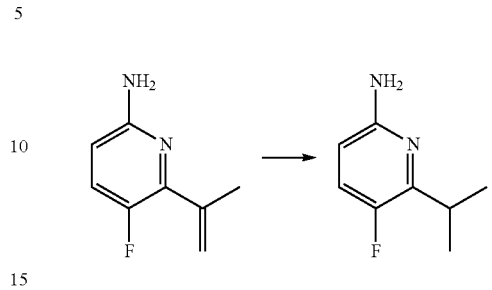

To a solution of 5-fluoro-6-isopropenyl-pyridin-2-ylamine (crude from last step, 4.45 mmol) in methanol (13.5 mL) was added 10% palladium on carbon (95 mg) at room temperature. A hydrogen balloon (1 atm) was attached and the mixture was stirred overnight. After 18 h, the mixture was filtered over celite, concentrated, adsorbed onto silica gel, and purified by chromatography (10% to 40% EtOAc in hexanes) to give 5-fluoro-6-isopropylpyridin-2-amine (470 mg, 69% over two steps). $^1$H NMR (400 MHz, CHLOROFORM-$d_6$) δ ppm 7.12 (t, J=9.2 Hz, 1H), 6.30 (dd, J=8.5, 3.0 Hz, 1H), 4.31 (br. s, 2H), 4.15 (m, 1H), 1.26 (d, J=7.2 Hz, 6H).

Step 5

Ethyl 6-chloro-4-(5-fluoro-6-isopropylpyridin-2-ylamino)pyridazine-3-carboxylate

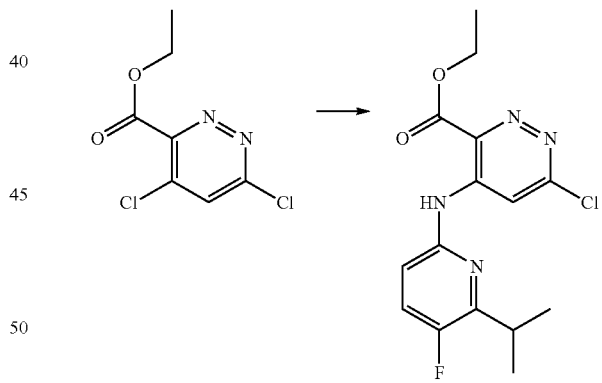

To a solution of ethyl 4,6-dichloropyridazine-3-carboxylate (674 mg, 3.05 mmol) in acetonitrile (10 mL) was added 5-fluoro-6-isopropylpyridin-2-amine (470 mg, 3.05 mmol) and heated at 130° C. in a sealed tube for 18 h. Upon completion, the mixture was concentrated, adsorbed onto silica gel and purified by chromatography (silica. 10% to 33% EtOAc in hexanes) to give ethyl 6-chloro-4-(5-fluoro-6-isopropylpyridin-2-ylamino)pyridazine-3-carboxylate (150 mg, 22%). $^1$H NMR (400 MHz, CHLOROFORM-$d_6$) δ ppm 10.72 (s, 1H), 9.23 (s, 1H), 7.38 (t, J=8.4 Hz, 1H), 6.79 (dd, J=8.5, 2.8 Hz, 1H), 4.57 (m, 2H), 3.45 (m, 1H), 1.53 (m, 3H), 1.36 (d, J=6.9 Hz, 6H).

Step 6

6-Chloro-4-(5-fluoro-6-isopropylpyridin-2-ylamino)pyridazine-3-carboxamide

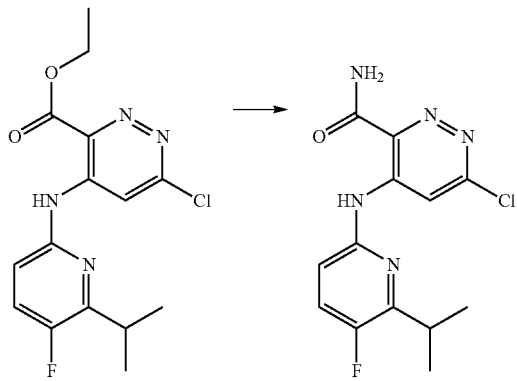 [SMILES: CCOC(=O)c1nnc(Cl)cc1Nc1ccc(F)c(C(C)C)n1 ; CC(C)c1nc(Nc2cc(Cl)nnc2C(N)=O)ccc1F]

To a solution of ethyl 6-chloro-4-(5-fluoro-6-isopropylpyridin-2-ylamino)pyridazine-3-carboxylate (290 mg, 856 µmol) was added 7N ammonia in MeOH (12.2 mL, 85.6 mmol). The mixture was stirred at 40° C. for 18 h, after which the solvent was removed to give 6-chloro-4-(5-fluoro-6-isopropylpyridin-2-ylamino)pyridazine-3-carboxamide (250 mg, 94%) as an off-white solid. $^1$H NMR (400 MHz, CHLOROFORM-$d_6$) δ ppm 11.86 (s, 1H), 9.26 (s, 1H), 8.19 (br. s, 1H), 7.36 (t, J=8.8 Hz, 1H), 6.79 (dd, J=8.5, 2.8 Hz, 1H), 5.70 (br. s, 1H), 3.45 (m, 1H), 1.37 (d, J=6.7 Hz, 6H).

Step 7

6-(2-Aminoethylamino)-4-(5-fluoro-6-isopropylpyridin-2-ylamino)pyridazine-3-carboxamide

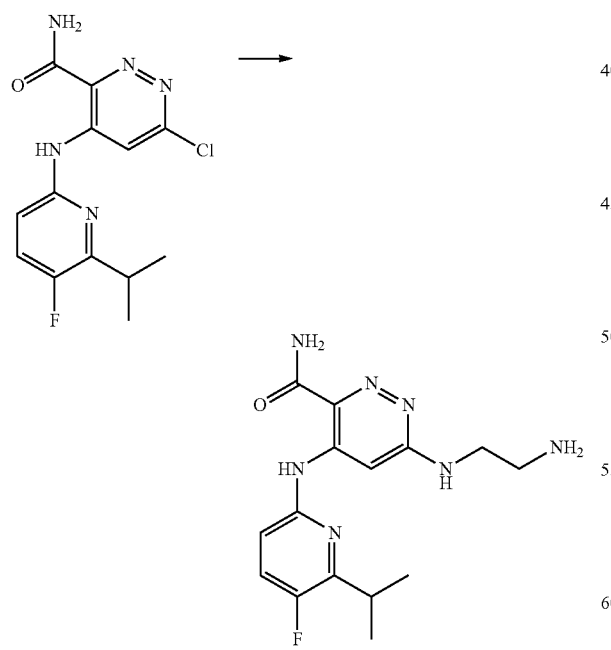

To a solution of 6-chloro-4-(5-fluoro-6-isopropylpyridin-2-ylamino)pyridazine-3-carboxamide (145 mg, 468 µmol) in NMP (1.6 mL) was added ethane-1,2-diamine (113 mg, 125 µL, 1.87 mmol) and the mixture heated to 100° C. for 24 h. The mixture was cooled and concentrated in vacuo then purified by HPLC (C-18, 10-100% water in acetonitrile gradient containing acetic acid modifier). The product obtained was neutralized with $NH_4OH$ and dried in vacuo to give 6-(2-aminoethylamino)-4-(5-fluoro-6-isopropylpyridin-2-ylamino)pyridazine-3-carboxamide (21 mg, 63 µmol, 14%) as a white solid. $^1$H NMR (400 MHz, DMSO-$d_6$) δ ppm 11.76 (s, 1H), 8.38 (s, 1H), 7.88 (s, 1H), 7.64 (s, 1H), 7.59 (t, J=8.9 Hz, 1H), 7.21 (t, J=5.5 Hz, 1H), 6.85 (dd, J=9.0, 2.8 Hz, 1H), 3.35 (m, 2H), 2.82 (t, J=6.2 Hz, 2H), 1.29 (d, J=6.8 Hz, 6H); MS (EI/CI) m/z: 334.3 [M+H].

Example 33

6-(2-aminoethylamino)-4-(6-isopropoxypyridin-2-ylamino)pyridazine-3-carboxamide

Step 1

Ethyl 6-chloro-4-(6-isopropoxypyridin-2-ylamino)pyridazine-3-carboxylate

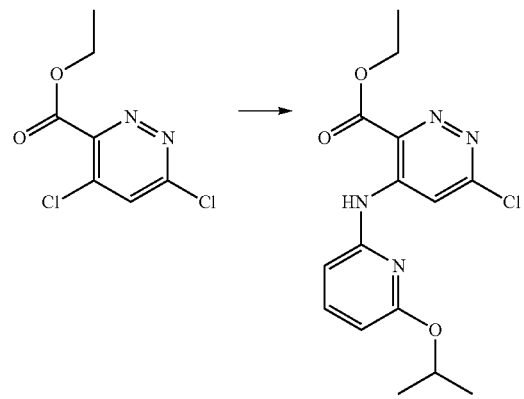 [SMILES: CCOC(=O)c1nnc(Cl)cc1Cl ; CCOC(=O)c1nnc(Cl)cc1Nc1cccc(OC(C)C)n1]

To a solution of ethyl 4,6-dichloropyridazine-3-carboxylate (1.63 g, 7.36 mmol) in acetonitrile (25 mL) was added 6-isopropoxypyridin-2-amine (1.12 g, 7.36 mmol) and the mixture heated at 130° C. in a sealed tube for 60 h. Upon completion, the mixture was concentrated, adsorbed onto silica gel and purified by chromatography (20% to 66% EtOAc in hexanes) to give ethyl 6-chloro-4-(6-isopropoxypyridin-2-ylamino)pyridazine-3-carboxylate (330 mg, 13%). MS (EI/CI) m/z: 337.1 [M+H].

Step 2

6-Chloro-4-(6-isopropoxypyridin-2-ylamino)pyridazine-3-carboxamide

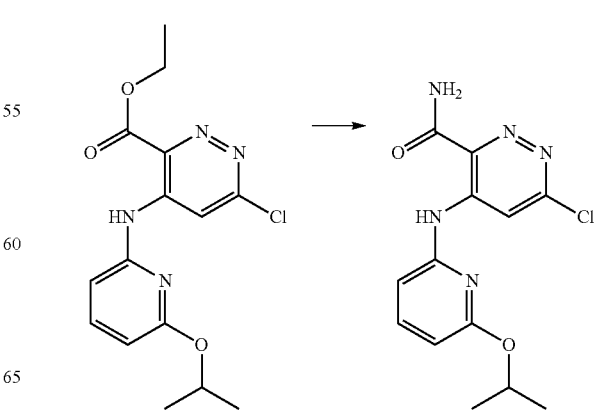

To a solution of give ethyl 6-chloro-4-(6-isopropoxypyridin-2-ylamino)pyridazine-3-carboxylate (530 mg, 1.57 mmol) was added 7N ammonia in MeOH (16.9 mL, 118 mmol). The mixture was stirred at 40° C. for 18 h, after which the solvent was removed to give 6-chloro-4-(6-isopropoxypyridin-2-ylamino)pyridazine-3-carboxamide (470 mg, 97%) as an off-white solid. $^1$H NMR (400 MHz, CHLOROFORM-d$_6$) δ ppm 11.57 (s, 1H), 9.08 (s, 1H), 8.17 (s, 1H), 7.58 (t, J=7.8 Hz, 1H), 6.50 (d, J=7.3 Hz, 1H), 6.44 (d, J=8.0 Hz, 1H), 5.69 (s, 1H), 5.23 (m, 1H), 1.47 (d, J=6.3 Hz, 6H).

Step 3

6-(2-Aminoethylamino)-4-(6-isopropoxypyridin-2-ylamino)pyridazine-3-carboxamide

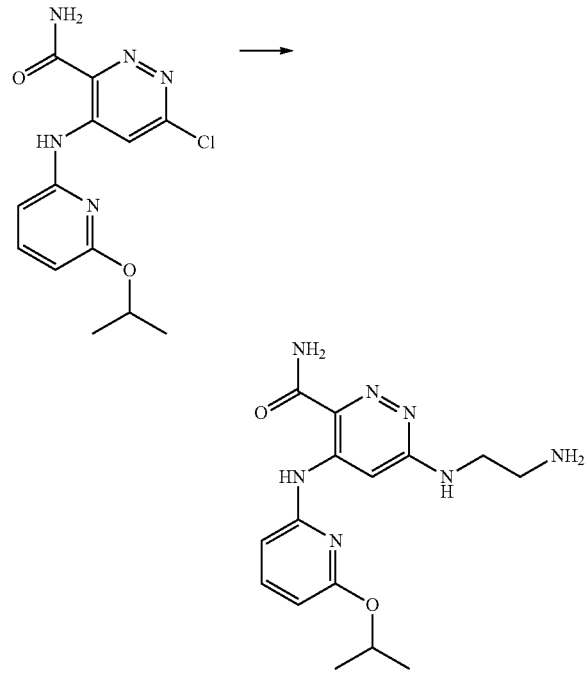

To a solution of 6-chloro-4-(6-isopropoxypyridin-2-ylamino)pyridazine-3-carboxamide (200 mg, 650 µmol) in NMP (2.2 mL) was added ethane-1,2-diamine (156 mg, 174 µL, 2.6 mmol) and the mixture heated at 100° C. for 16 h. The mixture was concentrated in vacuo then purified by HPLC (C-18, 10-100% water in acetonitrile gradient containing acetic acid modifier). The product obtained was neutralized with NH$_4$OH then dried in vacuo to give 6-(2-aminoethylamino)-4-(6-isopropoxypyridin-2-ylamino)pyridazine-3-carboxamide (43 mg, 130 µmol, 20%) as a white solid. $^1$H NMR (400 MHz, DMSO-d$_6$) δ ppm 11.72 (s, 1H), 8.37 (s, 1H), 7.67 (s, 1H), 7.65 (s, 1H), 7.60 (t, J=8.0 Hz, 1H), 7.15 (t, J=5.6 Hz, 1H), 6.48 (d, J=7.6 Hz, 1H), 6.33 (d, J=7.8 Hz, 1H), 5.22 (m, 1H), 3.33 (m, 2H), 2.80 (t, J=6.2 Hz, 2H), 1.33 (d, J=6.2 Hz, 6H); MS (EI/CI) m/z: 332.3 [M+H].

Example 34

6-(2-Aminoethylamino)-4-(5,6-dimethylpyridin-2-ylamino)pyridazine-3-carboxamide

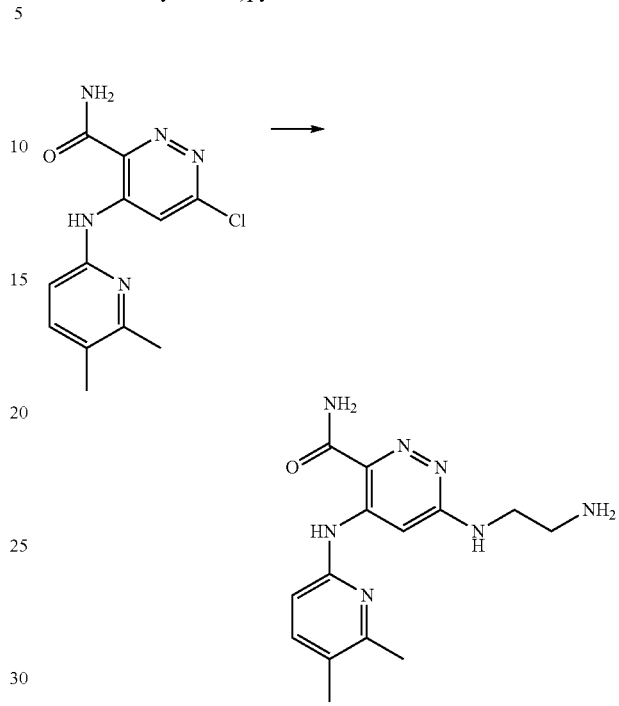

A pressure tube was charged with 6-chloro-4-(5,6-dimethylpyridin-2-ylamino)pyridazine-3-carboxamide (150 mg, 540 µmol, prepared as in example 13) and NMP (2 mL). To this solution was added ethylenediamine (325 mg, 365 µL, 5.4 mmol) and the reaction mixture was stirred at 140° C. for 1.5 h. After cooling to room temperature, the NMP and the ethylenediamine were distilled off using a Kugelrohr apparatus under high vacuum and at 120° C. to afford a light brown solid. This was then purified by chromatography (spherical silica 20-45 mm, 11 g, Versaflash from Supelco, 0.3:5.7:94 NH$_4$OH:MeOH:dichloromethane to 0.6:11.4:88 NH$_4$OH:MeOH:dichloromethane over 40 min) to give 6-(2-aminoethylamino)-4-(5,6-dimethylpyridin-2-ylamino)pyridazine-3-carboxamide as a yellow solid (114 mg, 70.1%). $^1$H NMR (400 MHz, DMSO-d$_6$) d ppm 11.49 (br. s., 1H) 8.35 (br. s., 1H) 8.00-8.16 (m, 1H) 7.61 (br. s., 1H) 7.46 (d, J=7.83 Hz, 1H) 7.20 (br. s., 1H) 6.71 (d, J=8.08 Hz, 1H) 3.36 (d, J=4.29 Hz, 2H) 2.78 (t, J=5.81 Hz, 2H) 2.45 (s, 3H) 2.19 (s, 3H). MS (EI/CI) m/z: 302 [M+H].

BIOLOGICAL EXAMPLES

SYK Assay Information

Determination of IC$_{50}$ of Spleen Tyrosine Kinase (SYK) Inhibition:

SYK kinase assay is a standard kinase assay adapted to a 96 well plate format. This assay is performed in 96-well format for IC$_{50}$ determination with 8 samples which represented 10 half log dilutions and a 40 µL reaction volume. The assay measures the incorporation of radiolabeled $^{33}$P γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10) Streptavidin coated beads: Streptavidin Sepharose™, suspension 5.0 mL, in 50 mM EDTA/PBS diluted (1:100), (Amersham, Cat. No.: 17-5113-01)

Compounds: 10 mM in 100% dimethylsulfoxide (DMSO), final conc.: compound 0.003-100 uM in 10% DMSO Enzyme: SYK RPA purified, truncated construct of Spleen Tyrosine Kinase aa 360-635, stock solution 1 mg/mL, MW: 31.2 KDa, final conc.:0.0005 μM.

Peptide 1: biotinylated peptide is derived from a naturally occurring phosphor-acceptor consensus sequence (Biotin-EPEGDYEEVLE), special order from QCB, stock solution 20 mM, final conc.: 5.0 μM.

ATP: Adenosine-5'-triphosphate 20 mM, (ROCHE Cat. No.: 93202720), final concentration: 20 μM Buffer: HEPES: 2-Hydroxyethyl piperazine-2-ethanesulfonic acid (Sigma, Cat. No.: H-3375)
final concentration: 50 mM HEPES pH7.5

BSA: Bovine Serum Albumin Fraction V, fatty acid free (Roche Diagnostics GmbH, Cat. No. 9100221) diluted to a final concentration of 0.1%

EDTA: EDTA stock solution 500 mM, (GIBCO, Cat. No.: 15575-038) final concentration: 0.1 mM DTT: 1,4-Dithiothreitol (Roche Diagnostics GmbH, Cat. No.: 197777), final conc.: 1 mM $MgCl_2 \times 6H_2O$: MERCK, Cat. No.: 105833.1000, final concentration: 10 mM Assay Dilution Buffer (ADB): 50 mM HEPES, 0.1 mM EGTA, 0.1 mM Na Vanadate, 0.1 mM β-glycerophosphate, 10 mM $MgCl_2$, 1 mM DTT, 0.1% BSA, pH 7.5

Bead wash buffer: 10 g/L PBS (Phosphate buffered saline) with 2M NaCl+1% phosphoric acid.

Experimental Method

In 40 μL volume, 26 μL of ADB diluted, purified recombinant human SYK360-635 [0.5 nM] was mixed with 4 μL of 10× concentrations of the test compounds, [usually 100 μM-0.003 μM] in [10%] DMSO and the mixture was incubated for 10 min at RT.

The kinase reaction was initiated by the addition of 10 μL 4× substrate cocktail containing the DYE peptide substrate [0 or 5 μM], ATP [20 μM] and $^{33}P\gamma ATP$ [2 μCi/rxn]. After incubation at 30° C. for 15 min, the reaction was terminated by the transfer of 254 μL pf the reaction sample to a 96 well 0.65 μm Millipore MADVNOB membrane/plate containing 200 μL 5 mM EDTA and 20% Streptavidine coated beads in PBS.

The unbound radionucleotides were washed under vacuum with 3×250 μL 2M NaCl; 2×250 μL 2M NaCl+1% phosphoric acid; 1×250 μL $H_2O$. After the last wash membrane/plates were transferred to an adaptor plate, heat dried for 15 min at 60° C., and 50 μL scintillation cocktail was added to each well and 4 h later the amount of radioactivity was counted in a top counter.

The percent inhibition was calculated based on the uninhibited enzyme rate:

% Inhibition=100/(1+($IC_{50}$/Inhibitor conc)$^n$)

The $IC_{50}$ was calculated using a non-linear curve fit with XLfit software (ID Business Solution Ltd., Guilford, Surrey, UK).

B Cell CD69 Up-Regulation Assay in Human Whole Blood

Human Blood was collected from healthy volunteers into Vacutainers (BD Biosciences, San Jose, Calif.) containing sodium heparin. Test compound was suspended in DMSO and nine half-log serial dilutions were made. The concentration of compound in the assay was 0.5%. 100 μL whole blood was pre-incubated with compound for 30 min and then stimulated with goat F(ab')$_2$ anti-human IgM (50 μg/mL, Southern Biotech) for 20 h. At the end of the 20 hour incubation, samples were incubated with fluorochrome-conjugated antibodies, PE mouse anti-human CD20 and APC Mouse anti-human CD69 (BD Biosciences), for 30 minutes. Samples were then lysed with Lyse solution (BD) and washed with PBS containing 2% fetal bovine serum (FBS). Fluorescent signals were acquired on flow cytometer LSR II (BD) and data were analyzed by Flow Jo. The percentage of activated (CD69hi) B-cell lymphocytes (CD20+) were determined using un-stimulated (negative control) and stimulated (positive control) wells as reference guidelines. The percentage inhibition was calculated and an $IC_{50}$ curve was constructed using GraphPad Prism software with sigmoidal curve fitting.

| Compound | Syk_IC50 (μM) | Human whole blood IC50 (μM) |
|---|---|---|
| I-1 | 1.32 | |
| I-2 | 0.965 | |
| I-3 | 2.24 | |
| I-4 | 0.671 | |
| I-5 | 1.50 | |
| I-6 | 0.385 | |
| I-7 | 0.473 | |
| I-8 | 0.373 | >5 |
| I-9 | 1.41 | |
| I-10 | 2.18 | |
| I-11 | 0.225 | >5 |
| I-12 | 0.006 | 0.992 |
| I-13 | | >50 |
| I-14 | 0.124 | >50 |
| I-15 | 0.002 | 0.931 |
| I-16 | 0.013 | 0.603 |
| I-17 | 0.006 | 0.508 |
| I-18 | | 0.141 |
| I-19 | 0.135 | 6.02 |
| I-20 | 0.011 | 0.157 |
| I-21 | 0.100 | 0.573 |
| I-22 | 2.54 | >5 |
| I-23 | 0.161 | 2.06 |
| I-24 | 3.98 | >5 |
| I-25 | 0.007 | 0.052 |
| I-26 | 0.038 | 0.119 |
| I-27 | 0.020 | 0.287 |
| I-28 | 0.17025 | 0.358 |
| I-29 | 0.75495 | 1.80 |
| I-30 | 0.0418 | 0.548 |
| I-31 | 0.00925 | 1.50 |
| I-32 | 0.0378 | 0.813 |
| I-33 | 0.01245 | 0.566 |
| I-34 | 0.0244 | 0.291 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound of Formula I

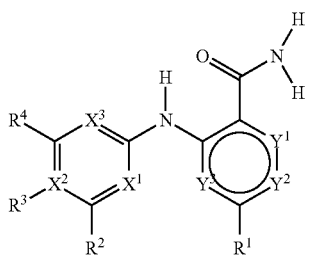

wherein:
R¹ is —OR¹' or (CH₂)ₙR¹';
R¹' is phenyl, pyridyl, cycloalkyl, amino cycloalkyl C₁₋₆ alkyl or C₁₋₆ alkyl, optionally substituted with one or more R¹'';
each R¹'' is independently cyano, amino, amino C₁₋₆ alkyl, halo, C₁₋₆ alkyl, cycloalkyl, or amino cycloalkyl C₁₋₆ alkyl;
R² is C₁₋₆ alkyl, cycloalkyl, cyano C₁₋₆ alkyl, hydroxy C₁₋₆ alkyl, halo C₁₋₆ alkyl, dialkyl amino, or C₁₋₆ alkoxy;
R³ is absent;
R⁴ is H or C₁₋₆ alkyl;
X¹ is CH or N;
X² is CH, CR² or N;
X³ is CH or N;
Y¹ is N; and
Y² is N;
Y³ is CH; and
n is 0 or 1;
or a pharmaceutically acceptable salt thereof.

2. The compound according to claim 1 wherein,

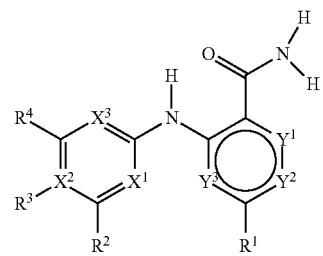

wherein:
R¹ is —OR¹'(CH₂)ₙR¹';
R¹' is phenyl, pyridyl, cycloalkyl, or C₁₋₆ alkyl, optionally substituted with one or more R¹'';
each R¹'' is independently cyano, amino, amino C₁₋₆ alkyl, halo, C₁₋₆ alkyl, cycloalkyl, or amino cycloalkyl C₁₋₆ alkyl;
R² is C₁₋₆ alkyl, cycloalkyl, cyano CI-alkyl, hydroxy C₁₋₆ alkyl, halo C₁₋₆ alkyl, dialkyl amino, or C₁₋₆ alkoxy;
R³ is absent;
R⁴ is H or C₁₋₆ alkyl;
X¹ is CH or N;
X² is CH, CR² or N;
X³ is CH or N;
Y¹ is N;
Y² is N; and
Y³ is CH;
or a pharmaceutically acceptable salt thereof.

3. The compound according to claim 1, wherein R¹' is C₁₋₆alkyl, optionally substituted with one or more R¹''.
4. The compound according to claim 1, wherein X¹ is N.
5. The compound according to claim 1, wherein X² is CR² and X³ is CH.
6. The compound according to claim 1, wherein R⁴ is H.
7. The compound according to claim 1, wherein R² is C₁₋₆ alkyl.
8. The compound according to claim 1, wherein R³ is C₁₋₆ alkoxy or C₁₋₆ alkyl.
9. The compound according to claim 1, wherein R¹ is —OR¹', optionally substituted with one or more R¹''.
10. A compound, selected from the group consisting of:
4-(6-methylpyridin-2-ylamino)-6-phenoxypyridazine-3-carboxamide;
6-(3-cyanophenoxy)-4-(6-methylpyridin-2-ylamino) pyridazine-3-carboxamide;
6-(3-(2-aminopropan-2-yl)phenoxy)-4-(6-methylpyridin-2-ylamino)pyridazine-3-carboxamide;
6-(3-fluorophenoxy)-4-(6-methylpyridin-2-ylamino) pyridazine-3-carboxamide;
4-(6-methylpyridin-2-ylamino)-6-(pyridin-3-yloxy) pyridazine-3-carboxamide;
6-(2-cyanophenoxy)-4-(6-methylpyridin-2-ylamino) pyridazine-3-carboxamide;
6-(2-ethylphenoxy)-4-(6-methylpyridin-2-ylamino) pyridazine-3-carboxamide;
4-(6-methylpyridin-2-ylamino)-6-(o-tolyloxy)pyridazine-3-carboxamide;
6-(4-chloro-2-cyanophenoxy)-4-(6-methylpyridin-2-ylamino)pyridazine-3-carboxamide;
6-(2-cyclopropylphenoxy)-4-(6-methylpyridin-2-ylamino)pyridazine-3-carboxamide;
4-(6-Cyclopropyl-pyridin-2-ylamino)-6-oxo-1,6-di-hydro-pyridazine-3-carboxylic acid amide;
6-(1-amino-4-methylpentan-2-ylamino)-4-(6-tert-butylpyridin-2-ylamino)pyridazine-3-carboxamide;
6-(2-aminoethoxy)-4-(5,6-dimethylpyridin-2-ylamino) pyridazine-3-carboxamide;
6-chloro-4-(3,5-dimethylphenylamino)pyridazine-3-carboxamide;
6-(1-Aminomethyl-3-methyl-butylamino)-4-(6-isopropyl-5-methyl-pyridin-2-ylamino)-pyridazine-3-carboxylic acid amide;
6-(2-aminoethylamino)-4-(6-tert-butylpyridin-2-ylamino)pyridazine-3-carboxamide;
6-((R)-1-Aminomethyl-3-methyl-butylamino)-4-(6-tert-butyl-pyridin-2-ylamino)-pyridazine-3-carboxylic acid amide;
(6-(2-aminoethylamino)-4-(6-isopropyl-5-methylpyridin-2-ylamino)pyridazine-3-carboxamide;
6-((1-aminocyclopropyl)methylamino)-4-(6-tert-butylpyridin-2-ylamino)pyridazine-3-carboxamide;
6-(2-aminoethylamino)-4-(6-isopropyl-5-methoxypyridin-2-ylamino)pyridazine-3-carboxamide;

6-(2-aminoethylamino)-4-(6-(2-cyanopropan-2-yl)pyridin-2-ylamino)pyridazine-3-carboxamide;
6-(2-aminoethylamino)-4-(6-(2-hydroxypropan-2-yl)pyridin-2-ylamino)pyridazine-3-carboxamide;
6-(2-aminoethylamino)-4-(6-(trifluoromethyl)pyridin-2-ylamino)pyridazine-3-carboxamide;
6-(2-aminoethylamino)-4-(5-methoxy-6-propylpyridin-2-ylamino)pyridazine-3-carboxamide;
6-(2-aminoethylamino)-4-(6-(dimethylamino)-5-methylpyridin-2-ylamino)pyridazine-3-carboxamide;
6-(2-aminoethylamino)-4-(6-(2-methoxypropan-2-yl)pyridin-2-ylamino)pyridazine-3-carboxamide;
6-(2-aminoethylamino)-4-(5-isopropyl-6-methoxypyridin-2-ylamino)pyridazine-3-carboxamide;
6-(2-aminoethylamino)-4-(5-fluoro-6-isopropylpyridin-2-ylamino)pyridazine-3-carboxamide;
6-(2-aminoethylamino)-4-(6-isopropoxypyridin-2-ylamino)pyridazine-3-carboxamide; and
6-(2-Aminoethylamino)-4-(5,6-dimethylpyridin-2-ylamino)pyridazine-3-carboxamide,
or a pharmaceutically acceptable salt thereof.

11. A pharmaceutical composition, comprising a therapeutically effective amount of a compound according to claim 1, or a pharmaceutically acceptable salt thereof, admixed with at least one pharmaceutically acceptable carrier, excipient or diluent.

* * * * *